US007776822B2

(12) United States Patent
Terman

(10) Patent No.: US 7,776,822 B2
(45) Date of Patent: Aug. 17, 2010

(54) INTRATHECAL AND INTRATUMORAL SUPERANTIGENS TO TREAT MALIGNANT DISEASE

(75) Inventor: David S. Terman, Pebble Beach, CA (US)

(73) Assignee: Jenquest, Carmel, CA (US)

( * ) Notice: Subject to any disclaimer, the term of this patent is extended or adjusted under 35 U.S.C. 154(b) by 0 days.

(21) Appl. No.: 10/513,466

(22) PCT Filed: May 8, 2003

(86) PCT No.: PCT/US03/14381

§ 371 (c)(1),
(2), (4) Date: Jun. 13, 2005

(87) PCT Pub. No.: WO03/094846

PCT Pub. Date: Nov. 20, 2003

(65) Prior Publication Data

US 2006/0052295 A1 Mar. 9, 2006

(51) Int. Cl.
A61K 38/17 (2006.01)
A61K 39/00 (2006.01)

(52) U.S. Cl. .................... 514/12; 424/277.1
(58) Field of Classification Search .......... 514/12; 424/277.1
See application file for complete search history.

(56) References Cited

U.S. PATENT DOCUMENTS

| 5,194,596 | A | * | 3/1993 | Tischer et al. ............. 530/399 |
| 5,350,836 | A | * | 9/1994 | Kopchick et al. ......... 530/399 |
| 5,858,363 | A | * | 1/1999 | Dohlsten et al. ......... 424/183.1 |
| 6,126,945 | A | * | 10/2000 | Terman et al. ........... 424/237.1 |
| 6,187,908 | B1 | | 2/2001 | Terrett et al. |
| 6,692,746 | B1 | * | 2/2004 | Terman et al. ........... 424/184.1 |
| 7,179,625 | B2 | | 2/2007 | Han et al. |
| 7,220,724 | B2 | | 5/2007 | Markland, Jr. et al. |

OTHER PUBLICATIONS

Mondal et al. (Biochem. Biophys. Res. Commun. 290:1336-1342 (2002)).*
Alpaugh et al. (Clin. Can. Res. 4:1903-1914 (1998)).*
Sundberg et al. (Current Op. Immunol. 14(1):36-44 (2002)).*
Scholnick et al (Trends in Biotechnology, 18(1):34-39, 2000).*
Burgess et al, Journal of Cell Biology vol. 111 Nov. 1990 2129-2138.*
Lazar et al Molecular and Cellular Biology Mar. 1988 vol. 8 No. 3 1247-1252.*
Terman et al. (Clin. Chest Med. 27:321-334 (2006)).*
Takemura et al. (Can. Immunol. Immunother. 51:33-44 (2002).*
Terman et al. (Science 209:1257-1259 (1980)).*
Stedman's Medical Dictionary definition of "parenteral" (p. 1).*
Plautz et al. (Cell. Immunol. 171:277-284 (1996).*
Benjamin et al., 1998, Development 125:1591-1598.*
Vukicevic et al. (1996, PNAS USA 93:9021-9026).*
Massague,1987, Cell 49:437-8.*
Pilbeam et al., 1993, Bone 14:717-720.*
Bork (2000, Genome Research 10:398-400).*
Doerks et al. (1998, Trends in Genetics 14:248-250).*
Smith et al. (1997, Nature Biotechnology 15:1222-1223).*
Brenner (1999, Trends in Genetics 15:132-133).*
Bork (1996, Trends in Genetics 12:425-427).*
Bowie et al. (1990, Science 247:1306-1310).*
Das et al. (Immunol. Letts. 70:43-51 (1991).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Imanishi K et al., Activation of murine T cells by streptococcal pyrogenic exotoxin type A. Requirement for MHC class II molecules on accessory cells and identification of V beta elements in T cell receptor of toxin-reactive T cells J Immunol 145:3170-6 (1990.
Merino M and Mackall CL, Treatment strategies for solid tumors and implications on host defense in Wingard JR and Bowden RA eds Management of Infection in Oncology Patients p. 8-10 Taylor & Francis, Independence KY (2003).
Hedlund G et al., Superantigen-based tumor therapy: in vivo activation of cytotoxic T cells Canc Immunol Immunother 36: 89-93 (1993).
Cheng J et al., Individualized patient dosing in phase I clinical trials: The role of escalation with overdose control in PNU-214936 J Clin Oncol. 22: 602-609 (2004).

(Continued)

Primary Examiner—Lynn Bristol
(74) Attorney, Agent, or Firm—Central Coast Patent Agency

(57) ABSTRACT

The presence of tumor nodules in organs often results in serious clinical manifestations and the permeation by cancer cells of sheaths surrounding organs often produces clinical manifestations of pleural effusion, ascites or cerebral edema. The present invention addresses this problem by providing a method for treating tumors comprising (a) intratumoral administration of a superantigen and/or (b) intrathecal or intracavitary administration of a superantigen directly into the sheath. Intratumoral superantigen results in significant and sustained reduction of the tumor size. Intrathecal administration produces significant sustained reduction of the fluid accumulation associated with clinical improvement and prolonged survival. Useful superantigen compositions for intrathecal and intratumoral injection include tumoricidally effective homologues, fragments and fusion proteins of native superantigens. Also disclosed is combined therapy that includes intratumoral or intrathecal superantigen compositions in combination with (i) intratumoral low, non-toxic doses of one or more chemotherapeutic drugs or (ii) systemic chemotherapy at reduced and non-toxic doses of chemotherapeutic drugs.

4 Claims, 2 Drawing Sheets

OTHER PUBLICATIONS

Belka C. et al. Impact of localized radiotherapy on blood immune cells counts and function in humans Radiotherapy and Oncology 50 199-204(1999).

Rosendahl A et al., T-Cell Cytotoxicity Assays for Studying the Functional Interaction Between the Superantigen Staphylococcal Enterotoxin A and T-Cell Receptors in Methods in Molecular Biology, vol. 145: Bacterial Toxins: Methods and Protocols Edited by: O. Hoist, Humana Press Inc., Totowa, NJ (1993).

Massague J TBFβ family of growth and differentiation factors Cell 49: 437-438, (1987).

Tester W et al., Innovative treatments for non-small cell lung cancer Expert Opin Investig Drugs 10:1021-1032 (2001).

Lamphear et al., J Immunol 160: 615-623,1998.

Chen W Novel Cancer Vaccines Expert Opin Ther Patents 13: 1787-1799 (2003).

Le Poole C et al., Recent Progress in Cancer Vaccine Development Expert Opin Investig Drugs 12: 971-981 (2003).

Declaration of Dr. Eugene Spier (Jan. 29, 2002) in prosecution of USSN 669274 and Ep patent 6692746.

Declaration of Professor Howard Grey, Sep. 25, 2003 and Attachments A1-A26 in prosecution of EP patent 1129717.

Declaration of Professor Howard Grey Declaration of Professor Howard Grey Aug. 28, 2002 with Exhibits A-D in prosecution of EP patent 1129717.

Declaration of Dr. Saleem Khan Sep. 18, 1995 in prosecution of US patent 6126945 and EP patent 1103268.

Declaration of Professor William R. Pearson (Jan. 30, 2002) in prosecution of US patent 6692746 and EP patent 1129717.

Shearer WT et al., [(IgG)2 Protein A]2 Complex Stimulates Cytosine Arabinoside Incorporation into DNA and Inhibits L Cell Proliferation Immunopharmacology, 8: 103-I 10 (1984).

Shearer WT et al., IgG-Protein A complexes modulate thymidine incorporation into DNA of antibody and complement-stimulated cells J. Immunol. 142: 2279-84 (1984).

Das C, Langone, JJ. Dissociation between murine speleen cell mitogenic activity of enterotoxins and antitumor activity of Staphylococcal protein J. Immunol. 142: 2943-2948 ( 1989).

Bertram et al., Staphylococcal Protein A Column: Correlation of Mitogenicity of PerfusedPlasma with Clinical Response Cancer Res. 45, 4486-4494 (1985).

Cooper PD et al., Substances that can trigger activation of the alternate pathway of complement in mice Int. J. Cancer Int. J. Cancer 33: 683-687 (1984).

Nakanishi K et al., Plasma Therapy of Primary Rat Mammary Carcinoma: Dependence of Consumption of C3 during Absorption of Plasma with Sepharose Derivatives on the Anticoagulant Cancer Res 45: 4122-4127 (1985).

Lipman DJ et al., Rapid and sensitive protein searches Science 235: 1435-1441 (1985).

Pearson WR et al., Improved tools for biological sequence comparison Proc. Natl. Acad. Sci. 85:2444-2448 (1988).

Gattinoni L et al., Removal of homeostatic cytokine sinks by lymphodepletion enhances the efficacy of adoptively transferred tumor-specific CD8 T cells J Exp Med 202: 907-912 (2005).

Das C and Langone JJ Dissociation between murine spleen cell mitogenic activity of enterotoxins contaminants and anti-tumor activitiy of protein A J Immunol 142. 2943-2948 (1989).

12. Belka et al., Radiother Oncol 50:199-204 (1999).

Van Solingen P et al.., "Cloning and expression of an endocellulase gene from a novel streptomycete isolated from an East African soda lake", Extremophiles 5:333-341 (2001).

Boyce, JM et al.., "Genomic Sequence of a Calnexin Homolog from *Arabidopsis thaliana*", Plant Physiol. 106: 1691 (1994).

Ren Lai et al., "Bombinakinin M gene associated peptide, a novel bioactive peptide from skin secretions of the toad *Bombina maxima*", Peptides 24: 199-204 (2003).

Snow M et al., "Characterisation of the putative nucleoprotein gene of infectious salmon anaemia virus (ISAV)" Virus Research 74: 111-118 (2001).

Lattuada D et al., "Monoclonal Antibody Against Human Growth Hormone Receptor", Hybridoma 19: 177-183 (2000).

Labedan B et al., "Widespread Protein Sequence Similarities: Origins of *Escherichia coli* Genes", Journal of Bacteriology 177: 1585-1588: (1995).

Piccinni E et al., "Purification and primary structure of metallothioneins induced by cadmium in the protists *Tetrahymena pigmentosa* and *Tetrahymena pyriformis*", Eur. J. Biochem. 226: 853-859 (1994).

Han et al., US patent 7179625, U.S. Appl. No. 10/758,672, non-final rejection Nov. 10, 2005 / Applicant's remarks/ amendment May 8, 2006.

Terrett et al., US patent 6187908, U.S. Appl. No. 08/977,865, non-final rejection Oct. 15, 1998.

Terrett et al., US patent 6187908, U.S. Appl. No. 08/977,865, Applicant's amendment Jan. 19, 1999.

Markland et al., US Patent 7220724, U.S. Appl. No. 10/713,584, non-final rejection Dec. 5, 2005.

Nakanishi K et al., "Serotherapy of Primary Rat Mammary Carcinoma: Inhibition by Ethylenedinitrilotetraacetic Acid but not by [Ethylenebis(oxyethylenenitrilo)]tetraacetic Acid" Cancer Res 46, 3886-3890 (1986).

Gladys MG et al., "Serotherapy of Cancer: Cellular Changes in Primary Rat Mammary Carcinomas After infusion of Syngeneic Sera Absorbed with Protein A Sepharose" Int. J. Cancer 42,16-83 (1988).

Bertram JH et al., "Staphylococcal Protein A Column: Correlation of Mitogenicity of Perfused Plasma with Clinical Response" Cancer Res 45, 4486-4494 (1985).

Sukumar S. et al., "Plasma therapy of primary rat mammary carcinoma: antitumor activity of tumor-bearer plasma adsorbed against inactivated CNBr sepharose or protein A-sepharose". J Biol Response Mod. 3:303-15 (1984).

Migita k. et al., FK506 Augments Activation-induced Programmed Cell Death of T Lymphocytes In Vivo J. Clin. Invest 96: 727-732 (1995).

Terman DS et al., "Antitumor' Effects of Immobilized Protein A and Staphylococcal Products: Linkage between Toxicity and Efficacy, and Identification of Potential Tumoricidal Reagents" Eur J Cancer Clin Oncol. 21: 1115-22 (1985).

Das C et al., "Dissociation between Murine Spleen Cell Mitogenic Activity of Staphylococcal Protein A Enterotoxin Contaminants and Anti-tumor Activity" J Immunol 142: 2943-2948 (1989).

Terman DS "Preparation of Protein A Immobilized on Collodion-Coated Charcoal and Plasma Perfusion System for Treatment of Cancer" Methods in Enzymology 137: 496-515 (1988).

Das C et al., "Correlation between antitumor activity of protein A and in vivo formation of defined high molecular weight complexes with immunoglobulin G in BALB/c mice". Cancer Res. 47:2002-7 (1987).

Shearer WT et al., "[(IgG)2 protein A]2 complex stimulates cytosine arabinoside incorporation into DNA and inhibits L cell proliferation" Immunopharmacology. Oct. 1984;8(2):103- 110.

Gattinoni G et al., Removal of homeostatic cytokine sinks by lymphodepletion enhances the efficacy of adoptively transferred tumor-specific CD8 T cells J Exp Med 202: 907-912 (2005).

Langone JJ et al., ."Generation of human C3a, C4a, and C5a anaphylatoxins by protein A of *Staphylococcus aureus* and immobilized protein A reagents used in serotherapy of cancer". J Immunol. 133:1057-63 (1984).

Cooper PD et al., "Substances that can Trigger Activation of the Alternate Pathway of Complement have Antitumor Actiity in Mice" Int. J. Cancer: 33: 683-687 (1984).

Cooper PD et al., "Protein A treatment of Cancer: Activation of a Serum Component with Transspecies Ant-B16 Melanoma Activity" Int. J. Cancer: 32: 737-744 (1983).

Balint J et. al., Tumoricidal Response following Perfusion over Immobilized Protein A: Identification of Immunoglobulin Oligomers in Serum after Perfusion and Their Partial Characterization1 Cancer Res 44, 734-743 (1984).

Patentee's Rebuttal to Opponent's New Evidence and Remarks on "Inventive step" Mar. 31, 2008 EP B1129717.

Interlocutory Decision and Minutes of Opposition Proceedings of Apr. 15, 2008 EP B1129717.

Bergdoll M. Enterotoxins in Staphylococci and Staphylococcal Infections, Ed by Eastman & Adams, Academic Press, 1983 pp. 591-592.

Terman DS et al., Generation of tumor specific antibodies in plasma after perfusion over immobized Protein A Clin Res. 29: 377A (1981).

Belka et al., Impact of localized radiotherapy on blood immune cells counts and 1. function in humans Radiother Oncol 50:199-204(1999).

Messerschmidt et al Protein A Immunoadsorption in the Treatment of Malignant Disease J Clin Oncol 6,203-212 (1988).

Hedlund et al., Superantigen-based tumor therapy:in vivo activation of cytotoxic T cells Cancer Immunol Immunother 36: 89-93 (1993).

Nakanishi K et al., Plasma Therapy of Primary Rat Mammary Carcinoma: Dependence of Consumption of C3 during Absorption of Plasma with Sepharose Derivatives on the Anticoagulant Cancer Res 45: 4122-4127 (1985).

Merino M & Mackall CL. Treatment Strategies for solid tumors and implications on host defense in Wingard JR & Bowden RA eds Management of Infection in Oncology Patients p. 8-10 Taylor & Francis, Independence KY (2003).

* cited by examiner

SEQUENCE LISTING

<160> NUMBER OF SEQ ID NOS: 23

<210> SEQ ID NO 1
<211> LENGTH: 231
<212> TYPE: PRT
<213> ORGANISM: Staphylococcus sp.

<400> SEQUENCE: 1

Ser Glu Lys Ser Glu Glu Ile Asn Glu Lys Asp Leu Arg Lys Lys Ser
1               5                   10                  15

Glu Leu Gln Gly Thr Ala Gly Asn Lys Gln Ile Tyr Tyr Tyr Asn Glu
            20                  25                  30

Lys Ala Lys Thr Glu Asn Lys Glu Ser His Asp Gln Phe Leu Gln His
        35                  40                  45

Thr Ile Leu Phe Lys Gly Phe Phe Thr Asp His Ser Trp Tyr Asn Asp
    50                  55                  60

Leu Leu Val Asp Phe Asp Ser Lys Asp Ile Val Asp Lys Tyr Lys Gly
65                  70                  75                  80

Lys Lys Val Asp Leu Tyr Gly Ala Tyr Tyr Gly Tyr Gln Cys Ala Gly
                85                  90                  95

Gly Thr Pro Asn Lys Thr Ala Cys Met Tyr Gly Gly Val Thr Leu His
            100                 105                 110

Asp Asn Asn Arg Leu Thr Glu Glu Lys Lys Val Pro Ile Asn Leu Trp
        115                 120                 125

Leu Asp Gly Lys Gln Asn Thr Val Pro Leu Glu Thr Val Lys Thr Asn
    130                 135                 140

Lys Lys Asn Val Thr Val Gln Glu Leu Asp Leu Gln Ala Arg Arg Tyr
145                 150                 155                 160

Leu Gln Glu Lys Tyr Asn Leu Tyr Asn Ser Asp Val Phe Asp Gly Lys
                165                 170                 175

Val Gln Arg Gly Leu Ile Val Phe His Thr Ser Thr Glu Pro Ser Val
            180                 185                 190

Asn Tyr Asp Leu Phe Gly Ala Gln Gly Gln Tyr Ser Asn Thr Leu Leu
        195                 200                 205

Arg Ile Tyr Arg Asp Asn Lys Ser Ile Asn Ser Glu Asn Met His Ile
    210                 215                 220

Asp Ile Tyr Leu Tyr Thr Ser
225                 230

<210> SEQ ID NO 2
<211> LENGTH: 238
<212> TYPE: PRT
<213> ORGANISM: Staphylococcus sp.

<400> SEQUENCE: 2

Glu Ser Gln Pro Asp Pro Lys Pro Asp Glu Leu His Lys Ser Ser Lys
1               5                   10                  15

Phe Thr Gly Leu Met Glu Asn Met Lys Val Leu Tyr Asp Asp Asn His
            20                  25                  30

Val Ser Ala Ile Asn Val Lys Ser Ile Asp Gln Phe Leu Tyr Phe Asp
        35                  40                  45

Leu Ile Tyr Ser Ile Lys Asp Thr Lys Leu Gly Asn Tyr Asp Asn Val
    50                  55                  60

Arg Val Glu Phe Lys Asn Lys Asp Leu Ala Asp Lys Tyr Lys Asp Lys
65                  70                  75                  80

```
Tyr Val Asp Val Phe Gly Ala Asn Tyr Tyr Gln Cys Tyr Phe Ser
             85                  90                  95

Lys Lys Thr Asn Asp Ile Asn Ser His Gln Thr Asp Lys Arg Lys Thr
            100                 105                 110

Cys Met Tyr Gly Gly Val Thr Glu His Asn Gly Asn Gln Leu Asp Lys
            115                 120                 125

Tyr Arg Ser Ile Thr Val Arg Val Phe Glu Asp Gly Lys Asn Leu Leu
            130                 135                 140

Ser Phe Asp Val Gln Thr Asn Lys Lys Val Thr Ala Gln Glu Leu
145                 150                 155                 160

Asp Tyr Leu Thr Arg His Tyr Leu Val Lys Asn Lys Lys Leu Tyr Glu
                165                 170                 175

Phe Asn Asn Ser Pro Tyr Glu Thr Gly Tyr Ile Lys Phe Ile Glu Asn
            180                 185                 190

Glu Asn Ser Phe Trp Tyr Asp Met Met Pro Ala Pro Gly Asp Lys Phe
            195                 200                 205

Asp Gln Ser Lys Tyr Leu Met Met Tyr Asn Asp Asn Lys Met Val Asp
            210                 215                 220

Ser Lys Asp Val Lys Ile Glu Val Tyr Leu Thr Thr Lys Lys
225                 230                 235
```

<210> SEQ ID NO 3
<211> LENGTH: 240
<212> TYPE: PRT
<213> ORGANISM: Staphylococcus sp.

<400> SEQUENCE: 3

```
Met Asn Lys Ser Arg Phe Ile Ser Cys Val Ile Leu Ile Phe Ala Leu
1               5                   10                  15

Ile Leu Val Leu Phe Thr Pro Asn Val Leu Ala Glu Ser Gln Pro Asp
            20                  25                  30

Pro Thr Pro Asp Glu Leu His Lys Ala Ser Lys Phe Thr Gly Leu Met
            35                  40                  45

Glu Asn Met Lys Val Leu Tyr Asp Asp His Tyr Val Ser Ala Thr Lys
50                  55                  60

Val Lys Ser Val Asp Lys Phe Leu Ala His Asp Leu Ile Tyr Asn Ile
65                  70                  75                  80

Ser Asp Lys Lys Leu Lys Asn Tyr Asp Lys Val Lys Thr Glu Leu Leu
            85                  90                  95

Asn Glu Gly Leu Ala Lys Lys Tyr Lys Asp Glu Val Val Asp Val Tyr
            100                 105                 110

Gly Ser Asn Tyr Tyr Val Asn Cys Tyr Phe Ser Ser Lys Asp Asn Val
            115                 120                 125

Gly Lys Val Thr Gly Gly Lys Thr Cys Met Tyr Gly Gly Ile Thr Lys
            130                 135                 140

His Glu Gly Asn His Phe Asp Asn Gly Asn Leu Gln Asn Val Leu Ile
145                 150                 155                 160

Arg Val Tyr Glu Asn Lys Arg Asn Thr Ile Ser Phe Glu Val Gln Thr
                165                 170                 175

Asp Lys Lys Ser Val Thr Ala Gln Glu Leu Asp Ile Lys Ala Arg Asn
            180                 185                 190

Phe Leu Ile Asn Lys Lys Asn Leu Tyr Glu Phe Asn Ser Ser Pro Tyr
            195                 200                 205

Glu Thr Gly Tyr Ile Lys Phe Ile Glu Asn Asn Gly Asn Thr Phe Trp
            210                 215                 220
```

```
Tyr Asp Met Met Pro Ala Pro Gly Asp Lys Phe Asp Gln Ser Lys Tyr
225                 230                 235                 240
```

<210> SEQ ID NO 4
<211> LENGTH: 239
<212> TYPE: PRT
<213> ORGANISM: Staphylococcus sp.

<400> SEQUENCE: 4

```
Glu Ser Gln Pro Asp Pro Thr Pro Asp Glu Leu His Lys Ser Ser Glu
1               5                   10                  15

Phe Thr Gly Thr Met Gly Asn Met Lys Tyr Leu Tyr Asp Asp His Tyr
            20                  25                  30

Val Ser Ala Thr Lys Val Met Ser Val Asp Lys Phe Leu Ala His Asp
            35                  40                  45

Leu Ile Tyr Asn Ile Ser Asp Lys Lys Leu Lys Asn Tyr Asp Lys Val
50                  55                  60

Lys Thr Glu Leu Leu Asn Glu Asp Leu Ala Lys Tyr Lys Asp Glu
65                  70                  75                  80

Val Val Asp Val Tyr Gly Ser Asn Tyr Val Asn Cys Tyr Phe Ser
                    85                  90                  95

Ser Lys Asp Asn Val Gly Lys Val Thr Gly Gly Lys Thr Cys Met Tyr
                100                 105                 110

Gly Gly Ile Thr Lys His Glu Gly Asn His Phe Asp Asn Gly Asn Leu
                115                 120                 125

Gln Asn Val Leu Ile Arg Val Tyr Glu Asn Lys Arg Asn Thr Ile Ser
130                 135                 140

Phe Glu Val Gln Thr Asp Lys Lys Ser Val Thr Ala Gln Glu Leu Asp
145                 150                 155                 160

Ile Lys Ala Arg Asn Phe Leu Ile Asn Lys Lys Asn Leu Tyr Glu Phe
                165                 170                 175

Asn Ser Ser Pro Tyr Glu Thr Gly Tyr Ile Lys Phe Ile Glu Asn Asn
                180                 185                 190

Gly Asn Thr Phe Trp Tyr Asp Met Met Pro Ala Pro Gly Asp Lys Phe
                195                 200                 205

Asp Gln Ser Lys Tyr Leu Met Met Tyr Asn Asp Asn Lys Thr Val Asp
            210                 215                 220

Ser Lys Ser Val Lys Ile Glu Val His Leu Thr Thr Lys Asn Gly
225                 230                 235
```

<210> SEQ ID NO 5
<211> LENGTH: 266
<212> TYPE: PRT
<213> ORGANISM: Staphylococcus sp.

<400> SEQUENCE: 5

```
Met Tyr Lys Arg Leu Phe Ile Ser Arg Val Ile Leu Ile Phe Ala Leu
1               5                   10                  15

Ile Leu Val Ile Ser Thr Pro Asn Val Leu Ala Glu Ser Gln Pro Asp
            20                  25                  30

Pro Met Pro Asp Asp Leu His Lys Ser Ser Glu Phe Thr Gly Thr Met
            35                  40                  45

Gly Asn Met Lys Tyr Leu Tyr Asp Asp His Tyr Val Ser Ala Thr Lys
            50                  55                  60

Val Lys Ser Val Asp Lys Phe Leu Ala His Asp Leu Ile Tyr Asn Ile
65                  70                  75                  80

Ser Asp Lys Lys Leu Lys Asn Tyr Asp Lys Val Lys Thr Glu Leu Leu
```

```
                85                  90                  95
Asn Glu Asp Leu Ala Lys Lys Tyr Lys Asp Glu Val Val Asp Val Tyr
                100                 105                 110

Gly Ser Asn Tyr Tyr Val Asn Cys Tyr Phe Ser Ser Lys Asp Asn Val
            115                 120                 125

Gly Lys Val Thr Gly Lys Thr Cys Met Tyr Gly Gly Ile Thr Lys
        130                 135                 140

His Glu Gly Asn His Phe Asp Asn Gly Asn Leu Gln Asn Val Leu Val
145                 150                 155                 160

Arg Val Tyr Glu Asn Lys Arg Asn Thr Ile Ser Phe Glu Val Gln Thr
                165                 170                 175

Asp Lys Lys Ser Val Thr Ala Gln Glu Leu Asp Ile Lys Ala Arg Asn
            180                 185                 190

Phe Leu Ile Asn Lys Lys Asn Leu Tyr Glu Phe Asn Ser Ser Pro Tyr
        195                 200                 205

Glu Thr Gly Tyr Ile Lys Phe Ile Glu Asn Asn Gly Asn Thr Phe Trp
    210                 215                 220

Tyr Asp Met Met Pro Ala Pro Gly Asp Lys Phe Asp Gln Ser Lys Tyr
225                 230                 235                 240

Leu Met Met Tyr Asn Asp Asn Lys Thr Val Asp Ser Lys Ser Val Lys
                245                 250                 255

Ile Glu Val His Leu Thr Thr Lys Asn Gly
            260                 265

<210> SEQ ID NO 6
<211> LENGTH: 258
<212> TYPE: PRT
<213> ORGANISM: Staphylococcus sp.

<400> SEQUENCE: 6

Met Lys Lys Phe Asn Ile Leu Ile Ala Leu Leu Phe Phe Thr Ser Leu
1               5                   10                  15

Val Ile Ser Pro Leu Asn Val Lys Ala Asn Glu Asn Ile Asp Ser Val
            20                  25                  30

Lys Glu Lys Glu Leu His Lys Lys Ser Glu Leu Ser Ser Thr Ala Leu
        35                  40                  45

Asn Asn Met Lys His Ser Tyr Ala Asp Lys Asn Pro Ile Ile Gly Glu
    50                  55                  60

Asn Lys Ser Thr Gly Asp Gln Phe Leu Glu Asn Thr Leu Leu Tyr Lys
65                  70                  75                  80

Lys Phe Phe Thr Asp Leu Ile Asn Phe Glu Asp Leu Leu Ile Asn Phe
                85                  90                  95

Asn Ser Lys Glu Met Ala Gln His Phe Lys Ser Lys Asn Val Asp Val
                100                 105                 110

Tyr Pro Ile Arg Tyr Ser Ile Asn Cys Tyr Gly Gly Glu Ile Asp Arg
            115                 120                 125

Thr Ala Cys Thr Tyr Gly Gly Val Thr Pro His Glu Gly Asn Lys Leu
        130                 135                 140

Lys Glu Arg Lys Lys Ile Pro Ile Asn Leu Trp Ile Asn Gly Val Gln
145                 150                 155                 160

Lys Glu Val Ser Leu Asp Lys Val Gln Thr Asp Lys Lys Asn Val Thr
                165                 170                 175

Val Gln Glu Leu Asp Ala Gln Ala Arg Arg Tyr Leu Gln Lys Asp Leu
            180                 185                 190

Lys Leu Tyr Asn Asn Asp Thr Leu Gly Gly Lys Ile Gln Arg Gly Lys
```

```
                    195                 200                 205
Ile Glu Phe Asp Ser Ser Asp Gly Ser Lys Val Ser Tyr Asp Leu Phe
    210                 215                 220

Asp Val Lys Gly Asp Phe Pro Glu Lys Gln Leu Arg Ile Tyr Ser Asp
225                 230                 235                 240

Asn Lys Thr Leu Ser Thr Glu His Leu His Ile Asp Ile Tyr Leu Tyr
                245                 250                 255

Glu Lys

<210> SEQ ID NO 7
<211> LENGTH: 257
<212> TYPE: PRT
<213> ORGANISM: Staphylococcus sp.

<400> SEQUENCE: 7

Met Lys Lys Thr Ala Phe Ile Leu Leu Leu Phe Ile Ala Leu Thr Leu
1               5                   10                  15

Thr Thr Ser Pro Leu Val Asn Gly Ser Glu Lys Ser Glu Glu Ile Asn
                20                  25                  30

Glu Lys Asp Leu Arg Lys Lys Ser Glu Leu Gln Arg Asn Ala Leu Ser
            35                  40                  45

Asn Leu Arg Gln Ile Tyr Tyr Tyr Asn Glu Lys Ala Ile Thr Glu Asn
        50                  55                  60

Lys Glu Ser Asp Asp Gln Phe Leu Glu Asn Thr Leu Leu Phe Lys Gly
65                  70                  75                  80

Phe Phe Thr Gly His Pro Trp Tyr Asn Asp Leu Leu Val Asp Leu Gly
                85                  90                  95

Ser Lys Asp Ala Thr Asn Lys Tyr Lys Gly Lys Lys Val Asp Leu Tyr
                100                 105                 110

Gly Ala Tyr Tyr Gly Tyr Gln Cys Ala Gly Gly Thr Pro Asn Lys Thr
            115                 120                 125

Ala Cys Met Tyr Gly Gly Val Thr Leu His Asp Asn Asn Arg Leu Thr
        130                 135                 140

Glu Glu Lys Lys Val Pro Ile Asn Leu Trp Ile Asp Gly Lys Gln Thr
145                 150                 155                 160

Thr Val Pro Ile Asp Lys Val Lys Thr Ser Lys Lys Glu Val Thr Val
                165                 170                 175

Gln Glu Leu Asp Leu Gln Ala Arg His Tyr Leu His Gly Lys Phe Gly
            180                 185                 190

Leu Tyr Asn Ser Asp Ser Phe Gly Gly Lys Val Gln Arg Gly Leu Ile
        195                 200                 205

Val Phe His Ser Ser Glu Gly Ser Thr Val Ser Tyr Asp Leu Phe Asp
    210                 215                 220

Ala Gln Gly Gln Tyr Pro Asp Thr Leu Leu Arg Ile Tyr Arg Asp Asn
225                 230                 235                 240

Lys Thr Ile Asn Ser Glu Asn Leu His Ile Asp Leu Tyr Leu Tyr Thr
                245                 250                 255

Thr

<210> SEQ ID NO 8
<211> LENGTH: 234
<212> TYPE: PRT
<213> ORGANISM: Staphylococcus sp.

<400> SEQUENCE: 8

Met Asn Lys Lys Leu Leu Met Asn Phe Phe Ile Val Ser Pro Leu Leu
```

-continued

```
              1               5              10              15
            Leu Ala Thr Thr Ala Thr Asp Phe Thr Pro Val Pro Leu Ser Ser Asn
                             20                  25                  30

Gln Ile Ile Lys Thr Ala Lys Ala Ser Thr Asn Asp Asn Ile Lys Asp
                         35                  40                  45

Leu Leu Asp Trp Tyr Ser Ser Gly Ser Asp Thr Phe Thr Asn Ser Glu
                     50                  55                  60

Val Leu Asp Asn Ser Leu Gly Ser Met Arg Ile Lys Asn Thr Asp Gly
             65                  70                  75                  80

Ser Ile Ser Leu Ile Ile Phe Pro Ser Pro Tyr Tyr Ser Pro Ala Phe
                                 85                  90                  95

Thr Lys Gly Glu Lys Val Asp Leu Asn Thr Lys Arg Thr Lys Lys Ser
                            100                 105                 110

Gln His Thr Ser Glu Gly Thr Tyr Ile His Phe Gln Ile Ser Gly Val
                        115                 120                 125

Thr Asn Thr Glu Lys Leu Pro Thr Pro Ile Glu Leu Pro Leu Lys Val
                    130                 135                 140

Lys Val His Gly Lys Asp Ser Pro Leu Lys Tyr Gly Pro Lys Phe Asp
            145                 150                 155                 160

Lys Lys Gln Leu Ala Ile Ser Thr Leu Asp Phe Glu Ile Arg His Gln
                                165                 170                 175

Leu Thr Gln Ile His Gly Leu Tyr Arg Ser Ser Asp Lys Thr Gly Gly
                            180                 185                 190

Tyr Trp Lys Ile Thr Met Asn Asp Gly Ser Thr Tyr Gln Ser Asp Leu
                        195                 200                 205

Ser Lys Lys Phe Glu Tyr Asn Thr Glu Lys Pro Pro Ile Asn Ile Asp
                    210                 215                 220

Glu Ile Lys Thr Ile Glu Ala Glu Ile Asn
            225                 230

<210> SEQ ID NO 9
<211> LENGTH: 242
<212> TYPE: PRT
<213> ORGANISM: Staphylococcus sp.

<400> SEQUENCE: 9

Met Asn Lys Ile Phe Arg Val Leu Thr Val Ser Leu Phe Phe Phe Thr
             1               5                  10                  15

Phe Leu Ile Lys Asn Asn Leu Ala Tyr Ala Asp Val Gly Val Ile Asn
                             20                  25                  30

Leu Arg Asn Phe Tyr Ala Asn Tyr Gln Pro Glu Lys Leu Gln Gly Val
                         35                  40                  45

Ser Ser Gly Asn Phe Ser Thr Ser His Gln Leu Glu Tyr Ile Asp Gly
                     50                  55                  60

Lys Tyr Thr Leu Tyr Ser Gln Phe His Asn Glu Tyr Glu Ala Lys Arg
             65                  70                  75                  80

Leu Lys Asp His Lys Val Asp Ile Phe Gly Ile Ser Tyr Ser Gly Leu
                                 85                  90                  95

Cys Asn Thr Lys Tyr Met Tyr Gly Gly Ile Thr Leu Ala Asn Gln Asn
                            100                 105                 110

Leu Asp Lys Pro Arg Asn Ile Pro Ile Asn Leu Trp Val Asn Gly Lys
                        115                 120                 125

Gln Asn Thr Ile Ser Thr Asp Lys Val Ser Gln Lys Lys Glu Val
                    130                 135                 140

Thr Ala Gln Glu Ile Asp Ile Lys Leu Arg Lys Tyr Leu Gln Asn Glu
```

```
            145                 150                 155                 160
Tyr Asn Ile Tyr Gly Phe Asn Lys Thr Lys Lys Gly Gln Glu Tyr Gly
                    165                 170                 175

Tyr Lys Ser Lys Phe Asn Ser Gly Phe Asn Lys Gly Lys Ile Thr Phe
                180                 185                 190

His Leu Asn Asn Glu Pro Ser Phe Thr Tyr Asp Leu Phe Tyr Thr Gly
            195                 200                 205

Thr Gly Gln Ala Glu Ser Phe Leu Lys Ile Tyr Asn Asp Asn Lys Thr
        210                 215                 220

Ile Asp Ala Glu Asn Phe His Leu Asp Val Glu Ile Ser Tyr Glu Lys
225                 230                 235                 240

Thr Glu

<210> SEQ ID NO 10
<211> LENGTH: 217
<212> TYPE: PRT
<213> ORGANISM: Staphylococcus sp.

<400> SEQUENCE: 10

Glu Asp Leu His Asp Lys Ser Glu Leu Thr Asp Leu Ala Leu Ala Asn
1               5                   10                  15

Ala Tyr Gly Gln Tyr Asn His Pro Phe Ile Lys Glu Asn Ile Lys Ser
            20                  25                  30

Asp Glu Ile Ser Gly Glu Lys Asp Leu Ile Phe Arg Asn Gln Gly Asp
        35                  40                  45

Ser Gly Asn Asp Leu Arg Val Lys Phe Ala Thr Ala Asp Leu Ala Gln
    50                  55                  60

Lys Phe Lys Asn Lys Asn Val Asp Ile Tyr Gly Ala Ser Phe Tyr Tyr
65                  70                  75                  80

Lys Cys Glu Lys Ile Ser Glu Asn Ile Ser Glu Cys Leu Tyr Gly Gly
                85                  90                  95

Thr Thr Leu Asn Ser Glu Lys Leu Ala Gln Glu Arg Val Ile Gly Ala
            100                 105                 110

Asn Val Trp Val Asp Gly Ile Gln Lys Glu Thr Glu Leu Ile Arg Thr
        115                 120                 125

Asn Lys Lys Asn Val Thr Leu Gln Glu Leu Asp Ile Lys Ile Arg Lys
    130                 135                 140

Ile Leu Ser Asp Lys Tyr Lys Ile Tyr Tyr Lys Asp Ser Glu Ile Ser
145                 150                 155                 160

Lys Gly Leu Ile Glu Phe Asp Met Lys Thr Pro Arg Asp Tyr Ser Phe
                165                 170                 175

Asp Ile Tyr Asp Leu Lys Gly Glu Asn Asp Tyr Glu Ile Asp Lys Ile
            180                 185                 190

Tyr Glu Asp Asn Lys Thr Leu Lys Ser Asp Asp Ile Ser His Ile Asp
        195                 200                 205

Val Asn Leu Tyr Thr Lys Lys Val
    210                 215

<210> SEQ ID NO 11
<211> LENGTH: 242
<212> TYPE: PRT
<213> ORGANISM: Staphylococcus sp.

<400> SEQUENCE: 11

Met Lys Lys Phe Lys Tyr Ser Phe Ile Leu Val Phe Ile Leu Leu Phe
1               5                   10                  15
```

Asn Ile Lys Asp Leu Thr Tyr Ala Gln Gly Asp Ile Gly Val Gly Asn
            20                  25                  30

Leu Arg Asn Phe Tyr Thr Lys His Asp Tyr Ile Asp Leu Lys Gly Val
        35                  40                  45

Thr Asp Lys Asn Leu Pro Ile Ala Asn Gln Leu Glu Phe Ser Thr Gly
50                  55                  60

Thr Asn Asp Leu Ile Ser Glu Ser Asn Trp Asp Glu Ile Ser Lys
65                  70                  75                  80

Phe Lys Gly Lys Lys Leu Asp Ile Phe Gly Ile Asp Tyr Asn Gly Pro
                85                  90                  95

Cys Lys Ser Lys Tyr Met Tyr Gly Gly Ala Thr Leu Ser Gly Gln Tyr
            100                 105                 110

Leu Asn Ser Ala Arg Lys Ile Pro Ile Asn Leu Trp Val Asn Gly Lys
        115                 120                 125

His Lys Thr Ile Ser Thr Asp Lys Ile Ala Thr Asn Lys Lys Leu Val
    130                 135                 140

Thr Ala Gln Glu Ile Asp Val Lys Leu Arg Arg Tyr Leu Gln Glu Glu
145                 150                 155                 160

Tyr Asn Ile Tyr Gly His Asn Asn Thr Gly Lys Gly Lys Glu Tyr Gly
                165                 170                 175

Tyr Lys Ser Lys Phe Tyr Ser Gly Phe Asn Asn Gly Lys Val Leu Phe
            180                 185                 190

His Leu Asn Asn Glu Lys Ser Phe Ser Tyr Asp Leu Phe Tyr Thr Gly
        195                 200                 205

Asp Gly Leu Pro Val Ser Phe Leu Lys Ile Tyr Glu Asp Asn Lys Ile
    210                 215                 220

Ile Glu Ser Glu Lys Phe His Leu Asp Val Glu Ile Ser Tyr Val Asp
225                 230                 235                 240

Ser Asn

<210> SEQ ID NO 12
<211> LENGTH: 268
<212> TYPE: PRT
<213> ORGANISM: Staphylococcus sp.

<400> SEQUENCE: 12

Met Lys Lys Thr Ile Phe Ile Leu Ile Phe Ser Leu Thr Leu Thr Leu
1               5                   10                  15

Leu Ile Thr Pro Leu Val Tyr Ser Asp Ser Lys Asn Glu Thr Ile Lys
            20                  25                  30

Glu Lys Asn Leu His Lys Lys Ser Glu Leu Ser Ser Ile Thr Leu Asn
        35                  40                  45

Asn Leu Arg His Ile Tyr Phe Phe Asn Glu Lys Gly Ile Ser Glu Lys
    50                  55                  60

Ile Met Thr Glu Asp Gln Phe Leu Asp Tyr Thr Leu Leu Phe Lys Ser
65                  70                  75                  80

Phe Phe Ile Ser His Ser Gln Tyr Asn Asp Leu Leu Val Gln Phe Asp
                85                  90                  95

Ser Lys Glu Thr Val Asn Lys Phe Lys Gly Lys Gln Val Asp Leu Tyr
            100                 105                 110

Gly Ser Tyr Tyr Gly Phe Gln Cys Ser Gly Gly Lys Pro Asn Lys Thr
        115                 120                 125

Ala Cys Met Tyr Gly Gly Val Thr Leu His Glu Asn Asn Gln Leu Tyr
    130                 135                 140

Asp Thr Lys Lys Ile Pro Ile Asn Leu Trp Ile Asp Ser Ile Arg Thr

```
            145                 150                 155                 160
Val Val Pro Leu Asp Ile Val Lys Thr Asn Lys Lys Val Thr Ile
                    165                 170                 175

Gln Glu Leu Asp Leu Gln Ala Arg Tyr Tyr Leu His Lys Gln Tyr Asn
                    180                 185                 190

Leu Tyr Asn Pro Ser Thr Phe Asp Gly Lys Ile Gln Lys Gly Leu Ile
                    195                 200                 205

Val Phe His Thr Ser Lys Glu Pro Leu Val Ser Tyr Asp Leu Phe Asn
                    210                 215                 220

Val Ile Gly Gln Tyr Pro Asp Lys Leu Leu Lys Ile Tyr Gln Asp Asn
225                 230                 235                 240

Lys Ile Ile Glu Ser Glu Asn Met His Ile Asp Ile Tyr Leu Tyr Thr
                    245                 250                 255

Ser Leu Ile Val Leu Ile Ser Leu Pro Leu Val Leu
                    260                 265

<210> SEQ ID NO 13
<211> LENGTH: 242
<212> TYPE: PRT
<213> ORGANISM: Staphylococcus sp.

<400> SEQUENCE: 13

Met Lys Lys Leu Ile Ser Ile Leu Leu Ile Asn Ile Ile Leu Gly
1               5                   10                  15

Val Ser Asn Asn Ala Ser Ala Gln Gly Asp Ile Gly Ile Asp Asn Leu
                20                  25                  30

Arg Asn Phe Tyr Thr Lys Lys Asp Phe Ile Asn Leu Lys Asp Val Lys
                35                  40                  45

Asp Asn Asp Thr Pro Ile Ala Asn Gln Leu Gln Phe Ser Asn Glu Ser
            50                  55                  60

Tyr Asp Leu Ile Ser Glu Ser Lys Asp Phe Asn Lys Phe Ser Asn Phe
65                  70                  75                  80

Lys Gly Lys Lys Leu Asp Val Phe Gly Ile Ser Tyr Asn Gly Gln Cys
                85                  90                  95

Asn Thr Lys Tyr Ile Tyr Gly Gly Ile Thr Ala Thr Asn Glu Tyr Leu
                100                 105                 110

Asp Lys Pro Arg Asn Ile Pro Ile Asn Ile Trp Ile Asn Gly Asn His
                115                 120                 125

Lys Thr Ile Ser Thr Asn Lys Val Ser Thr Asn Lys Lys Phe Val Thr
            130                 135                 140

Ala Gln Glu Ile Asp Ile Lys Leu Arg Arg Tyr Leu Gln Glu Glu Tyr
145                 150                 155                 160

Asn Ile Tyr Gly His Asn Gly Thr Lys Lys Gly Glu Glu Tyr Gly His
                165                 170                 175

Lys Ser Lys Phe Tyr Ser Gly Phe Asn Ile Gly Lys Val Thr Phe His
                180                 185                 190

Leu Asn Asn Asn Asp Thr Phe Ser Tyr Asp Leu Phe Tyr Thr Gly Asp
                195                 200                 205

Asp Gly Leu Pro Lys Ser Phe Leu Lys Ile Tyr Glu Asp Asn Lys Thr
            210                 215                 220

Val Glu Ser Glu Lys Phe His Leu Asp Val Asp Ile Ser Tyr Lys Glu
225                 230                 235                 240

Thr Lys

<210> SEQ ID NO 14
```

```
<211> LENGTH: 240
<212> TYPE: PRT
<213> ORGANISM: Staphylococcus sp.

<400> SEQUENCE: 14
```

| | | | | | | | | | | | | | | |
|---|---|---|---|---|---|---|---|---|---|---|---|---|---|---|
| Met | Lys | Lys | Arg | Leu | Leu | Phe | Val | Ile | Val | Ile | Thr | Leu | Phe | Ile | Phe |
| 1 | | | | 5 | | | | | 10 | | | | | 15 | |
| Ser | Ser | Asn | His | Thr | Val | Leu | Ser | Asn | Gly | Asp | Val | Gly | Pro | Gly | Asn |
| | | | 20 | | | | | 25 | | | | | 30 | | |
| Leu | Arg | Asn | Phe | Tyr | Thr | Lys | Tyr | Glu | Tyr | Val | Asn | Leu | Lys | Asn | Val |
| | | | 35 | | | | | 40 | | | | | 45 | | |
| Lys | Asp | Lys | Asn | Ser | Pro | Glu | Ser | His | Arg | Leu | Glu | Tyr | Ser | Tyr | Lys |
| 50 | | | | | 55 | | | | | 60 | | | | | |
| Asn | Asp | Thr | Leu | Tyr | Ala | Glu | Phe | Asp | Asn | Glu | Tyr | Ile | Thr | Ser | Asp |
| 65 | | | | | 70 | | | | | 75 | | | | | 80 |
| Leu | Lys | Gly | Lys | Asn | Val | Asp | Val | Phe | Gly | Ile | Ser | Tyr | Lys | Tyr | Gly |
| | | | | 85 | | | | | 90 | | | | | 95 | |
| Ser | Asn | Ser | Arg | Thr | Ile | Tyr | Gly | Gly | Val | Thr | Lys | Ala | Glu | Asn | Asn |
| | | | 100 | | | | | 105 | | | | | 110 | | |
| Lys | Leu | Asp | Ser | Pro | Arg | Ile | Ile | Pro | Ile | Asn | Leu | Ile | Ile | Asn | Gly |
| | | | 115 | | | | | 120 | | | | | 125 | | |
| Lys | His | Gln | Thr | Val | Thr | Thr | Lys | Ser | Val | Ser | Thr | Asp | Lys | Lys | Met |
| | | 130 | | | | | 135 | | | | | 140 | | | |
| Val | Thr | Ala | Gln | Glu | Ile | Asp | Val | Lys | Leu | Arg | Lys | Tyr | Leu | Gln | Asp |
| 145 | | | | | 150 | | | | | 155 | | | | | 160 |
| Glu | Phe | Asn | Ile | Tyr | Gly | His | Asn | Asp | Thr | Gly | Lys | Gly | Lys | Glu | Tyr |
| | | | | 165 | | | | | 170 | | | | | 175 | |
| Gly | Thr | Ser | Ser | Lys | Phe | Tyr | Ser | Gly | Phe | Asp | Lys | Gly | Ser | Val | Val |
| | | | 180 | | | | | 185 | | | | | 190 | | |
| Phe | His | Met | Asn | Asp | Gly | Ser | Asn | Phe | Ser | Tyr | Asp | Leu | Phe | Tyr | Thr |
| | | | 195 | | | | | 200 | | | | | 205 | | |
| Gly | Tyr | Gly | Leu | Pro | Glu | Ser | Phe | Leu | Lys | Ile | Tyr | Lys | Asp | Asn | Lys |
| | | 210 | | | | | 215 | | | | | 220 | | | |
| Thr | Val | Asp | Ser | Thr | Gln | Phe | His | Leu | Asp | Val | Glu | Ile | Ser | Lys | Arg |
| 225 | | | | | 230 | | | | | 235 | | | | | 240 |

```
<210> SEQ ID NO 15
<211> LENGTH: 239
<212> TYPE: PRT
<213> ORGANISM: Staphylococcus sp.

<400> SEQUENCE: 15
```

| | | | | | | | | | | | | | | |
|---|---|---|---|---|---|---|---|---|---|---|---|---|---|---|
| Met | Lys | Arg | Ile | Leu | Ile | Ile | Val | Val | Leu | Leu | Phe | Cys | Tyr | Ser | Gln |
| 1 | | | | 5 | | | | | 10 | | | | | 15 | |
| Asn | His | Ile | Ala | Thr | Ala | Asp | Val | Gly | Val | Leu | Asn | Leu | Arg | Asn | Tyr |
| | | | 20 | | | | | 25 | | | | | 30 | | |
| Tyr | Gly | Ser | Tyr | Pro | Ile | Glu | Asp | His | Gln | Ser | Ile | Asn | Pro | Glu | Asn |
| | | | 35 | | | | | 40 | | | | | 45 | | |
| Asn | His | Leu | Ser | His | Gln | Leu | Val | Phe | Ser | Met | Asp | Asn | Ser | Thr | Val |
| | | 50 | | | | | 55 | | | | | 60 | | | |
| Thr | Ala | Glu | Phe | Lys | Asn | Val | Asp | Asp | Val | Lys | Lys | Phe | Lys | Asn | His |
| 65 | | | | | 70 | | | | | 75 | | | | | 80 |
| Ala | Val | Asp | Val | Tyr | Gly | Leu | Ser | Tyr | Ser | Gly | Tyr | Cys | Leu | Lys | Asn |
| | | | | 85 | | | | | 90 | | | | | 95 | |
| Lys | Tyr | Ile | Tyr | Gly | Gly | Val | Thr | Leu | Ala | Gly | Asp | Tyr | Leu | Glu | Lys |
| | | | 100 | | | | | 105 | | | | | 110 | | |

```
Ser Arg Arg Ile Pro Ile Asn Leu Trp Val Asn Gly Glu His Gln Thr
            115                 120                 125

Ile Ser Thr Asp Lys Val Ser Thr Asn Lys Lys Leu Val Thr Ala Gln
130                 135                 140

Glu Ile Asp Thr Lys Leu Arg Arg Tyr Leu Gln Glu Glu Tyr Asn Ile
145                 150                 155                 160

Tyr Gly Phe Asn Asp Thr Asn Lys Gly Arg Asn Tyr Gly Asn Lys Ser
                165                 170                 175

Lys Phe Ser Ser Gly Phe Asn Ala Gly Lys Ile Leu Phe His Leu Asn
                180                 185                 190

Asp Gly Ser Ser Phe Ser Tyr Asp Leu Phe Asp Thr Gly Thr Gly Gln
                195                 200                 205

Ala Glu Ser Phe Leu Lys Ile Tyr Asn Asp Asn Lys Thr Val Glu Thr
210                 215                 220

Glu Lys Phe His Leu Asp Val Glu Ile Ser Tyr Lys Asp Glu Ser
225                 230                 235

<210> SEQ ID NO 16
<211> LENGTH: 251
<212> TYPE: PRT
<213> ORGANISM: Streptococcus sp.

<400> SEQUENCE: 16

Met Glu Asn Asn Lys Lys Val Leu Lys Lys Met Val Phe Phe Val Leu
1               5                   10                  15

Val Thr Phe Leu Gly Leu Thr Ile Ser Gln Glu Val Phe Ala Gln Gln
                20                  25                  30

Asp Pro Asp Pro Ser Gln Leu His Arg Ser Ser Leu Val Lys Asn Leu
                35                  40                  45

Gln Asn Ile Tyr Phe Leu Tyr Glu Gly Asp Pro Val Thr His Glu Asn
50                  55                  60

Val Lys Ser Val Asp Gln Leu Leu Ser His Asp Leu Ile Tyr Asn Val
65                  70                  75                  80

Ser Gly Pro Asn Tyr Asp Lys Leu Lys Thr Glu Leu Lys Asn Gln Glu
                85                  90                  95

Met Ala Thr Leu Phe Lys Asp Lys Asn Val Asp Ile Tyr Gly Val Glu
                100                 105                 110

Tyr Tyr His Leu Cys Tyr Leu Cys Glu Asn Ala Glu Arg Ser Ala Cys
                115                 120                 125

Ile Tyr Gly Gly Val Thr Asn His Glu Gly Asn His Leu Glu Ile Pro
130                 135                 140

Lys Lys Ile Val Val Lys Val Ser Ile Asp Gly Ile Gln Ser Leu Ser
145                 150                 155                 160

Phe Asp Ile Glu Thr Asn Lys Lys Met Val Thr Ala Gln Glu Leu Asp
                165                 170                 175

Tyr Lys Val Arg Lys Tyr Leu Thr Asp Asn Lys Gln Leu Tyr Thr Asn
                180                 185                 190

Gly Pro Ser Lys Tyr Glu Thr Gly Tyr Ile Lys Phe Ile Pro Lys Asn
                195                 200                 205

Lys Glu Ser Phe Trp Phe Asp Phe Phe Pro Glu Pro Glu Phe Thr Gln
210                 215                 220

Ser Lys Tyr Leu Met Ile Tyr Lys Asp Asn Glu Thr Leu Asp Ser Asn
225                 230                 235                 240

Thr Ser Gln Ile Glu Val Tyr Leu Thr Thr Lys
                245                 250
```

-continued

<210> SEQ ID NO 17
<211> LENGTH: 398
<212> TYPE: PRT
<213> ORGANISM: Streptococcus sp.

<400> SEQUENCE: 17

Met Asn Lys Lys Lys Leu Gly Ile Arg Leu Leu Ser Leu Leu Ala Leu
1               5                   10                  15

Gly Gly Phe Val Leu Ala Asn Pro Val Phe Ala Asp Gln Asn Phe Ala
            20                  25                  30

Arg Asn Glu Lys Glu Ala Lys Asp Ser Ala Ile Thr Phe Ile Gln Lys
        35                  40                  45

Ser Ala Ala Ile Lys Ala Gly Ala Arg Ser Ala Glu Asp Ile Lys Leu
    50                  55                  60

Asp Lys Val Asn Leu Gly Gly Glu Leu Ser Gly Ser Asn Met Tyr Val
65                  70                  75                  80

Tyr Asn Ile Ser Thr Gly Gly Phe Val Ile Val Ser Gly Asp Lys Arg
                85                  90                  95

Ser Pro Glu Ile Leu Gly Tyr Ser Thr Ser Gly Ser Phe Asp Ala Asn
            100                 105                 110

Gly Lys Glu Asn Ile Ala Ser Phe Met Glu Ser Tyr Val Glu Gln Ile
        115                 120                 125

Lys Glu Asn Lys Lys Leu Asp Thr Thr Tyr Ala Gly Thr Ala Glu Ile
    130                 135                 140

Lys Gln Pro Val Val Lys Ser Leu Leu Asp Ser Lys Gly Ile His Tyr
145                 150                 155                 160

Asn Gln Gly Asn Pro Tyr Asn Leu Leu Thr Pro Val Ile Glu Lys Val
                165                 170                 175

Lys Pro Gly Glu Gln Ser Phe Val Gly Gln His Ala Ala Thr Gly Cys
            180                 185                 190

Val Ala Thr Ala Thr Ala Gln Ile Met Lys Tyr His Asn Tyr Pro Asn
        195                 200                 205

Lys Gly Leu Lys Asp Tyr Thr Tyr Thr Leu Ser Ser Asn Asn Pro Tyr
    210                 215                 220

Phe Asn His Pro Lys Asn Leu Phe Ala Ala Ile Ser Thr Arg Gln Tyr
225                 230                 235                 240

Asn Trp Asn Asn Ile Leu Pro Thr Tyr Ser Gly Arg Glu Ser Asn Val
                245                 250                 255

Gln Lys Met Ala Ile Ser Glu Leu Met Ala Asp Val Gly Ile Ser Val
            260                 265                 270

Asp Met Asp Tyr Gly Pro Ser Ser Gly Ser Ala Gly Ser Ser Arg Val
        275                 280                 285

Gln Arg Ala Leu Lys Glu Asn Phe Gly Tyr Asn Gln Ser Val His Gln
    290                 295                 300

Ile Asn Arg Ser Asp Phe Ser Lys Gln Asp Trp Glu Ala Gln Ile Asp
305                 310                 315                 320

Lys Glu Leu Ser Gln Asn Gln Pro Val Tyr Tyr Gln Gly Val Gly Lys
                325                 330                 335

Val Gly Gly His Ala Phe Val Ile Asp Gly Ala Asp Gly Arg Asn Phe
            340                 345                 350

Tyr His Val Asn Trp Gly Trp Gly Val Ser Asp Gly Phe Phe Arg
        355                 360                 365

Leu Asp Ala Leu Asn Pro Ser Ala Leu Gly Thr Gly Gly Gly Ala Gly
    370                 375                 380

Gly Phe Asn Gly Tyr Gln Ser Ala Val Val Gly Ile Lys Pro
385                 390                 395

<210> SEQ ID NO 18
<211> LENGTH: 234
<212> TYPE: PRT
<213> ORGANISM: Streptococcus sp.

<400> SEQUENCE: 18

Met Lys Lys Ile Asn Ile Ile Lys Ile Val Phe Ile Ile Thr Val Ile
1               5                   10                  15

Leu Ile Ser Thr Ile Ser Pro Ile Ile Lys Ser Asp Ser Lys Lys Asp
            20                  25                  30

Ile Ser Asn Val Lys Ser Asp Leu Leu Tyr Ala Tyr Thr Ile Thr Pro
        35                  40                  45

Tyr Asp Tyr Lys Asp Cys Arg Val Asn Phe Ser Thr Thr His Thr Leu
    50                  55                  60

Asn Ile Asp Thr Gln Lys Tyr Arg Gly Lys Asp Tyr Tyr Ile Ser Ser
65                  70                  75                  80

Glu Met Ser Tyr Glu Ala Ser Gln Lys Phe Lys Arg Asp Asp His Val
                85                  90                  95

Asp Val Phe Gly Leu Phe Tyr Ile Leu Asn Ser His Thr Gly Glu Tyr
            100                 105                 110

Ile Tyr Gly Gly Ile Thr Pro Ala Gln Asn Asn Lys Val Asn His Lys
        115                 120                 125

Leu Leu Gly Asn Leu Phe Ile Ser Gly Glu Ser Gln Gln Asn Leu Asn
    130                 135                 140

Asn Lys Ile Ile Leu Glu Lys Asp Ile Val Thr Phe Gln Glu Ile Asp
145                 150                 155                 160

Phe Lys Ile Arg Lys Tyr Leu Met Asp Asn Tyr Lys Ile Tyr Asp Ala
                165                 170                 175

Thr Ser Pro Tyr Val Ser Gly Arg Ile Glu Ile Gly Thr Lys Asp Gly
            180                 185                 190

Lys His Glu Gln Ile Asp Leu Phe Asp Ser Pro Asn Glu Gly Thr Arg
        195                 200                 205

Ser Asp Ile Phe Ala Lys Tyr Lys Asp Asn Arg Ile Ile Asn Met Lys
    210                 215                 220

Asn Phe Ser His Phe Asp Ile Tyr Leu Glu
225                 230

<210> SEQ ID NO 19
<211> LENGTH: 260
<212> TYPE: PRT
<213> ORGANISM: Streptococcus sp.

<400> SEQUENCE: 19

Met Asn Lys Arg Ile Arg Ile Leu Val Val Ala Cys Val Val Phe Cys
1               5                   10                  15

Ala Gln Leu Leu Ser Ile Ser Val Phe Ala Ser Ser Gln Pro Asp Pro
            20                  25                  30

Thr Pro Glu Gln Leu Asn Lys Ser Ser Gln Phe Thr Gly Val Met Gly
        35                  40                  45

Asn Leu Arg Cys Leu Tyr Asp Asn His Phe Val Glu Gly Thr Asn Val
    50                  55                  60

Arg Ser Thr Gly Gln Leu Leu Gln His Asp Leu Ile Phe Pro Ile Lys
65                  70                  75                  80

Asp Leu Lys Leu Lys Asn Tyr Asp Ser Val Lys Thr Glu Phe Asn Ser

```
                       85                  90                  95
Lys Asp Leu Ala Ala Lys Tyr Lys Asn Lys Asp Val Asp Ile Phe Gly
            100                 105                 110

Ser Asn Tyr Tyr Tyr Asn Cys Tyr Ser Glu Gly Asn Ser Cys Lys
            115                 120                 125

Asn Ala Lys Lys Thr Cys Met Tyr Gly Gly Val Thr Glu His His Arg
            130                 135                 140

Asn Gln Ile Glu Gly Lys Phe Pro Asn Ile Thr Val Lys Val Tyr Glu
145                 150                 155                 160

Asp Asn Glu Asn Ile Leu Ser Phe Asp Ile Thr Thr Asn Lys Lys Gln
                165                 170                 175

Val Thr Val Gln Glu Leu Asp Cys Lys Thr Arg Lys Ile Leu Val Ser
            180                 185                 190

Arg Lys Asn Leu Tyr Glu Phe Asn Asn Ser Pro Tyr Glu Thr Gly Tyr
            195                 200                 205

Ile Lys Phe Ile Glu Ser Ser Gly Asp Ser Phe Trp Tyr Asp Met Met
            210                 215                 220

Pro Ala Pro Gly Ala Ile Phe Asp Gln Ser Lys Tyr Leu Met Leu Tyr
225                 230                 235                 240

Asn Asp Asn Lys Thr Val Ser Ser Ser Ala Ile Ala Ile Glu Val His
                245                 250                 255

Leu Thr Lys Lys
            260

<210> SEQ ID NO 20
<211> LENGTH: 210
<212> TYPE: PRT
<213> ORGANISM: Streptococcus sp.

<400> SEQUENCE: 20

Asp Glu Asn Leu Lys Asp Leu Lys Arg Ser Leu Arg Phe Ala Tyr Asn
1               5                   10                  15

Ile Thr Pro Cys Asp Tyr Glu Asn Val Glu Ile Ala Phe Val Thr Thr
            20                  25                  30

Asn Ser Ile His Ile Asn Thr Lys Gln Lys Arg Ser Glu Cys Ile Leu
        35                  40                  45

Tyr Val Asp Ser Ile Val Ser Leu Gly Ile Thr Asp Gln Phe Ile Lys
50                  55                  60

Gly Asp Lys Val Asp Val Phe Gly Leu Pro Tyr Asn Phe Ser Pro Pro
65                  70                  75                  80

Tyr Val Asp Asn Ile Tyr Gly Gly Ile Val Lys His Ser Asn Gln Gly
                85                  90                  95

Asn Lys Ser Leu Gln Phe Val Gly Ile Leu Asn Gln Asp Gly Lys Glu
            100                 105                 110

Thr Tyr Leu Pro Ser Glu Val Val Arg Ile Lys Lys Lys Gln Phe Thr
            115                 120                 125

Leu Gln Glu Phe Asp Phe Lys Ile Arg Lys Phe Leu Met Glu Lys Tyr
            130                 135                 140

Asn Ile Tyr Asp Ser Glu Ser Arg Tyr Thr Ser Gly Ser Leu Phe Leu
145                 150                 155                 160

Ala Thr Lys Asp Ser Lys His Tyr Glu Val Asp Leu Phe Asn Lys Asp
                165                 170                 175

Asp Lys Leu Leu Ser Arg Asp Ser Phe Phe Lys Arg Tyr Lys Asp Asn
            180                 185                 190

Lys Ile Phe Asn Ser Glu Glu Ile Ser His Phe Asp Ile Tyr Leu Lys
```

Thr Tyr
210

<210> SEQ ID NO 21
<211> LENGTH: 236
<212> TYPE: PRT
<213> ORGANISM: Streptococcus sp.

<400> SEQUENCE: 21

Met Arg Tyr Asn Cys Arg Tyr Ser His Ile Asp Lys Lys Ile Tyr Ser
1               5                   10                  15

Met Ile Ile Cys Leu Ser Phe Leu Leu Tyr Ser Asn Val Val Gln Ala
            20                  25                  30

Asn Ser Tyr Asn Thr Thr Asn Arg His Asn Leu Glu Ser Leu Tyr Lys
        35                  40                  45

His Asp Ser Asn Leu Ile Glu Ala Asp Ser Ile Lys Asn Ser Pro Asp
    50                  55                  60

Ile Val Thr Ser His Met Leu Lys Tyr Ser Val Lys Asp Lys Asn Leu
65                  70                  75                  80

Ser Val Phe Phe Glu Lys Asp Trp Ile Ser Gln Glu Phe Lys Asp Lys
                85                  90                  95

Glu Val Asp Ile Tyr Ala Leu Ser Ala Gln Glu Val Cys Glu Cys Pro
            100                 105                 110

Gly Lys Arg Tyr Glu Ala Phe Gly Gly Ile Thr Leu Thr Asn Ser Glu
        115                 120                 125

Lys Lys Glu Ile Lys Val Pro Val Asn Val Trp Asp Lys Ser Lys Gln
    130                 135                 140

Gln Pro Pro Met Phe Ile Thr Val Asn Lys Pro Lys Val Thr Ala Gln
145                 150                 155                 160

Glu Val Asp Ile Lys Val Arg Lys Leu Leu Ile Lys Lys Tyr Asp Ile
                165                 170                 175

Tyr Asn Asn Arg Glu Gln Lys Tyr Ser Lys Gly Thr Val Thr Leu Asp
            180                 185                 190

Leu Asn Ser Gly Lys Asp Ile Val Phe Asp Leu Tyr Tyr Phe Gly Asn
        195                 200                 205

Gly Asp Phe Asn Ser Met Leu Lys Ile Tyr Ser Asn Asn Glu Arg Ile
    210                 215                 220

Asp Ser Thr Gln Phe His Val Asp Val Ser Ile Ser
225                 230                 235

<210> SEQ ID NO 22
<211> LENGTH: 209
<212> TYPE: PRT
<213> ORGANISM: Streptococcus sp.

<400> SEQUENCE: 22

Leu Glu Val Asp Asn Asn Ser Leu Leu Arg Asn Ile Tyr Ser Thr Ile
1               5                   10                  15

Val Tyr Glu Tyr Ser Asp Thr Val Ile Asp Phe Lys Thr Ser His Asn
            20                  25                  30

Leu Val Thr Lys Lys Leu Asp Val Arg Asp Ala Arg Asp Phe Phe Ile
        35                  40                  45

Asn Ser Glu Met Asp Glu Tyr Ala Ala Asn Asp Phe Lys Ala Gly Asp
    50                  55                  60

Lys Ile Ala Val Phe Ser Val Pro Phe Asp Trp Asn Tyr Leu Ser Lys
65                  70                  75                  80

```
Gly Lys Val Thr Ala Tyr Thr Tyr Gly Gly Ile Thr Pro Tyr Gln Lys
                 85                  90                  95

Thr Ser Ile Pro Lys Asn Ile Pro Val Asn Leu Trp Ile Asn Arg Lys
            100                 105                 110

Gln Ile Pro Val Pro Tyr Asn Gln Ile Ser Thr Asn Lys Thr Thr Val
        115                 120                 125

Thr Ala Gln Glu Ile Asp Leu Lys Val Arg Lys Phe Leu Ile Ala Gln
    130                 135                 140

His Gln Leu Tyr Ser Ser Gly Ser Ser Tyr Lys Ser Gly Lys Leu Val
145                 150                 155                 160

Phe His Thr Asn Asp Asn Ser Asp Lys Tyr Ser Leu Asp Leu Phe Tyr
                165                 170                 175

Thr Gly Tyr Arg Asp Lys Glu Ser Ile Phe Lys Val Tyr Lys Asp Asn
            180                 185                 190

Lys Ser Phe Asn Ile Asp Lys Ile Gly His Leu Asp Ile Glu Ile Asp
        195                 200                 205

Ser

<210> SEQ ID NO 23
<211> LENGTH: 150
<212> TYPE: PRT
<213> ORGANISM: Yersinia pseudotuberculosis

<400> SEQUENCE: 23

Met Lys Lys Lys Phe Leu Ser Leu Leu Thr Leu Thr Phe Phe Ser Gly
1               5                   10                  15

Leu Ala Leu Ala Ala Asp Tyr Asp Asn Thr Leu Asn Ser Ile Pro Ser
            20                  25                  30

Leu Arg Ile Pro Asn Ile Glu Thr Tyr Thr Gly Thr Ile Gln Gly Lys
        35                  40                  45

Gly Glu Val Cys Ile Arg Gly Asn Lys Glu Gly Lys Ser Arg Gly Gly
    50                  55                  60

Glu Leu Tyr Ala Val Leu Arg Ser Thr Asn Ala Asn Ala Asp Met Thr
65                  70                  75                  80

Leu Ile Leu Leu Cys Ser Ile Arg Asp Gly Trp Lys Glu Val Lys Arg
                85                  90                  95

Ser Asp Ile Asp Arg Pro Leu Arg Tyr Glu Tyr Tyr Thr Pro Gly
            100                 105                 110

Ala Leu Ser Trp Ile Trp Glu Ile Lys Asn Asn Ser Ser Glu Ala Ser
        115                 120                 125

Asp Tyr Ser Leu Ser Ala Thr Val His Asp Asp Lys Glu Asp Ser Asp
    130                 135                 140

Val Leu Met Lys Cys Pro
145                 150
```

INTRATHECAL AND INTRATUMORAL SUPERANTIGENS TO TREAT MALIGNANT DISEASE

BACKGROUND OF THE INVENTION

1. Field of the Invention

The invention in the fields of immunology and medicine is directed to a method for treating a category of neoplastic diseases that are manifest in sheaths surrounding organs (intrathecal) by administering tumoricidal superantigens such as bacterial enterotoxins and various biologically active derivatives thereof.

2. Description of the Background Art

Staphylococcal enterotoxins ("SE's") are representative of a family of proteins known as "superantigens" (SAg)—the most powerful T lymphocyte mitogens known. They can activate between about 5 and about 30% or the total T cell population compared to the activation of 0.01% or fewer T cells by conventional antigens. Moreover, these enterotoxins elicit strong polyclonal proliferative responses at concentrations about $10^3$-fold lower than other T cell mitogens. The most potent SE on a per weight basis, Staphylococcal enterotoxin A (SEA), stimulates human T cell proliferation (measured as DNA synthesis) at concentrations of as low as $10^{-13}$-$10^{-16}$ M.

SAg-activated T cells produce a variety of cytokines, including interferon-γ (IFNγ), various interleukins and tumor necrosis factor-α (TNFα) (Dohlsten et al., *Int. J. Cancer* 54:482-488 (1993).

SAgs also stimulate other cell populations involved in innate and adaptive immunity and contribute to anti-tumor immunity. For example, SE's engage the variable (V) region of the T cell receptor (TCR) chain on the exposed face of the pleated sheet and the sides of the MHC class II molecule (Kiting B L et al., *Adv Immunol.* 1993; 54:99-166). SAgs augment $T_H1$ cytokine response by CD4+ cells while also activating cells of the NK, NKT and γ/δ T cell lineages. Cytotoxic action of NK cells is augmented by the IFNγ produced by SAg activated T cells (Morita et al., *Immunity* 14:331-44. (2001) D'Orazio J A et al., *J Immunol.* 154:1014-23 (1995).

SAgs induce tumor killing in vivo when given alone or when conjugated to tumor-specific antibodies (Terman U.S. Pat. No. 6,221,351; Dohlsten U.S. Pat. No. 5,858,363). They are also effective when employed ex vivo to induce the generation of tumor sensitized T cells that are then administered in the "adoptive therapy" of (e.g., MCA 205/207) tumors (Shu et al. *J Immunol.* 152: 1277-1288 (1994). SAg-transfected tumor cells can reduce metastatic disease in an established murine mammary carcinoma model (Pulaski et al., *Cancer Res.* 60: 2710-5 (2000).

In addition to these biological activities, the SE's share common physicochemical properties. They are heat stable, trypsin-resistant, and soluble in water and salt solutions, have similar sedimentation coefficients, diffusion constants, partial specific volumes, isoelectric points, and extinction coefficients. Prior to more recent discoveries of additional SE's, earlier-described SEs were divided into five serological types designated SEA, Staphylococcal enterotoxin B (SEB), Staphylococcal enterotoxin C (SEC), Staphylococcal enterotoxin D (SED) and Staphylococcal enterotoxin E (SEE), which exhibit striking structural similarities.

An SE is a single polypeptide chain of about 30 kDa. All SEs have a characteristic disulfide loop near the middle of the chain. SEA is a flat monomer consisting or 233 amino acids divided into two domains: domain I comprising residues 31-116 and domain II comprising residues 117-233 together with the amino tail of residues 1-30. The biologically active regions of the proteins are evolutionarily conserved and show a relatively higher degree of sequence homology/similarity. One region of striking amino acid sequence homology between SEA, SEB, SEC, SED, and SEE is located immediately on the C-terminal side of Cys-106 (in SEA). This conserved region is thought to be responsible for T cell activation. A second conserved homology region, at about residue 147, is believed to be responsible for emetic activity. This emesis-inducing region can be deleted from SE's through genetic engineering; such modified SE's are also useful therapeutics in accordance with this invention.

Sequence analysis of SEs and comparison with other bacterial toxins revealed SEA, SEB, SEC, SED, Staphylococcal toxic shock-associated toxin (TSST-1, also known as SEF), and the Streptococcal pyrogenic exotoxins (SpE's) share considerable nucleic acid and amino acid sequence similarity (Betley et al., *J. Bacteriol.* 170: 34-41 (1988)). Thus, the SEs belong to a family of evolutionarily related proteins.

SEs bind to MHC class II molecules and TCRs in a manner quite distinct from conventional antigens. SEs engage the V region of the TCR β chain (Vβ region) on an exposed face of the β pleated sheet. SEs engage the "sides" of MHC class II molecule rather than engaging the groove as do conventional antigens. In contrast to SEB and the SEC, which bind only to the MHC class II α chain, SEA, as well as SEE and SED, also interact with the MHC class II α chain in a zinc-dependent manner (Fraser J D et al., *Proc. Natl. Acad. Sci.* 89:5507-11 (1992)).

T cell recognition of SAgs, such as SEs, via the TCR Vβ region is independent of other TCR components and diversity elements. Single amino acid positions and regions important for SAg-TCR interactions have been defined. These residues are located in the vicinity of the shallow cavity formed between the two SE domains. (Lavoie P M et al., *Immunol. Rev.* 168: 257-269 (1999). Substitution of amino acid residue Asn23 in SEB by Ala has demonstrated the importance of this position in SEB/TCR interactions. This particular residue is conserved among all of the SE's and may constitute a common anchor position for SE interaction with TCR Vβ structures. Amino acid residues in positions 60-64 of SEA contribute to the TCR interaction as do the Cys residues forming the intramolecular disulfide bridge (Kappler J et al., *J. Exp. Med.* 175 387-96 (1992)). For SEC2 and SEC3, the key points of interaction in the TCR Vβ region are located in the CDR1, CDR2 and HRV4 regions of the TCR Vβ3 chain (Deringer J R et al, *Mol. Microbiol.* 22: 523-534 (1996)). Hence, multiple and highly variable parts of the Vβ region contribute to the formation of the TCRs SE binding site.

Thus far, no single, linear consensus motif in the TCR Vβ displaying a high affinity interaction with particular enterotoxins has been identified. A significant contribution of the TCRα chain in SE-TCR recognition is acknowledged (Smith et al., *J. Immunol.* 149: 887-896 (1992)). It is apparently the distinctive binding characteristics of SEs which bypass the highly variable parts of the MHC class II and TCR molecules that endows SEs with their ability to activate such a high frequency of T cells and cause massive proliferation, cytokine induction and cytotoxic T cell generation. These properties are shared by other proteins produced by various infectious agents. Together, these proteins form a well recognized family of molecules, Sags, because of their aforementioned biological effects.

Mycoplasmal, viral, and other bacterial proteins are SAgs. In addition to SEs and SpEs, examples include *Yersinia pseudotuberculosis* mitogenic protein ("YPM"), and

*Clostridium perfringens* toxin A. All SAgs activate T cells without a requirement for conventional antigen processing, and the responding T cells do not respond in a conventional MHC restricted manner. As noted, SAgs bind to and evoke responses from all T cells expressing certain TCR Vβ gene products independently of other TCR structures. CD4⁻CD8⁻ TCR α/β T cells and γ/δ T cells all respond to SAgs by proliferation, production of $T_H1$ cytokines and generation of cytotoxic activity.

Native SEs are known to induce anti-tumor effects. Administration of SEB produced antitumor effects against established tumors in two animal species, rabbits and mice, with tumors of five different histologic types: rabbit VX-2 carcinoma (Terman et al., U.S. Pat. No. 6,126,945; Terman, U.S. Pat. No. 6,340,461), murine CL 62 melanomas (Penna C. et al., *Cancer Res.* 54: 2738-2743 (1994)), murine A/20 lymphoma (Kalland T. Declaration in U.S. Ser. No. 07/689/799 (1992)), murine PRO4L fibrosarcoma (Newell et al., *Proc Natl. Acad. Sci.* 88: 1074-1079 (1991)) and human SW 620 colon carcinoma (Dohlsten et al., *Eur. J. Immunol.* 21: 1229-1233 (1991)). In these studies, parenterally-administered SEB induced objective anti-tumor effects at primary and metastatic sites. SEB was used ex vivo to stimulate a population of T cells pre-exposed to tumor, which, upon re-infusion into host animals with established pulmonary metastases, induced a substantial reduction of metastases. SEB activated T cell anti-tumor effect was specific for the immunizing tumor; the SEB stimulated T cells produced IFNγ which was thought to be an important mediator of the anti-tumor effect (Shu S et al., *J. Immunol.* 152: 1277-88 (1994)).

Fusion polypeptides comprising SEA fused to a tumor specific monoclonal antibody (mAb), designated "SEA-mAb," induced tumoricidal responses in the murine B 16 melanoma model (Dohlsten M et al., *Proc Natl Acad Sci* 91:8945-9 (1994); Dohlsten M et al., *Proc. Natl. Acad. Sci.* 88:9287-91 (1991).

Because native SEA alone was found to be ineffective in such models, Dohlsten and colleagues (U.S. Pat. No. 5,858, 363) stated that native SAg would be of "low value" particularly against MHC class II-negative tumors. When the fusion polypeptides SEA-mAb and one comprising a mutant SEA, "D227A-mAb" (these authors used 'MoAb' rather than 'mAb' for abbreviating 'monoclonal antibody') were given to human patients with advanced colon carcinoma, SEs reacted with preexisting "natural" SE-specific antibodies which diminished the antitumor effects in vivo. Following additional doses of SE-mAb preparations, the anti-SE antibody levels increased significantly (Giantonio et al., *J. Clin. Oncol.* 15:1994-2007 (1997); Alpaugh et al., *Clin. Cancer Res.* 4:1903-14 (1998); Persson et al., *Adv. Drug Del. Res.* 31: 143-152 (1998)). To date, efforts to overcome this problem have met with only partial success.

Tumors in Sheaths Encasing Organs

The appearance of tumors in sheaths ("theca") encasing organs often results in production and accumulation of large volumes of fluid in the organs' sheath. Examples include (1) pleural effusion due to fluid in the pleural sheath surrounding the lung, (2) ascites originating from fluid accumulating in the peritoneal membrane and (3) cerebral edema due to metastatic carcinomatosis of the meninges. Such effusions and fluid accumulations generally develop at an advanced stage of the disease. Malignant pleural effusion ("MPE") is the prototype of this condition. In the United States and Western Europe, 300,000 new cases of malignant pleural effusion are diagnosed annually (Antony V B et al., *Eur. Respir. J.* 18:402-419 (2001). This condition is caused by different types of tumors: lung cancer (35%), breast cancer (25%), lymphoma (10%), unknown primary malignancy (30%). It is the presenting manifestation in 10-50% of all cancers. When first evaluated, about 15% of lung cancer patients exhibit a pleural effusion. Fifty percent of cancer patients develop MPE at some point in their disease process, and up to 75% of MPE cases are symptomatic from their effusions upon presentation. The appearance of a pleural effusion in non small cell lung cancer (NSCLC) signifies Stage IIIb or Stage IV and a poor prognosis with a median survival on the order to 2-3 months (1, 7-11). In this group, no significant difference in survival were observed between those with cytologically positive and negative effusions (12). Although most of these patients are symptomatic and/or disabled from their effusions, they are not surgical candidates. They are usually offered palliative treatment with chemical pleurodesis.

Malignant ascites is associated with 30-50% of ovarian tumors. Endometrial, breast, colonic, gastric and pancreatic carcinomas make up more than 80% or the tumors associated with intra-abdominal seeding of tumor cells and ascites formation. Ascites may be the presenting manifestation in 4-69% of cases.

The major therapies for MPE include talc poudrage, talc slurry, doxycycline and bleomycin instillation (Veena et al. *Am J. Crit. Care Med.* 162: 1987-2001 (2000)). These therapies require 3-12 days of hospitalization with EKG and oximetry monitoring. A chest tube is inserted, and the therapeutic agent is infused and allowed to distribute over the pleural membranes. The chest tube is then connected to closed negative-pressure water seal drainage until pleural fluid volume drops below 100 ml/24 hours. Respiratory therapy is usually given at least once daily.

Talc poudrage requires the use of operating room and general anesthesia for thoracostomy and talc insufflation, followed by recovery room observation. Talc induces respiratory complications in up to 33% of patients and acute respiratory distress and hypoxemia in 10% of patients. Response rates to bleomycin and doxycycline range between 50% and 70%, respectively and both require continuous chest tube drainage until the output is below 100 ml/24 hours. Indwelling pleural catheters for drainage and/or injection of a pleurodesis agent are an additional option (7,8); however, the catheter requires surgical placement followed by intermittent drainage of effusion fluid at home by the patient or a caregiver.

Intrapleurally administered agents or modalities that include (a) chemotherapeutic agents such as Cisplatin, Cytarabine, Doxorubicin fluorouracil, etoposide, and mitomycin C, (b) radiation and (c) biotherapeutic agents such as IL-2, various interferons, and bacterially derived immunostimulatory agents such as *Corynebacterium parvum* have been ineffective against MPEs. Thoracentesis or chest tube drainage alone results in recurrence rates of 98% and 85% respectively within 30 days. Intraperitoneal cisplatin and etoposide has produced a complete response rate of 30% of malignant ascites. However the only randomized study has failed to show any benefit for intraperitoneal therapy over conventional intravenous chemotherapy in the initial management of stage II C to IV ovarian cancer. No definitive success of various biologic agents, e.g., IFN-α, β, and γ, TNFα or IL-2 has been reported.

The present invention overcomes these deficiencies in the treatment of MPE by providing a new therapeutic approach to this manifestation of cancer. Unlike existing therapies, The present invention is carried out entirely in an outpatient setting and requires no hospitalization at a cost several hundred percent below that of existing therapy. Major costs of the other therapies originating from hospitalization, chest tube insertion, operating and recovery room expense, respiratory therapy and in-hospital chest tube drainage, are eliminated Intratumoral SAg Therapy Prior to the present invention, therapeutic uses of SAgs have been limited to systemic administration. To improve the ability SAgs to localize to a tumor, investigators have taken two approaches. In one approach, they have produced mutant SAg molecules with reduced binding to MHC class II molecules (Hansson J et al., *Proc. Natl. Acad. Acad. Sci. USA* 94: 2489-94 (1997)). In the second approach, they have conjugated a tumor specific antibody to the SAg (Dohlsten M et al., *Proc Natl Acad Sci USA* 91:8945-9 (1994); Dohlsten M et al., *Proc Natl Acad Sci USA* 88:9287-91 (1991)). However, because SAg-specific antibodies are found in all humans, these engineered molecules, rather than localizing to tumors, are more likely to be directed to reticuloendothelial tissues where they are degraded and eliminated. The researchers cited above expressly asserted (U.S. Pat. No. 5,858,363 that native SAgs would be of "low value" for such antitumor therapy because cells of most clinically important tumors do not express MHC class II molecules. It is therefore evident that those working in this field, led by the investigators cited above, did not envision the use of the SAgs by intratumoral administration. In contrast to systemic administration, intratumoral delivery of a SAg would not require alteration of the native molecule and, as conceived by the present inventor, the presence of natural antibodies throughout the body can actually assist intratumorally-administered SAgs in evoking a tumoricidal response.

SUMMARY OF THE INVENTION

The present invention provides a method for treating malignant pleural effusion, ascites, pericardial effusion and meningeal carcinomatosis by "intrathecal" (defined below) administration of an effective amount of a SAg into the pleural space, peritoneum, pericardium, and subarachnoid space. The present invention contemplates the use of any SAg, including but not limited to staphylococcal enterotoxins ("SE") A, B, C, D, E, F, G H, I, J, K, L, M, streptococcal pyrogenic exotoxins (SpE's), *Yersinia pseudotuberculosis* SAg, *Mycoplasma arthritides* SAg, and *C. perfringens* exotoxin, administered by injection, infusion or instillation directly into a cavity or space (thecum) surrounding an organ or body region in which a tumor is present or is causing fluid accumulation.

Such spaces include the pleural space, peritoneum, subarachnoid space or dural space, or pericardial space. The generic term for administration into a sheath encasing an organ is termed "intrathecal," defined in Dorland's Medical Dictionary 29th Edition, W B Saunders (2000) and Stedman's Medical Dictionary, 27th Edition, Lippincott, Williams & Wilkins (2000) as meaning "within a sheath." As used herein, this term is intended to be broader than a more commonly used definition which is limited to intracranial spaces.

Previous publications disclose administration of SEs to a host with cancer via subcutaneous or intravenous injection or infusion. (See, for example, U.S. Pat. No. 6,126,945.) Other document disclose the administration of SAgs "locally or systemically" (U.S. Pat. No. 6,197,299; U.S. Pat. No. 5,858, 363) or in adjuvants with slow release (U.S. Pat. No. 6,126, 945, by the present inventor). However, the prior art does not disclose administration of a SAg intrathecally or more specifically, intrapleurally and intraperitoneally, to treat malignant pleural effusions and ascites. Nor does the prior art disclose the administration of a SAg intratumorally. SAgs in native form or conjugated to a tumor targeting agent such as monoclonal antibodies or their fragments ("mAbs") have been used to treat cancer in animals and humans (Hansson et al., *Proc. Natl. Acad. Sci.* 94:2489 (1997)). In all of these instances, the SAg or SAg-mAb conjugate/fusion were administered intravenously by injection or infusion.

When administered in this way SAgs or SAg conjugated to tumor specific antibodies (SAg-mAb fusion proteins) do not reach their targets in effective concentrations for two reasons. First, the SAgs are neutralized rapidly by "natural" neutralizing SAg-specific antibodies. (Giantonio et al., supra; Alpaugh et at supra; Persson et al., supra). Second, SAg-mAb fusion proteins bind to cells present in the circulation that express MHC class II proteins. One approach to overcoming these obstacles was to mutate the SAg to reduce its affinity for MHC class II. This has met with only partial success (Hansson et al supra).

The present invention obviates this obstacle to a large extent by administering a SAg (including a fragment, homologue or fusion partner), intrathecally, into sheaths encasing the organs which themselves are seeded with tumor or directly into tumor site(s). In this case, any pre-existing or induced anti-SAg antibodies may actually assist the intrathecally or intratumorally administered SAg in promoting tumor killing by binding to the SAg after it has localized to tumor cell surfaces.

The present invention covers compositions of SAg or SAg homologues consisting of amino acid substitution and deletion variants (mutants), additions (e.g., fusion proteins) and fragments with Z values>10 when the sequence is compared to a native SAg using the FASTA/FASTP programs and Monte Carlo analysis. These composition are injected, instilled or infused intrapleurally or intraperitoneally into a patient with malignant pleural effusions and/or ascites, respectively or intratumorally into tumor site(s) and induce a tumoricidal response. The SAg composition is preferably administered after partial or complete drainage of the fluid from the sheath as for example in pleural effusions via thoracentesis and ascites via paracentesis. However, the SAg composition may also be administered directly into an undrained space containing the effusion, ascites and/or carcinomatosis. The invention also contemplates the use of the nucleic acid counterparts of the native SAgs and homologues as useful for the same indications as the polypeptide form of the molecule.

To enhance the effectiveness and specificity of the SAg, it or a biologically active fragment or homologue may be fused to another protein such as (1) a tumor specific antibody, or an antigen binding fragment of such an antibody, such as an F(ab')$_2$, Fv or Fd fragment, which antibody is specific for an epitope expressed on the tumor or (b) a receptor ligand specific for any receptors selectively or preferentially expressed on tumor cells. The fusion partner can also be a powerful costimulant such as OX-40 or 4-1BB1 which enhances the T cells proliferative response to the SAg or a "Coaguligand" which promotes coagulation in the tumor vasculature.

The SAg composition is administered once every 3 to 10 days, preferably once weekly, and this schedule is continued until there is no re-accumulation of the effusion or ascites or reduction in the size of the tumor mass being injected. Three such treatments may suffice for intrathecal administration although this is an average; the number of treatments may varying from 1-6 or even higher. For intrathecal administration, the SAg composition is preferentially administered immediately after removal of pleural fluid via thoracentesis.

Unlike the other therapies for malignant pleural effusions, the present method is carried out entirely in an outpatient setting and requires no hospitalization, chest tube insertion, use of the operating room or recovery room, respiratory therapy or in-hospital chest tube drainage. In contrast to the conventional treatment for MPE noted above, instillation of the SAg composition into the pleural space has a response rate of nearly 100%. Unlike talc therapy in which up to 10% of cases may experience acute respiratory distress syndrome, the present SAg therapeutic method has not induced any significant morbidity. Hence, this invention offers decided advantages of effectiveness, safety and convenience over the prior art.

DESCRIPTION OF THE PREFERRED EMBODIMENTS

Production and Isolation of Superantigens

Figure 1:
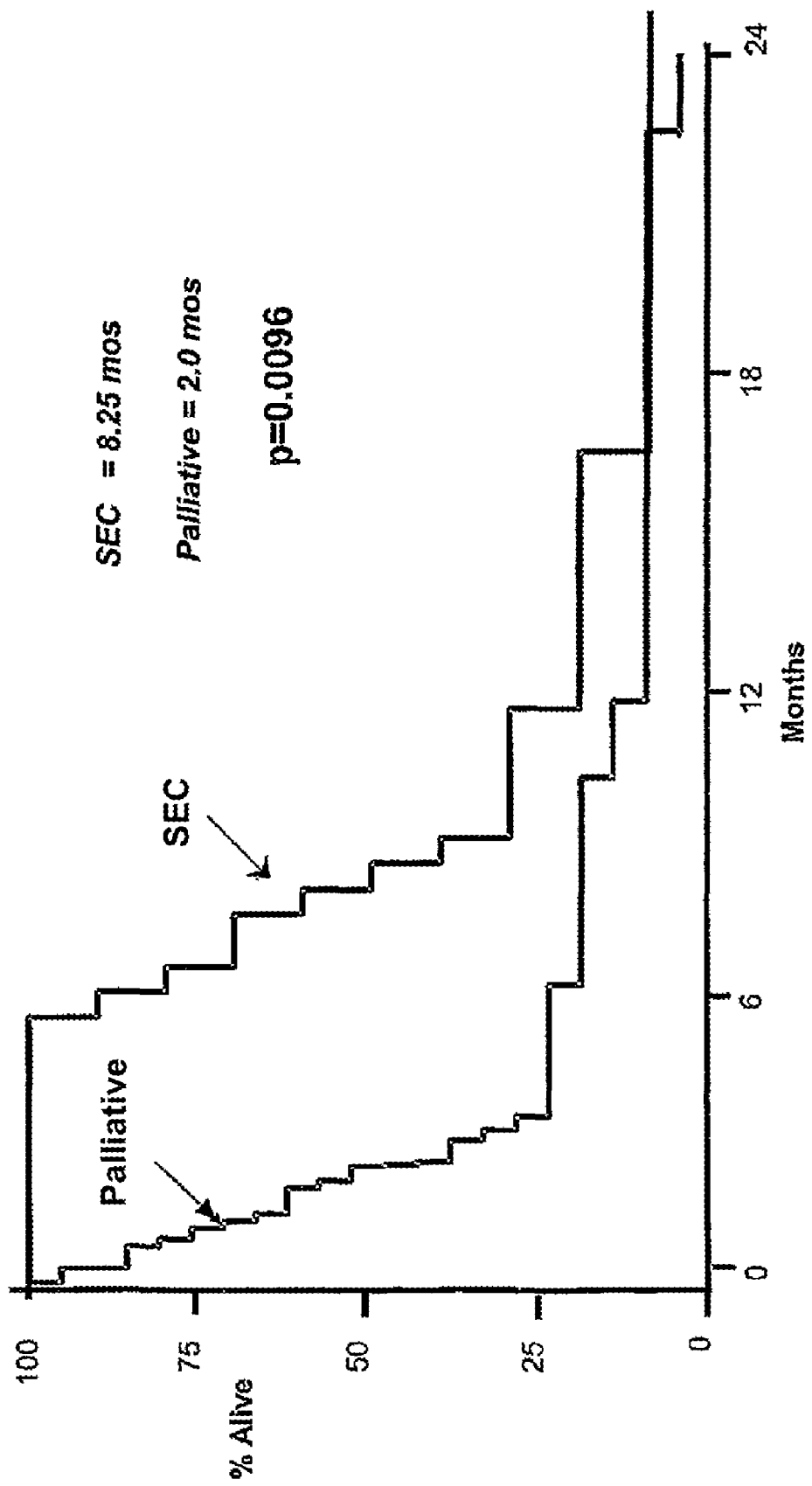
FIG. 1 shows Kaplan-Meir survival curve of the SEC-treated group compared to current historic control group of 21 patients with MPE from NSCLC treated at UCSD from 1993-1998 with talc insufflation showing a significantly prolonged survival in the SEC-treated group compared to the control group (p=0.0096).

The SAgs disclosed herein are prepared by either biochemical isolation, or, preferably by recombinant methods. The following SAgs, including their sequences and biological activities have been known for a number of years. Studies of these SAgs are found throughout the biomedical literature. For, biochemical and recombinant preparation of these SAgs, see the following references: Borst, D W et al., *Infect. Immun.* 61: 5421-5425 (1993); Couch, J L et al., *J. Bacteriol.* 170: 2954-2960 (1988); Jones, C L et al., *J. Bacteriol.* 166: 29-33 (1986); Bayles K W et al., *J. Bacteriol.* 171: 4799-4806 (1989); Blomster-Hautamaa, D A et al., *J. Biol. Chem.* 261: 15783-15786 (1986); Johnson, L P et al., *Mol. Gen. Genet.* 203, 354-356 (1986); Bohach G A et al., *Infect. Immun.* 55: 428-433 (1987); Iandolo J J et al., *Methods Enzymol* 165:43-52 (1988); Spero L et al., *Methods Enzymol* 78(Pt A):331-6 (1981); Blomster-Hautamaa D A, *Methods Enzymol* 165: 37-43 (1988); Iandolo J J Ann. Rev. Microbiol. 43: 375-402 (1989); U.S. Pat. No. 6,126,945 and U.S. provisional patent application 60/389,366 filed Jun. 15, 2002. These references and the references cited therein are hereby incorporated by reference in their entirety.

These SAgs are Staphylococcal enterotoxin A (SEA), Staphylococcal enterotoxin B (SEB), Staphylococcal enterotoxin C (SEC—actually three different proteins, SEC1, SEC2 and SEC3)), Staphylococcal enterotoxin D (SED), Staphylococcal enterotoxin E (SEE) and toxic shock syndrome toxin-1 (TSST-1) (U.S. Pat. No. 6,126,945 and U.S. provisional patent application 60/389,366 filed Jun. 15, 2002, and the references cited therein). The amino acids sequences of the above group of native (wild-type) SAgs is provided below:

```
                                                              [SEQ ID NO: 1]
SEA (Huang, I. Y. et al., J. Biol. Chem. 262:7006-7013 (1987))
   1 SEKSEEINEK DLRKKSELQG TAGNKQIY YYNEKAKTEN KESHDQFLQH TILFKGFFTD
  61 HSWYNDLLVD FDSKDIVDKY KGKKVDLYGA YYGYQCAGGT PNKTACMYGG VTLHDNNRLT
 121 EEKKVPINLW LDGKQNTVPL ETVKTNKKNV TVQELDLQAR RYLQEKYNLY NSDVFDGKVQ
 181 RGLIVFHTST EPSVNYDLFG AQGQYSNTLL RIYRDNKSIN SENMHIDIYL YTS

[SEQ ID NO: 2]
SEB (Papageorgiou, A. C. et al. J. Mol. Biol. 277:61-79 (1998))
   1 ESQPDPKPDE LHKSSKFTGL MENMKVLYDD NHVSAINVKS IDQFLYFDLI YSIKDTKLGN
  61 YDNVRVEFKN KDLADKYKDK YVDVFGANYY YQCYFSKKTN DINSHQTDKR KTCMYGGVTE
 121 HNGNQLDKYR SITVRVFEDG KNLLSFDVQT NKKKVTAQEL DYLTRHYLVK NKKLYEFNNS
 181 PYETGYIKFI ENENSFWYDM MPAPGDKFDQ SKYLMMYNDN KMVDSKDVKI EVYLTTKK

[SEQ ID NO: 3]
SEC1 (Bohach, G. A. et al., Mol. Gen. Genet. 209:15-20 (1987))
   1 MNKSRFISCV ILIFALILVL FTPNVLAESQ PDPTPDELHK ASKFTGLMEN MKVLYDDHYV
  61 SATKVKSVDK FLAHDLIYNI SDKKLKNYDK VKTELLNEGL AKKYKDEVVD VYGSNYYVNC
 121 YFSSKDNVGK VTGGKTCMYG GITKHEGNHF DNGNLQNVLI RVYENKRNTI SFEVQTDKKS
 181 VTAQELDIKA RNFLINKKNL YEFNSSPYET GYIKFIENNG NTFWYDMMPA PGDKFDQSKY

[SEQ ID NO: 4]
SEC2 (Papageorgiou, A. C., et al., Structure 3:769-779 (1995))
   1 ESQPDPTPDE LHKSSEFTGT MGNMKYLYDD HYVSATKVMS VDKFLAHDLI YNISDKKLKN
  61 YDKVKTELLN EDLAKKYKDE VVDVYGSNYY VNCYFSSKDN VGKVTGGKTC MYGGITKHEG
 121 NHFDNGNLQN VLIRVYENKR NTISFEVQTD KKSVTAQELD IKARNFLINK KMLYEFNSSP
 181 YETGYIKFIE NNGNTFWYDM MPAPGDKFDQ SKYLMMYNDN KTVDSKSVKI EVHLTTKNG

[SEQ ID NO: 5]
SEC3 (Hovde, C. J. et al., Mol. Gen. Genet. 220:329-333 (1990))
   1 MYKRLFISRV ILIFALILVI STPNVLAESQ PDPMPDDLHK SSEFTGTMGN MKYLYDDHYV
  61 SATKVKSVDK FLAHDLIYNI SDKKLKNYDK VKTELLNEDL AKKYKDEVVD VYGSNYYVNC
 121 YFSSKDNVGK VTGGKTCMYG GITKHEGNHF DNGNLQNVLV RVYENKRNTI SFEVQTDKKS
 181 VTAQELDIKA RNFLINKKNL YEFNSSPYET GYIKFIENNG NTFWYDMMPA PGDKFDQSKY
 241 LMMYNDNKTV DSKSVKIEVH LTTKNG
```

-continued

[SEQ ID NO: 6]
SED (Bayles, K. W. et al., J. Bacteriol. 171:4799-4806 (1989))
```
  1 MKKFNILIAL LFFTSLVISP LNVKANENID SVKEKELHKK SELSSTALNN MKHSYADKNP
 61 IIGENKSTGD QFLENTLLYK KFFTDLINFE DLLINFNSKE MAQHFKSKNV DVYPIRYSIN
121 CYGGEIDRTA CTYGGVTPHE GNKLKERKKI PINLWINGVQ KEVSLDKVQT DKKNVTVQEL
181 DAQARRYLQK DLKLYNNDTL GGKIQRGKIE FDSSDGSKVS YDLFDVKGDF PEKQLRIYSD
241 NKTLSTEHLH IDIYLYEK
```

[SEQ ID NO: 7]
SEE (Couch, J. L. et al, J. Bacteriol. 170:2954-2960 (1988))
```
  1 MKKTAFILLL FIALTLTTSP LVNGSEKSEE INEKDLRKKS ELQRNALSNL RQIYYYNEKA
 61 ITENKESDDQ FLENTLLFKG FFTGHPWYND LLVDLGSKDA TNKYKGKKVD LYGAYYGYQC
121 AGGTPNKTAC MYGGVTLHDN NRLTEEKKVP INLWIDGKQT TVPIDKVKTS KKEVTVQELD
181 LQARHYLHGK FGLYNSDSFG GKVQRGLIVF HSSEGSTVSY DLFDAQGQYP DTLLRIYRDN
241 KTINSENLHI DLYLYTT
```

[SEQ ID NO: 8]
TSST-1 (Prasad, G. S. et al., Protein Sci. 6:1220-1227 (1997))
```
  1 MNKKLLMNFF IVSPLLLATT ATDFTPVPLS SNQIIKTAKA STNDNIKDLL DWYSSGSDTF
 61 TNSEVLDNSL GSMRIKNTDG SISLIIFPSP YYSPAFTKGE KVDLNTKRTK KSQHTSEGTY
121 IHFQISGVTN TEKLPTPIEL PLKVKVHGKD SPLKYGPKFD KKQLAISTLD FEIRHQLTQI
181 HGLYRSSDKT GGYWKITMND GSTYQSDLSK KFEYNTEKPP INIDEIKTIE AEIN
```

The sections which follow discuss SAgs which have been discovered and characterized more recently.

Staphylococcal Enterotoxins SEG, SEH, SEI, SEJ, SEK, SEL, SEM

New Staphylococcal enterotoxins G, H, I, J, K, L and M (SEG, SEH, SEL, SEJ, SEK, SEL, SEM; abbreviated below as "SEG-SEM") were described in Jarraud, S. et al., J. Immunol. 166: 669-677 (2001); Jarraud S et al., J. Clin. Microbiol. 37: 2446-2449 (1999) and Munson, S H et al., Infect. Immun. 66:3337-3345 (1998). SEG-SEM show SAgic activity and are capable of inducing tumoricidal effects. The homology of these SE's to the better known SE's in the family ranges from 27-64%. Each induces selective expansion of TCR Vβ subsets Thus, these SEs retain the characteristics of T cell activation and Vβ usage common to all the other SE's.

SEG and SEH of this group and other enterotoxins including SPEA, SPEC, SPEG, SPEH, SME-Z, SME-$Z_2$, (see below) utilize zinc as part of high affinity MHC class II receptor. Amino acid substitution(s) at the high-affinity, zinc-dependent class II binding site are created to reduce their affinity for MHC class II molecules.

Jarraud S et al., 2001, supra, discloses methods used to identify and characterize SEG-SEM, and for cloning and recombinant expression of these proteins. These investigators have used a number of TCR-specific mAbs (Vβ specificity indicated in brackets) for flow cytometric analysis: E2.2E7.2 (Vβ2), LE89 (Vβ3), IMMU157 (Vβ5.1), 3D11 (Vβ5.3), CRI304.3 (Vβ6.2), 3G5D15 (Vβ7), 56C5.2 (Vβ8.1/8.2), FIN9 (Vβ9), C21 (Vβü 1), S511 (Vβ12), IMMU1222 (Vβ13.1), JIJ74 (Vβ13.6), CAS1.1.13 (Vβ14), Tamayal.2 (Vβ16), E17.5F3 (Vβ17), βA62.6 (Vβ18), ELL1.4 (Vβ20), IG125 (Vβ21.3), IMMU546 (Vβ22), and HUT78.1 (Vβ23).

Jarraud S et al., 2001, supra, indicates that the seven genes and pseudogenes composing the egc (enterotoxin gene cluster) operon are co-transcribed. The association of related co-transcribed genes suggested that the resulting peptides might have complementary effects on the host's immune response. One hypothesis was that gene recombination created new SE variants differing by their SAg activity profiles. Purified recombinant SEL, SEM, SEI, SEK, and SEGL29P (a mutant of SEL) were expressed in E. coli and analyzed. Recombinant SEL SEM, SEL and SEK consistently induced selective expansion of distinct subpopulations of T cells expressing particular Vβ genes. By contrast. SEGL29P failed to trigger expansion of any of 23 Vβ subsets, and the L29P mutation accounted for the complete loss of SAg activity (although this mutation did not induce a major conformational change). It is believed that this substitution mutation located at a position crucial for proper SAg/MHC II interaction.

Flow cytometry revealed preferential expansion of CD4 T cells in SEI and SEM cultures. By contrast, the CD4/CD8 ratios in SEK-, SEL-, and SEG-stimulated T cell lines were close to those in fresh PBL. Overall, TCR repertoire analysis confirm the SAgic nature of SEG-SEM.

The amino acid sequences of SEG-SEM are shown below

[SEQ ID NO: 9]
SEG (Baba, T. et al., Lancet 359, 1819-1827 (2002))
```
  1 MNKIFRVLTV SLFFFTFLIK NNLAYADVGV INLRNFYANY QPEKLQGVSS GNFSTSHQLE
 61 YIDGKYTLYS QFHNEYEAKR LKDHKVDIFG ISYSGLCNTK YMYGGITLAN QNLDKPRNIP
121 INLWVNGKQN TISTDKVSTQ KKBVTAQEID IKLRKYLQNE YNIYGFNKTK KGQEYGYKSK
181 FNSGFNKGKI TFHLNNEPSF TYDLFYTGTG QAESFLKIYN DNKTIDAENF HLDVEISYEK
241 TE
```

[SEQ ID NO: 10]
SEH (Omoe, K. et al., J. Clin. Microbiol. 40: 857-862 (2002))
```
  1 EDLHDKSELT DLALANAYGQ YNHPFIKENI KSDEISGEKD LIFRNQGDSG NDLRVKFATA
 61 DLAQKFKNKN VDIYGASFYY KCEKISENIS ECLYGGTTLN SEKLAQERVI GANVWVDGIQ
121 KETELIRTNK KNVTLQELDI KIRKILSDKY KIYYKDSEIS KGLIEFDMKT PRDYSFDIYD
181 LKGENDYEID KIYEDNKTLK SDDISHIDVN LYTKKKV
```

-continued

[SEQ ID NO: 11]
SEI (Kuroda, M. et al., Lancet 357 (9264), 1225-1240 (2001))
```
  1 MKKFKYSFIL VFILLFNIKD LTYAQGDIGV GNLRNFYTKH DYIDLKGVTD KNLPIANQLE
 61 FSTGTNDLIS ESNNWDEISK FKGKKLDIFG IDYNGPCKSK YMYGGATLSG QYLNSARKIP
121 INLWVNGKHK TISTDKIATN KKLVTAQEID VKLRRYLQEE YNIYGHNNTG KGKEYGYKSK
181 FYSGFNNGKV LFHLNNEKSF SYDLFYTGDG LPVSFLKIYE DNKIIESEKF HLDVEISYVD
241 SN
```

[SEQ ID NO: 12]
SEJ (Zhang, S. et al., FEMS Microbiol. Lett. 168:227-233 (1998))
```
  1 MKKTIPILIF SLTLTLLITP LVYSDSKNET IKEKNLHKKS ELSSITLNNL RHIYFFNEKG
 61 ISEKIMTEDQ FLDYTLLFKS FFISHSQYND LLVQFDSKET VNKFKGKQVD LYGSYYGFQC
121 SGGKPNKTAC MYGGVTLHEN NQLYDTKKIP INLWIDSIRT VVPLDIVKTN KKKVTIQELD
181 LQARYYLHKQ YNLYNPSTFD GKIQKGLIVF HTSKEPLVSY DLFNVIGQYP DKLLKIYQDN
241 KIIESENMHI DIYLYTSLIV LISLPLVL
```

[SEQ ID NO: 13]
SEK (Baba, T., et al., Lancet 359, 1819-1827 (2002))
```
  1 MKKLISILLI NIIILGVSNN ASAQGDIGID NLRNFYTKKD FINLKDVKDN DTPIANQLQF
 61 SNESYDLISE SKDFNKFSNF KGKKLDVFGI SYNGQCNTKY TYGGITATNE YLDKPRNIPI
121 NIWINGNHKT ISTNKVSTNK KFVTAQEIDI KLRRYLQEEY NIYGHNGTKK GEEYGHKSKF
181 YSGFNIGKVT FHLNNNDTFS YDLFYTGDDG LPKSFLKIYE DNKTVESEKF HLDVDISYKE
241 TK
```

[SEQ ID NO: 14]
SEL (Kuroda, M. et al., Lancet 357, 1225-1240 (2001))
```
  1 MKKRLLFVIV ITLFIFSSNH TVLSNGDVGP GNLRNFYTKY EYVNLKNVKD KNSPESHRLE
 61 YSYKNDTLYA EFDNEYITSD LKGKNVDVFG ISYKYGSNSR TIYGGVTKAE NNKLDSPRII
121 PINLIINGKH QTVTTKSVST DKKMVTAQEI DVKLRKYLQD EFNIYGHNDT GKGKEYGTSS
181 KFYSGFDKGS VVFEMNDGSN FSYDLFYTGY GLPESFLKIY KDNKTVDSTQ FHLDVEISKR
```

[SEQ ID NO: 15]
SEM (Kuroda, M. et al., Lancet 357, 1225-1240 (2001))
```
  1 MKRILIIVVL LFCYSQNHIA TADVGVLNLR NYYGSYPIED HQSINPENNH LSHQLVFSMD
 61 NSTVTAEFKN VDDVKKFKNH AVDVYGLSYS GYCLKNKYIY GGVTLAGDYL EKSRRIPINL
121 WVNGEHQTIS TDKVSTNKKL VTAQEIDTKL RRYLQEEYNI YGFNDTNKGR NYGNKSKFSS
181 GFNAGKILFH LNDGSSFSYD LFDTGTGQAE SFLKIYNDNK TVETEKFHLD VEISYKDES
```

Streptococcal Pyrogenic Exotoxins (SpEs)

The SpE's SPEA, SPEB, SPEC, SPEG, SPEH, SME-Z, SME-$Z_2$ and SSA are SAgs induce tumoricidal effects. SPEA, SPEB, SPEC have been known for some time and their structures and biological activities described in numerous publications.

SPEG, SPEH, and SPEJ genes were identified from the *Streptococcus pyogenes* M1 genomic database and described in detail in Proft, T et al., *J. Exp. Med.* 189: 89-101 (1999) which also describes SMEZ, SMEZ-2. This document also describes the cloning and expression of the genes encoding these proteins.

The smez-2 gene was isolated from the *S. pyogenes* strain 2035, based on sequence homology to the stre

```
                                                             [SEQ ID NO: 16]
SPEA (Papageorgiou, A. C. et al. EMBO J. 18:9-21 (1999))
  1 MENNKKVLKK MVFFVLVTFL GLTISQEVFA QQDPDPSQLH RSSLVKNLQN IYFLYEGDPV

61 THENVKSVDQ LLSHDLIYNV SGPNYDKLKT ELKNQEMATL FKDKNVDIYG VEYYHLCYLC

121 ENAERSACIY GGVTNHEGNH LEIPKKIVVK VSIDGIQSLS FDIETNKKMV TAQELDYKVR

181 KYLTDNKQLY TNGPSKYETG YIKFIPKNKE SFWFDFFPEP EFTQSKYLMI YKDNETLDSN

241 TSQIEVYLTT K
```

*Streptococcus* Pyrogenic Exotoxin B (SPEB)

Purification of native SpEB is described by Gubba, S. et al., *Infect. Immun.* 66: 765-770 (1998). Expression and purification of recombinant SpEB are also described in this reference. The native SPEB sequence is shown below (Kapur, V. et al., *Microb. Pathog.* 15:327-346 (1993)):

```
                                                             [SEQ ID NO: 17]
  1 MNKKKLGIRL LSLLALGGFV LANPVFADQN FARNEKEAKD SAITFIQKSA AIKAGARSAE

61 DIKLDKVNLG GELSGSNMYV YNISTGGFVI VSGDKRSPEI LGYSTSGSFD ANGKENIASF

121 MESYVEQIKE NKKLDTTYAG TAEIKQPVVK SLLDSKGIHY NQGNPYNLLT PVIEKVKPGE

181 QSFVGQHAAT GCVATATAQI MKYHNYPNKG LKDYTYTLSS NNPYFNHPKN LFAAISTRQY

241 NWNNILPTYS GRESNVQKMA ISELMADVGI SVDMDYGPSS GSAGSSRVQR ALKENFGYNQ

301 SVHQINRSDF SKQDWEAQID KELSQNQPVY YQGVGKVGGH AFVIDGADGR NFYHVNWGWG

361 GVSDGFFRLD ALNPSALGTG GGAGGFNGYQ SAVVGIKP
```

*Streptococcus* Pyrogenic Exotoxin C(SPEC)

Methods of isolation and characterization of SPEC is carried out by the methods of Li, P L et al., *J. Exp. Med.* 186: 375-383 (1997). These references also describe T cell proliferation stimulated by this SAg and the analysis of its selectivity for TCR Vβ regions. The native sequence of SPEC (Kapur, V. et al., *Infect. Immun.* 60:3513-3517 (1992) is shown below:)

```
                                                             [SEQ ID NO: 18]
  1 MKKINIIKIV FTITVILIST ISPIIKSDSK KDISNVKSDL LYAYTITPYD YKDCRVNFST

61 THTLNIDTQK YRGKDYYISS EMSYEASQKF KRDDHVDVFG LFYILNSHTG EYIYGGITPA

121 QNNKVNHKLL GNLFISGESQ QNLNNKIILE KDIVTFQEID FKIRKYLMDN YKIYDATSPY

181 VSGRIEIGTK DGKHEQIDLF DSPNEGTRSD IFAKYKDNRI INMKNFSHFD IYLE
```

Streptococcal Superantigen (SSA)

SSA is an ~28-kDa SAg protein isolated from culture supernatants as described by Moflick J et al., *J. Clin. Invest.* 92: 710-719 (1993) and Reda K et al., *Infect. Immun.* 62: 1867-1874 (1994). SSA stimulates proliferation of human T cells bearing Vβ1, Vβ3, Vβ5.2, and Vβ15 in an MHC class II-dependent manner. The first 24 amino acid residues of SSA are be 62.5% identical to SEB, SEC1, and SEC3. Purification and cloning of SSA is described in Reda K et al., *Infect. Immun.* 62: 1867-1874 (1994). The native sequence of SSA (Reda, K. B. et al., *Infect. Immun.* 64: 1161-1165 (1996)) is shown below:

```
                                                        [SEQ ID NO: 19]
  1 MNKRIRILVV ACVVFCAQLL SISVFASSQP DPTPEQLNKS SQFTGVMGUL RCLYDNHFVE

61 GTNVRSTGQL LQHDLIFPIK DLKLKNYDSV KTEFNSKDLA AKYKNKDVDI FGSNYYYHCY

121 YSEGNSCKNA KKTCMYGGVT EEHRNQIEGK FPNITVKVYE DNENILSFDI TTNKKQVTVQ

181 ELDCKTRKIL VSRKNLYEFN NSPYETGYIK FIESSGDSFW YDMMPAPGAI FDQSKYLMLY

241 NDNKTVSSSA IAIEVHLTKK
```

Streptococcal Pyrogenic Exotoxins G and H and SMEZ

The sequences of the more recently discovered Streptococcal exotoxin SAgs are provided below:

```
                                                        [SEQ ID NO: 20]
SPEG (Fraser, J et al., Mol Med Today 6:125-32 (2000))
  1 DENLKDLKRS LRFAYNITPC DYENVEIAFV TTNSIHINTK QKRSECILYV DSIVSLGITD
 61 QFIKGDKVDV FGLPYNFSPP YVDNIYGGIV KHSNQGNKSL QFVGILNQDG KETYLPSEVV
121 RIKKKQFTLQ EFDFKIRKFL MEKYNIYDSE SRYTSGSLFL ATKDSKHYEV DLFNKDDKLL
181 SRDSFFKRYK DNKIFNSEEI SHFDIYLKTY
```

```
                                                        [SEQ ID NO: 21]
SPEH (Proft, T. et al., J. Exp. Med. 189:89-102 (1999))
  1 MRYNCRYSHI DKKIYSMIIC LSFLLYSNVV QANSYNTTNR HNLESLYKHD SNLIEADSIK
 61 NSPDIVTSHM LKYSVKDKNL SVFFEKDWIS QEFKDKEVDI YALSAQEVCE CPGKRYEAFG
121 GITLTNSEKK EIKVPVNVWD KSKQQPPMFI TVNKPKVTAQ EVDIKVRKLL IKKYDIYNNR
181 EQKYSKGTVT LDLNSGKDIV FDLYYFGNGD FNSMLKIYSN NERIDSTQFH VDVSIS
```

```
                                                        [SEQ ID NO: 22]
SMEZ (Proft, T. et al., J. Exp. Med. 191:1765-1776 (2000))
  1 LEVDNNSLLR NIYSTIVYEY SDTVIDFKTS HNLVTKKLDV RDARDFFINS EMDEYAANDF
 61 KAGDKIAVFS VPFDWNYLSK GKVTAYTYGG ITPYQKTSIP KNIPVNLWIN RKQIPVPYNQ
121 ISTNKTTVTA QEIDLKVRKF LTAQHQLYSS GSSYKSGKLV FHTNDNSDKY SLDLFYTGYR
181 DKESIFKVYK DNKSFNIDKI GHLDIEIDS
```

*Yersinia pseudotuberculosis* Mitogen (Superantigen) (YPM)

Cloning, expression and purification of YPM is described by Miyoshi-Akiyama, T. et al., *J. Immunol.* 154: 5228-5234 (1995).

The above reference described assays of YPM using lymphoid cells and murine L cells transfected with human HLA genes, including T cell proliferation and cytokine (IL2) secretion. The sequence of YPM is shown below

[SEQ ID NO: 23]
(Carnoy, C. et al., J. Bacteriol. 184 (16), 4489-4499 (2002)):

```
  1 MKKKFLSLLT LTFFSGLALA ADYDNTLNSI PSLRIPNIET YTGTIQGKGE VCIRGNKEGK

61 SRGGELYAVL RSTNANADMT LILLCSIRDG WKEVKRSDID RPLRYEDYYT PGALSWIWEI

121 KNNSSEASDY SLSATVHDDK EDSDVLMKCP
```

Staphylococcal Exotoxin like Proteins (SET)

The identification characterization of the SETs (SET-1 and SET-2) and the cloning and purification of SET-1 is described in Williams, R. J. et al., *Infect. Immun.* 68: 4407-4414 (2000). This reference discloses the distribution of the set1 gene among Staphylococcal species and strains.

The set1 nucleotide sequences are deposited in the GenBank database under accession numbers AF094826 (set gene cluster fragment), AF188835 (NCTC 6571 set1 gene), AF188836 (FRI326 set1 gene), and AF188837 (NCTC 8325-4 set1 gene). Recombinant SET-1 protein stimulates production of the proinflammatory cytokines IL-1, IL-6, and TNFα

Preferred Form of Superantigen for Therapeutic Use

A preferred construct for intrathecal and intrapleural use comprises a SAg in native form. In contrast, for systemic use the preferred SAg is one to which humans do not make or make only marginal amounts neutralizing antibody fused recombinantly or biochemically to a high affinity tumor specific antibody, Fab or single chain Fv. To this end, SAg epitopes in the conjugate which bind endogenous (to include preexisting) SAg specific antibodies are deleted and/or substituted by alanine or amino acid sequences to which the host does not have preexisting antibodies. For example, a dominant epitope on SEB recognized by anti-SEB antibodies is the sequence 225-234 (Nishi et al., *J. Immunol.* 158: 247-254 (1997) and an epitope on SEA recognized by anti-SEA antibodies is the sequence 121-149 (Hobieka et al., *Biochem. Biophys. Res. Comm.* 223: 565-571 (1996). Alternatively, SAgs such as *Y. pseudotuberculosis* or *C. perfringens* toxin A or to which humans do not have preexisting antibodies are used. *Y. pseudotuberculosis* SAg has, in addition, a natural RGD domain which has tumor-localizing properties.

Functional Homologues and Derivatives of Superantigen Proteins of Peptides

The present invention contemplates, in addition to native SAgs, the use of homologues of native SAgs that have the requisite biological activity to be useful in accordance with the invention.

Thus, in addition to native SAg protein and nucleic acid compositions described herein, the present invention encompasses functional derivatives, among which homologues are preferred. Thus, biologically active homologues of staphylococcal enterotoxins, streptococcal exotoxins. *Y. pseudotuberculosis* SAg YPM, *C. perfringens* toxin A, *M. arthritides* SAgs are included herein.

By "functional derivative" is meant a "fragment," "variant," "mutant," "homologue," "analogue," or "chemical derivative". Homologues include fusion proteins, chimeric proteins and conjugates that include a SAg portion fused to or conjugated to a fusion partner polypeptide or peptide. A functional derivative retains at least a portion of the biological activity of the native protein which permits its utility in accordance with the present invention. Such biological activity includes stimulation of T cell proliferation and/or cytokine secretion, stimulation of T cell-mediated cytotoxic activity, as a result of interactions of the SAg composition with T cells preferably via the TCR Vβ region.

A "fragment" refers to any shorter peptide. A "variant" of refers to a molecule substantially similar to either the entire protein or a peptide fragment thereof. Variant peptides may be conveniently prepared by direct chemical synthesis of the variant peptide, using methods well-known in the art.

A homologue refers to a natural protein, encoded by a DNA molecule from the same or a different species. Homologues, as used herein, typically share at least about 50% sequence similarity at the DNA level or at least about 18% sequence similarity at the amino acid level, with a native protein.

An "analogue" refers to a non-natural molecule substantially similar to either the entire molecule or a fragment thereof A "chemical derivative" contains additional chemical moieties not normally a part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues.

A fusion protein comprises a native SAg, a fragment or a homologue fused by recombinant means to another polypeptide fusion partner, optionally including a spacer between the two sequences. Preferred fusion partners are antibodies, Fab fragments, single chain Fv fragments. Other fusion partners are any peptidic receptor ligand, cytokine, extracellular domain ("ECD") of a costimulatory molecule and the like.

The recognition that the biologically active regions of the SEs, for example, are substantially homologous, i.e., that the sequences are substantially similar, enables prediction of the sequences of synthetic peptides which will exhibit similar biological effects in accordance with this invention (Johnson, L. P. et al., *Mol. Gen. Genet.* 203:354-356 (1986).

The following terms are used in the disclosure of sequences and sequence relationships between two or more nucleic acids or polypeptides: (a) "reference sequence", (b) "comparison window", (c) "sequence identity", (d) "percentage of sequence identity", and (e) "substantial identity"

As used herein, "reference sequence" is a defined sequence used as a basis for sequence comparison. A reference sequence may be a subset or the entirety of a specified sequence; for example, as a segment of a full-length cDNA or other polynucleotide sequence, or the complete cDNA or polynucleotide sequence. The same is the case for polypeptides and their amino acid sequences.

As used herein, "comparison window" includes reference to a contiguous and specified segment of a polynucleotide or amino acid sequence, wherein the sequence may be compared to a reference sequence and wherein the portion of the sequence in the comparison window may comprise additions or deletions (i.e., gaps) compared to the reference sequence (which does not comprise additions or deletions) for optimal alignment of the two sequences. Generally, the comparison window is at least 20 contiguous nucleotides or amino acids in length, and optionally can be 30, 40, 50, 100, or longer. Those of skill in the art understand that to avoid a high similarity to a reference sequence due to inclusion of gaps in the sequence a gap penalty is typically introduced and is subtracted from the number of matches.

Methods of alignment of nucleotide and amino acid sequences for comparison are well-known in the art. For comparison, optimal alignment of sequences may be done using any suitable algorithm, of which the following are examples:

(a) the local homology algorithm ("Best Fit") of Smith and Waterman, *Adv. Appl. Math.* 2: 482 (1981);

(b) the homology alignment algorithm (GAP) of Needleman and Wunsch, *J. Mol. Biol.* 48: 443 (1970); or (c) a search for similarity method (FASTA and TFASTA) of Pearson and Lipman, *Proc. Natl. Acad. Sci.* 85 2444 (1988);

In a preferred method of alignment, Cys residues are aligned. Computerized implementations of these algorithms, include, but are not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG) (Madison, Wis.). The CLUSTAL program is described by Higgins et al., *Gene* 73:237-244 (1988); Higgins et al., *CABIOS* 5:151-153 (1989); Corpet et al., *Nuc Acids Res* 16:881-90 (1988); Huang et al., *CABIOS* 8:155-65 (1992), and Pearson et al., *Methods in Molecular Biology* 24:307-331 (1994).

A preferred program for optimal global alignment of multiple sequences is PileUp (Feng and Doolittle, *J Mol Evol* 25:351-360 (1987) which is similar to the method described by Higgins et al. 1989, supra).

The BLAST family of programs which can be used for database similarity searches includes: NBLAST for nucleotide query sequences against database nucleotide sequences; XBLAST for nucleotide query sequences against database protein sequences; BLASTP for protein query sequences against database protein sequences; TBLASTN for protein query sequences against database nucleotide sequences; and TBLASTX for nucleotide query sequences against database nucleotide sequences. See, for example, Ausubel et al., eds., *Current Protocols in Molecular Biology*, Chapter 19, Greene Publishing and Wiley-Interscience, New York (1995) or most recent edition. Unless otherwise stated, stated sequence identity/similarity values provided herein, typically in percentages, are derived using the BLAST 2.0 suite of programs (or updates thereof) using default parameters. Altschul et al., *Nuc Acids Res.* 25:3389-3402 (1997).

As is known in the art, BLAST searches assume that proteins can be modeled as random sequences. However, many real proteins comprise regions of nonrandom sequence which may include homopolymeric tracts, short-period repeats, or regions rich in particular amino acids. Alignment of such regions of "low-complexity" regions between unrelated proteins may be performed even though other regions are entirely dissimilar. A number of low-complexity filter programs are known that reduce such low-complexity alignments. For example, the SEG (Wooten et al., *Comput. Chem.* 17:149-163 (1993)) and XNU (Clayerie et al., *Comput. Chem,* 17:191-201 (1993)) low-complexity filters can be employed alone or in combination.

As used herein, "sequence identity" or "identity" in the context of two nucleic acid or amino acid sequences refers to the residues in the two sequences which are the same when aligned for maximum correspondence over a specified comparison window. It is recognized that when using percentages of sequence identity for proteins, a residue position which is not identical often differs by a conservative amino acid substitution, where a substituting residue has similar chemical properties (e.g., charge, hydrophobicity, etc.) and therefore does not change the functional properties of the polypeptide. Where sequences differ in conservative substitutions, the % sequence identity may be adjusted upwards to correct for the conservative nature of the substitution, and be expressed as "sequence similarity" or "similarity" (combination of identity and differences that are conservative substitutions). Means for making this adjustment are well-known in the art. Typically this involves scoring a conservative substitution as a partial rather than as a full mismatch, thereby increasing the percentage sequence identity. Thus, for example, where an identical amino acid is given a score of "1" and a non-conservative substitution is given a score of "0" zero, a conservative substitution is given a score between 0 and 1. The scoring of conservative substitutions is calculated, e.g., according to the algorithm of Meyers et al., *CABIOS* 4:11-17 (1988) as implemented in the program PC/GENE (Intelligenetics, Mountain View, Calif., USA).

As used herein, "percentage of sequence identity" refers to a value determined by comparing two optimally aligned sequences over a comparison window, wherein the portion of the nucleotide or amino acid sequence in the comparison window may comprise additions or deletions (i.e., gaps) as compared to the reference sequence (which lacks such additions or deletions) for optimal alignment, such as by the GAP algorithm (supra). The percentage is calculated by determining the number of positions at which the identical nucleotide or amino acid residue occurs in both sequences to yield the number of matched positions, dividing that number by the total number of positions in the window of comparison and multiplying the result by 100, thereby calculating the percentage of sequence identity.

The term "substantial identity" of two sequences means that a polynucleotide or polypeptide comprises a sequence that has at least 60%, preferably at least 70%, more preferably at least 80%, even more preferably at least 90%, and most preferably at least 95% sequence identity to a reference sequence using one of the alignment programs described herein using standard parameters. Values can be appropriately adjusted to determine corresponding identity of the proteins encoded by two nucleotide sequences by taking into account codon degeneracy, amino acid similarity, reading frame positioning, etc.

One indication that two nucleotide sequences are substantially identical is if they hybridize to one other under stringent conditions. Because of the degeneracy of the genetic code, a number of different nucleotide codons may encode the same amino acid. Hence, two given DNA sequences could encode the same polypeptide but not hybridize under stringent conditions. Another indication that two nucleic acid sequences are substantially identical is that the polypeptide encoded by the first nucleic acid is immunologically cross reactive with the polypeptide encoded by the second nucleic acid. Clearly, then, two peptide or polypeptide sequences are substantially identical if one is immunologically reactive with antibodies raised against the other. A first peptide is substantially identical to a second peptide, if they differ only by a conservative substitution. Peptides which are "substantially similar" share sequences as noted above except that nonidentical residue positions may differ by conservative substitutions.

Thus, in one embodiment of the present invention, the Lipman-Pearson FASTA or FASTP program packages (Pearson, W. R. et. al., 1988, supra; Lipman, D. J. et al, *Science* 227:1435-1441 (1985)) in any of its older or newer iterations may be used to determine sequence identity or homology of a given protein, preferably using the BLOSUM 50 or PAM 250 scoring matrix, gap penalties of −12 and −2 and the PIR or SwissPROT databases for comparison and analysis purposes. The results are expressed as z values or E ( ) values. To achieve a more "updated" z value cutoff for statistical significance, preferably corresponding to a z value>10 based on the increase in database size over that of 1988, in a FASTA analysis using the equivalent 2001 database, a significant z value would exceed 13.

A more widely used and preferred methodology determines the percent identity of two amino acid sequences or of two nucleic acid sequences after optimal alignment as discussed above, e.g., using BLAST. In a preferred embodiment of this approach, a polypeptide being analyzed for its homology with native SAg is at least 20%, preferably at least 40%, more preferably at least 50%, even more preferably at least 60%, and even more preferably at least 70%, 80%, or 90% as long as the reference sequence. The amino acid residues (or nucleotides) at corresponding positions are then compared. Amino acid or nucleic acid "identity" is equivalent to amino acid or nucleic acid "homology".

In a preferred comparison of a putative SAg homologue polypeptide and a native SAg protein, the percent identity between two amino acid sequences is determined using the Needleman and Wunsch alignment algorithm (incorporated into the GAP program in the GCG software package (available at the URL www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another embodiment, the percent identity between the encoding nucleotide sequences is determined using the GAP program in the GCG software package (also available at above URL), using a NWSgapdna.CMP matrix and a gap weight of 40, 50, 60, 70, or 80 and a length weight of 1, 2, 3, 4, 5, or 6. In another embodiment, the algorithm of Meyers et al., supra (incorporated into the ALIGN program, version 2.0), is implemented using a PAM120 weight residue table, a gap length penalty of 12 and a gap penalty of 4.

The wild-type (or native) SAg-encoding nucleic acid sequence or the SAg protein sequence can further be used as a "query sequence" to search against a public database, for example, to identify other family members or related sequences. Such searches can be performed using the NBLAST and XBLAST programs, supra (see Altschul et al (1990) *J. Mol. Biol.* 215:403-10). BLAST nucleotide searches can be performed with the NBLAST program, score=100, wordlength=12 to identify nucleotide sequences homologous to native SAgs. BLAST protein searches can be performed with the XBLAST program, score=50, wordlength=3 to identify amino acid sequences homologous to identify polypeptide molecules homologous to a native SAg. To obtain gapped alignments for comparison purposes, Gapped BLAST can be utilized as described in Altschul et al. (1997, supra). Default parameters of XBLAST and NBLAST can be found at the NCBI website (www.ncbi.nlm.nih.gov)

Using the FASTA programs and method of Pearson and Lipman, a preferred SAg homologue is one that has a z value >10. Expressed in terms of sequence identity or similarity, a preferred SAg homologue for use according the present invention has at least about 20% identity or 25% similarity to a native SAg. Preferred identity or similarity is higher. More preferably, the amino acid sequence of a homologue is substantially identical or substantially similar to a native SAg sequence as those terms are defined above.

One group of substitution variants (also homologues) are those in which at least one amino acid residue in the peptide molecule, and preferably, only one, has been removed and a different residue inserted in its place. For a detailed description of protein chemistry and structure, see Schulz, G. E. *Principles of Protein Structure* Springer-Verlag, New York, 1978, and Creighton, T. E., *Proteins: Structure and Molecular Properties*, W.H. Freeman & Co., San Francisco, 1983, which are hereby incorporated by reference. The types of substitutions which may be made in the protein or peptide molecule of the present invention may be based on analysis of the frequencies of amino acid changes between a homologous protein of different species, such as those presented in Table 1-2 of Schulz et al. (supra) and FIG. 3-9 of Creighton (supra). Based on such an analysis, conservative substitutions are defined herein as exchanges within one of the following five groups:
1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, kg, Lys;
4. Large aliphatic, nonpolar residues: Met, Leu, Ile, Val (Cys); and
5. Large aromatic residues: Phe, Tyr, Trp.

The three amino acid residues in parentheses above have special roles in protein architecture. Gly is the only residue lacking any side chain and thus imparts flexibility to the chain. Pro, because of its unusual geometry, tightly constrains the chain. Cys can participate in disulfide bond formation which is important in protein folding. Tyr, because of its hydrogen bonding potential, has some kinship with Ser, Thr, etc.

More substantial changes in functional or immunological properties are made by selecting substitutions that are less conservative, such as between, rather than within, the above five groups, which will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of such substitutions are (a) substitution of gly and/or pro by another amino acid or deletion or insertion of Gly or Pro; (b) substitution of a hydrophilic residue, e.g., Ser or Thr, for (or by) a hydrophobic residue, e.g., Leu, Ile, Phe, Val or Ala; (c) substitution of a Cys residue for (or by) any other residue; (d) substitution of a residue having an electropositive side chain, e.g., Lys, Arg or His, for (or by) a residue having an electronegative charge, e.g., Glu or Asp; or (e) substitution of a residue having a bulky side chain, e.g., Phe, for (or by) a residue not having such a side chain, e.g., Gly.

The deletions and insertions, and substitutions according to the present invention are those which do not produce radical changes in the characteristics of the protein or peptide molecule. However, when it is difficult to predict the exact effect of the substitution, deletion, or insertion in advance of doing so, one skilled in the art will appreciate that the effect will be evaluated by routine screening assays, for example direct or competitive immunoassay or biological assay of T cell function as described herein. Modifications of such proteins or peptide properties as redox or thermal stability, hydrophobicity, susceptibility to proteolytic degradation or the tendency to aggregate with carriers or into multimers are assessed by methods well known to the ordinarily skilled artisan.

Chemical Derivatives

Covalent modifications of the SAg proteins or peptide fragments thereof, preferably of SEs or peptide fragments thereof, are included herein. Such modifications may be introduced into the molecule by reacting targeted amino acid residues of the protein or peptide with an organic derivatizing agent that is capable of reacting with selected side chains or terminal residues. This may be accomplished before or after polymerization.

Cysteinyl residues most commonly are reacted with a-haloacetates (and corresponding amines), such as 2-chloroacetic acid or chloroacetamide, to give carboxymethyl or carboxyamidomethyl derivatives. Cysteinyl residues also are derivatized by reaction with bromotrifluoroacetone, α-bromo-(5-imidozoyl)propionic acid, chloroacetyl phosphate, N-alkylmaleimides, 3-nitro-2-pyridyldisulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing a-amino-containing residues include imidoesters such as methyl picolinimidate; pyridoxal phosphate; pyridoxal; chloroborohydride; trinitrobenzenesulfonic acid; 0-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pK of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form 0-acetyl tyrosyl species and 3-nitro derivatives, respectively.

Carboxyl side groups (aspartyl or glutamyl) are selectively modified by reaction with carbodiimides as noted above. Aspartyl and glutamyl residues are converted to asparaginyl and glutaminyl residues by reaction with ammonium ions.

Glutaminyl and asparaginyl residues may be deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the a-amino groups of lysine, arginine, and histidine side chains (T. E. Creighton, *Proteins: Structure and Molecule Properties*, W.H. Freeman & Co.,
San Francisco, pp. 79-86 (1983)), acetylation of the N-terminal amine, and, in some instances, amidation of the C-terminal carboxyl groups.

Such derivatized moieties may improve the solubility, absorption, biological half life, and the like. The moieties may alternatively eliminate or attenuate any undesirable side effect of the protein and the like. Moieties capable of mediating such effects are disclosed, for example, in *Remington's Pharmaceutical Sciences*, 16th ed., Mack Publishing Co., Easton, Pa. (1980).

Superantigen Homologues

The variants or homologues of native SAg proteins or peptides including mutants (substitution, deletion and addition types), fusion proteins (or conjugates) with other polypeptides, are characterized by substantial sequence homology to (a) the long-known SE's —SEA, SEB, $SEC_{1-3}$, SED, SEE and TSST-1;
(b) long-known SpE's;
(c) more recently discovered SE's (SEG, SEH, SEI, SEJ, SEK, SEL, SEM, SETs 1-5); or
(d) non-enterotoxin superantigens (YPM, *M. arthritides* superantigen).

Preferred homologues were disclosed above.

Table 1 below lists a number of native SEs and exemplary homologues (amino acid substitution, deletion and addition variants (mutants) and fragments) with z values>10 (range: z=16 to z=136) using the Lipman-Pearson algorithm and FASTA. These homologues also induce significant T lymphocyte mitogenic responses that are generally comparable to native SE's.

In addition, as shown in Table 2, several of these homologues also promote antigen-nonspecific T lymphocyte killing in vitro by a mechanism termed "superantigen-dependent cellular cytotoxicity" (SDCC) or, in the case of SAg-mAb fusion proteins, "superantigen/antibody dependent cellular cytotoxicity" (SADCC).

According to the present invention, other SE homologues (e.g., z>10 or, in another embodiment, having at least about 20% sequence identity or at least about 25% sequence similarity when compared to native SEs), exhibiting T lymphocyte mitogenicity, SDCC or SADCC, are useful anti-tumor agents when administered to a tumor bearing host via any intrathecal route.

Tumors in Sheaths Encasing Organs

The appearance of tumors in sheaths ("theca") encasing an organ often results in production and accumulation of large volumes of fluid in the organ's sheath. Examples include (1) pleural effusion due to fluid in the pleural sheath surrounding the lung, (2) ascites originating from fluid accumulating in the peritoneal membrane and (3) cerebral edema due to metastatic carcinomatosis of the meninges. Such effusions and fluid accumulations generally develop at an advanced stage of the disease.

Intrathecal Superantigens for Treatment of Malignant Ascites and Malignant Pleural Effusions The present invention contemplates the use of any SAg or SET in any form. This includes but is not limited to staphylococcal enterotoxins A, B, C, D, E, F, G H, I, J, K, L, M, SpE's, YPM, *M. arthritides* SAg, *C. perfringens* exotoxin for direct administration into cavities or spaces, e.g., peritoneum, thecal space, pericardial and pleural space containing tumor.

TABLE 1

SE-Homologues Induce T Lymphocyte Mitogenesis

| SE Homologue[a] | T Lymphocyte Mitogenic Response[b] ($EC_{50}$)[c] | Reference (SPECIES) |
|---|---|---|
| SEA (native) | 1 | Abrahmsen et al., EMBO J. 14: |
| SEA D227A | 1057 | 2978-2986 (1995); |
| SEA F47A | 52 | HUMAN |
| SEA H225A | 1272 | |
| SEA K123A/D132G | 2 | |
| SEA N128A | 2 | |
| SEA K55A | 1 | |
| SEA H50A | 4 | |
| SEA D45A | 1 | |
| SEA H187A | 11 | |
| SEA E191A/N195A | 1 | |
| SEA C96S | 12 | Grossman et al., J. Immunol. |
| SEA C106Q | 13 | 147: 3274-3281 (1991) |
| SEA C96, 106G | 10 | MOUSE |
| SEA K14E | 1 | Bavari et al., J. Infect. Dis. 174: |
| SEA Y64A | 100 | 338-345 (1996) |
| SEA Y92A | 100 | HUMAN |
| SEB (native) | 1 | Briggs et al., Immunol. 90: 169-175 |
| SEB H166A/V169E | 5 | (1997) |
| SEB H166A | 1.3 | MOUSE |
| SEB V169A | 10 | |
| SEB V169E | 5 | |
| SEB V169K | 10 | |
| SEB (native) | 1 | Alakhov et al., Eur. J. Biochem. |
| SEB (1-13, 2-13) | 7.6 | 209: 823-828 (1992) |
| | | HUMAN |
| SEB (native) | 1 | Leder et al., J. Exp. Med. 187: |
| SEB L20T | 1.2 | 823-833 (1998) |
| SEB V26Y | 1 | MOUSE |
| SEB Y91B | 1.8 | |
| SEC3 (native) | 1 | |
| SEC3 Y26A | 7 | |
| SEC3 N60A | 6 | |
| SEC3 Y90A | 8 | |
| SEC3 G106A | 6 | |
| SEC1 (native) | 1 | Hoffman et al., Infect. Immun. 62: |
| SEC 1818 (delete 7-9) | 1 | 3396-3407 (1994) |
| SEC 1819 (delete 6-10) | 1 | HUMAN |
| SEC 1820 (delete 9-13) | 1 | |
| SEC 1821 (delete 9-18) | 53 | |
| SEC $M_r$ (20-80) | 4.3 | Spero et al., J. Biol. Chem. 24: |
| | | 8787-8791 (1978) MOUSE |
| SED (native) | 1 | Sundstrom et al., EMBO J. |
| SED F42A | ~100 | 15: 6832-6840 (1996) |
| SED D182A | ~5000 | HUMAN |
| SED 218A | ~1 | |
| SED D222A | ~100,000 | |
| SEE (native) | 1 | Lamphear et al., J. Immunol. |
| SEE-Ala (20-24) | 1 | 156: 2178-2185 (1996) |
| SEE-Ala (200-207 | 1 | HUMAN |
| SEE-Ala (20-24/200-207) | 1.7 | |
| SEA (native) | 1 | Mollick et al., J. Exp. Med. 283-293 |
| SEA-SEE (200-207) | 1 | (1993) |
| SEE-SEA (70-71) | 1 | HUMAN |
| SEA-SEE (200-207) | | |
| TSST-1 (native) | 1 | Kum et al., J. Infect. Dis. 174: |
| G31R | 800 | 1261-1270 (1996) HUMAN |
| SEA-C215 mAb Fab Fusion Protein | 1 | Antonnson et al., J. Immunol. 158: 4245-4251 (1997) |
| SEE-C215 mAb Fab Fusion protein | 10 | HUMAN |
| SEE/AA-C215 mAb Fab Fusion protein | 1 | |
| SEE/A-C-C215 mAb Fab Fusion protein | 10 | |
| SEE/A-F-C215 mAb Fab Fusion protein | 10 | |
| SEE/A-H-C215 mAb Fab Fusion protein | 10 | |
| SEA/E-BDEG-mAb Fab Fusion protein | 2 | |

TABLE 1-continued

SE-Homologues Induce T Lymphocyte Mitogenesis

| SE Homologue[a] | T Lymphocyte Mitogenic Response[b] ($EC_{50}$)[c] | Reference (SPECIES) |
|---|---|---|
| SEE/A-AH-215mAb Fab Fusion protein | 2 | |

LEGEND FOR TABLE 1 (above)
[a]z values for homologues range from 16-136.
[b]Summary of Methods in all the above studies: human peripheral blood mononuclear cells (PBMC) or mouse spleen or lymph node lymphocytes were incubated with native SE or homologue (mutant) in complete medium supplemented with fetal calf serum (5 or 10% v/v) and antibiotics in wells of 96-well microplates in 200 μl volumes. In some cases, enriched or purified T lymphocytes from these populations were tested. Between $0.2 \times 10^5$ and $8 \times 10^5$ cells/well were used. Incubation was at 37° C. in humidified air/95% $CO_2$ for periods of between 66 hours and 84 hours (depending on whether unfractionated or purified T lymphocytes were being used). T lymphocyte mitogenic responses was routinely measured as radiolabeled [$^3$H]- thymidine ("TdR") incorporation during the final 4-24 hrs of incubation. Cells were always harvested from the microplates onto glass fiber filters which were dried and placed in a liquid scintillation counter for evaluation of incorporated radiolabel.
[c]Each SE or homologue was tested over a range of concentrations and the results were plotted as counts/min (cpm) of [$^3$H]TdR taken up (after subtraction of background cpm of cells incubated in medium alone, which rarely exceeded several hundred cpm) on the ordinate vs. log concentration of the SE or homologue on the abscissa. For each agent tested, the concentration at which [$^3$H]TdR incorporation was 50% of maximum (the $EC_{50}$), which falls in the linear part of the sigmoid dose-response curve, has been provided in the publication or interpolated visually and approximated (value preceded by "~" symbol) from the published graphs. The $EC_{50}$ of the native SE was arbitrarily set to 1, so an $EC_{50}$ of 10 for a homologue indicates that the homologue causes half-maximal mitogenic responsiveness at a 10-fold higher concentration.

TABLE 2

SE Homologues Induce T Lymphocyte Mitogenesis and Anti-Tumor Effects In Vitro

| SE Homologue | T Lymphocyte Mitogenic Response[1] ($EC_{50}$) | SDCC[2] ($EC_{50}$) | SADCC[3] (% of native SE) WO96/01650 |
|---|---|---|---|
| Data from: Abrahmsen et eL, EMBO J. 14: 2978–2986 (1995) | | | |
| SEA (native) | 1 | 1 | 100 |
| SEA D227A | 1057 | 132 | 100 |
| SEA F47A | 52 | 4 | 100 |
| SEA H225A | 1272 | 130 | nd |
| SEA K123A/D132G | 2 | 2 | 100 |
| SEA N128A | 2 | 3 | 100 |
| SEA K55A | 1 | 1 | nd |
| SEA H50A | 4 | 2 | 100 |
| SEA D45A | 1 | 1 | nd |
| SEA H187A | 11 | 9 | 100 |
| SEA E191A/N195A | 1 | 1 | nd |
| Data from Sundstrom et al., EMBO J. 15: 6832–6840 (1996) | | | |
| SED (native) | 1 | 1 | |
| SED F42A | ~100 | ~5 | |
| SED D182A | ~5000 | ~50 | |
| SED H218A | ~1 | ~1 | |
| SED D222A | ~50,000 | ~50 | |
| Data from Nilsson et al., J. Immunol. 163: 6686–6693 (1999) | | | |
| SEH (native) | 1 | 1 | |
| SEH D167 | 10 | 5 | |
| SEH D203A | 7 | 5 | |
| SHE D208A | 300 | 10 | |

LEGEND FOR TABLE 2 (above):
[1]Lymphocyte proliferation assays:
(a) Abrahmsen et al., 1995: Peripheral blood mononuclear cells (PBMC) from heparinized blood of normal donors were isolated by density centrifugation over Ficoll-Hypaque. Following this, $2 \times 10^5$ PBMC/0.2 ml complete medium were incubated in microplates with varying amounts of SEA or SEA mutants for 72 h and tested for mitogenic responses (proliferation) by incorporation of [$^3$H]-thymidine during the last 4 h of culture. The SEA mutant concentration resulting in half-maximum proliferation ($EC_{50}$) was related to the $EC_{50}$ of the native SE, arbitrarily set to 1 (see column 2). Thus, the SEA homologue concentration to induce half maximal response was related to the same values induced by native SEA.
(b) Sundstrom et al., 1996: $10^5$ human PBMC prepared as above were incubated at 37° C. in 0.2 ml complete medium in U-shaped microplate wells with varying amounts of native SED or SED mutants for 96 hrs. Proliferation was estimated by incorporation of [$^3$H]thymidine added during the final 24 hrs. $EC_{50}$ values were estimated by interpolating the curves in this publication.
(c) Nilsson et al., 1999: $2 \times 10^5$ human PBMC were prepared as above incubated in flat bottom microwells in 0.2 ml volumes at 37° C. for 72 h with varying amounts of native SEH and variants. Each well was pulsed with 0.5 [Ci =$^3$H]thymidine for 4 h. Cells were harvested and proliferation measured as incorporation of [3H]thymidine. The $EC_{50}$ values of the SEH variants were related to the $EC_{50}$ of native SEH which was 0.2 pM.
[2]SDCC = Superantigen dependent mediated cellular cytotoxicity. This assay measures the ability of an SE (whether native or mutant) to target cytotoxic T lymphocytes onto MHC class II+ target cells resulting in their lysis. The same conditions were used in the above publications. The cytotoxicity of SE (wt) and homologues against MHC class II+ Raji cells was analyzed in a standard 4 or 6 hour $^{51}$Cr-release assay, using SE-specific T cell lines that had been stimulated in vitro (with the wild-type SE) as effector cells. Briefly, $2.5 \times 10^3$ $^{51}$Cr-labeled Raji cells were incubated in 0.2 ml medium (RPMI, 10% FCS) in microwells in the presence effector cells at an effector:target cell ratio of 30 and in the presence (or absence for negative controls) of the SE's or homologues. After incubation, 0.1 ml of medium was withdrawn and counted in a gamma counter to determine isotope release. % specific cytotoxicity was calculated as $$100 \times \frac{\text{(c.p.m. experimental release} - \text{c.p.m. background release)}}{\text{(c.p.m. total release} - \text{c.p.m. background release)}}.$$

The SE homologue concentration resulting in half-maximum cytotoxicity ($EC_{50}$) was related to the $EC_{50}$ of the native SE, arbitrarily set to 1. Thus, the SE homologue concentration needed to promote half maximal cytotoxicity was related to the same values induced by the native or wild SE. $EC_{50}$ values were provided by the authors, or, in the case of the Lundstrom reference, they were estimated by interpolating the curves in this publication (shown as approximate using the ~ symbol.
[3]SADCC = Superantigen-tumor specific antibody mediated cellular cytotoxicity. This is similar to SDCC but involves an antibody component in the form of a fusion protein that directs the specificity of the targeting. Here, this assay measure the ability of a fusion protein comprising an SE (native or mutant) fused to an antibody Fab fragment to target activated cytotoxic T lymphocytes onto tumor cells expressing the tumor antigen (colon cancer antigen) against which the antibody (C215)is specific. This targeting leads to tumor cell lysis, as above. The cytotoxicity of C215Fab- TABLE 2-continued SE Homologues Induce T Lymphocyte Mitogenesis and
Anti-Tumor Effects In Vitro

| SE Homologue | T Lymphocyte Mitogenic Response[1] ($EC_{50}$) | $SDCC^2$ ($EC_{50}$) | $SADCC^3$ (% of native SE) WO96/01650 |
|---|---|---|---|

SEA(wt), C215Fab-SEA(m), SEA(wt) and SEA mutants against C215+ MHC class II$^{neg}$ colon carcinoma cells SW 620 was analyzed in a standard 4 hour $^{51}Cr^{3+}$-release assay, using in vitro stimulated SEA specific T cell lines as effector cells. Briefly, $^{51}Cr^{3+}$-labeled SW 620 cells were incubated at $2.5 \times 10^3$ cells per 0.2 ml medium {RPMI, 10% FCS) in microtiter wells at effector to target cell ratio 30:1 in the presence or absence (control) of the additives. Percent specific cytotoxicity was calculated as for SDCC assays.

The present invention contemplates the direct administration of any SAg (SEA, SEB and SEC are preferred) into a fluid space containing tumor cells or adjacent to membranes such as pleural, peritoneal, pericardial and thecal spaces containing tumor. These sites display malignant ascites, pleural and pericardial effusions or meningeal carcinomatosis. The SAg is preferably administered after partial or complete drainage of the fluid (e.g., ascites, pleural or pericardial effusion) but it may also be administered directly into the undrained space containing the effusion, ascites and/or carcinomatosus. In general, the SE dose may vary from 1 picogram to 10 μg and given every 3 to 10 days. It is continued until there is no reaccumulation of the ascites or effusion. Therapeutic responses are considered to be no further accumulation of four weeks after the last intrapleural administration. See Example 1 for further description of treatment.

Fusion Partners for Native SEs or SE Homologues

Antibodies

Fusion protein partners for the SAg include tumor specific antibodies, preferably $F(ab')_2$, Fv or Fd fragments thereof, that are specific for antigens expressed on the tumor. In another embodiment, a fusion partner is a polypeptide ligand f for a receptor expressed on tumor cells. These antibodies, fragments or receptor ligands may be in the form of synthetic polypeptides. The nucleic acid form of the antibody is envisioned which is useful as a fusion construct with the SAg DNA.

One advantage of certain antibody constructs of the present fusion polypeptides is prolonged half-life and enhanced tissue penetration. Intact antibodies in which the Fc fragment of the Ig chain is present will exhibit slower blood clearance than their Fab' fragment counterparts, but a fragment-based fusion polypeptide will generally exhibit better tissue penetrating capability.

Preferentially, the tumor targeting structure in the SAg conjugate (e.g., tumor specific antibody, Fab or single chain Fv fragments or tumor receptor ligand) has a greater affinity for the tumor than the SAg in the conjugate has for the class II molecule thus preventing the SAg from binding all MHC class II receptors and favoring binding of the conjugate to the tumor. In the case of SEB, the dominant epitope for neutralizing antibodies 225-234 is recombinantly or biochemically bound to the tumor targeting molecule e.g., tumor specific antibodies, Fas or Fv fragments. In so doing, it sterically interferes with the recognition of the dominant epitope by preexisting antibodies.

To further enhance the affinity of the tumor specific antibody in the conjugate for tumor cells in vivo, tumor specific antibodies are used which are specific for more than one antigenic structures on the tumor, tumor stroma or tumor vasculature or any combination thereof. The tumor specific antibody or $F(ab')_2$, Fab or single chain Fv fragments are mono or divalent like IgG, polyvalent for maximal affinity like IgM or chimeric with multiple tumor (tumor stroma or tumor vasculature) specificities. Thus, when the SE or SPE-MoAb conjugate is administered in vivo, it will preferentially bind to tumor cells rather than to endogenous SE antibodies or MHC class II receptors.

To reduce affinity of the SE-mAb conjugate for endogenous MHC class II binding sites, the high affinity $Zn^{++}$ dependent MHC class II binding sites in SEA, SEC2, SEC3, SED, SPEA, SPEC, SPEG, SPEH, SMEZ, SMEZ2, *M. arthritides* are deleted or replaced by inert sequence(s) or amino acid(s). These structural alterations in SE or SPEA reduce the affinity for MHC class II receptors from a $K_d$ of $10^{-7}$ or $10^{-8}$ to $10^{-5}$. SEB, SEC and SSA and other SEs or SPEs do not have a high affinity Zn++ dependent MHC class II binding site but have multiple low affinity MHC class II binding sites ($K_d$ $10^{-5}$-$10^{-7}$). In these cases, alteration of the MHC class II binding sites is not always necessary to further reduce affinity for MHC class II receptors; at the very least mutation of one or two of the low affinity MHC class II binding sites will suffice in most instances.

Most importantly, tumor specific antibodies, Fab, $F(ab')_2$ or single chain Fab or Fv fragments in the SAg-mAb conjugate have a higher affinity for tumor antigens ($K_d$ $10^{-11}$-$\mathbf{10}^{-14}$ or lower) than for the SAg has for MHC class II binding sites ($K_d$ $10^{-5}$ to $10^{-7}$) and its dominant epitope has for SAg specific antibodies ($K_d$ $10^{-7}$ to $10^{-11}$). In this way, the conjugate will bind preferentially to the tumor target in vivo rather than preexisting antibodies or MHC class II receptors.

Antibody fragments are obtained using conventional proteolytic methods. Thus, a preferred procedure for preparation of $F(ab')_2$ fragments from IgG of rabbit and human origin is limited proteolysis by the enzyme pepsin. Rates of digestion of an IgG molecule may vary according to isotype; conditions are chosen to avoid significant amounts of completely degraded IgG as is known in the art.

Fab fragments include the constant domain of the light chain ($C_L$) and the first constant domain ($C_{H1}$) of the heavy chain. Fab' fragments differ from Fab fragments by the addition of a few residues at the C-terminus of $C_{H1}$ domain including one or more cysteine(s) from the antibody hinge region. $F(ab')_2$ fragments were originally produced as pairs of Fab' fragments that have hinge cysteines between them. Other chemical couplings of antibody fragments are also known.

An "Fv" fragment is the minimum antibody fragment that contains a complete antigen-recognition and binding site. This region consists of a dimer of one heavy chain and one light chain variable domain in tight, con-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

"Single-chain Fv" or "scFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains that enables the scFv to form the desired structure for antigen binding.

The following documents, incorporated by reference, describe the preparation and use of functional, antigen-binding regions of antibodies: U.S. Pat. Nos. 5,855,866; 5,965,132; 6,051,230; 6,004,555; and 5,877,289.

"Diabodies" are small antibody fragments with two antigen-binding sites, which fragments comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites. Diabodies are described in EP 404,097 and WO 93/11161, incorporated herein by reference. "Linear antibodies", which can be bispecific or monospecific, comprise a pair of tandem Fd segments ($V_H$-$C_{H1}$-$V_H$-$C_{H1}$) that form a pair of antigen binding regions.

An antibody fragment may be further modified to increase its half-life by any of a number of known techniques. Conjugation to non-protein polymers, such PEG and the like, is also contemplated The antibody fusion partner for use in the present invention may be specific for tumor cells, tumor stroma or tumor vasculature. Antigens expressed on tumor cells that are suitable targets for mAb-SAg fusion protein therapy include erb/neu, MUC1, 5T4 and many others. Antibodies specific for tumor vasculature bind to a molecule expressed or localized or accessible at the cell surface of blood vessels, preferably the intratumoral blood vessels, of a vascularized tumor. Such molecules include endoglin (TEC-4 and TEC-11 antibodies), a TGFβ. receptor, E-selectin, P-selectin, VCAM-1, ICAM-1, PSMA, a VEGF/VPF receptor, an FGF receptor, a TIE, an $\alpha_v\beta_3$ integrin, pleiotropin, endosialin and MHC class II proteins. Such antibodies may also bind to cytokine-inducible or coagulant-inducible products of intratumoral blood vessels. Certain preferred agents will bind to aminophospholipids, such as phosphatidylserine or phosphatidylethanolamine.

A tumor cell-targeting antibody, or an antigen-binding fragment thereof, may bind to an intracellular component that is released from a necrotic or dying tumor cell. Preferably such antibodies are mAbs or fragments thereof that bind to insoluble intracellular antigen(s) present in cells that may be induced to be permeable, or in cell ghosts of substantially all neoplastic and normal cells, but are not present or accessible on the exterior of normal living cells of a mammal.

Anti-tumor stroma antibodies bind to a connective tissue component, a basement membrane component or an activated platelet component; as exemplified by binding to fibrin, RIBS (receptor-induced binding site) or LIBS (ligand-induced binding site).

Fusion protein optionally include linkers or spacers. Numerous types of disulfide-bond containing linkers are known that can be successfully employed to fuse the SAg to an antibody or fragment, certain linkers are preferred based on differing pharmacological characteristics and capabilities. For example, linkers that contain a disulfide bond that is sterically "hindered" are preferred, due to their greater stability in vivo, thus preventing release of the SAg moiety prior to binding at the site of action.

Coaguligand

SAgs may be conjugated to, or operatively associated with, polypeptides that are capable of directly or indirectly stimulating coagulation, thus forming a "coaguligand" (Barinaga M et al., Science 275:482-4 (1997); Huang X et al., Science 275:547-50 (1997); Ran S et al., Cancer Res 1998 Oct. 15; 58(20):4646-53; Gottstein C et al., Biotechniques 30:190-4 (2001)).

In coaguligands, the antibody may be directly linked to a direct or indirect coagulation factor, or may be linked to a second binding region that binds and then releases a direct or indirect coagulation factor. The 'second binding region' approach generally uses a coagulant-binding antibody as a second binding region, thus resulting in a bispecific antibody construct. The preparation and use of bispecific antibodies in general is well known in the art, and is further disclosed herein.

Coaguligands are prepared by recombinant expression. The nucleic acid sequences encoding the SAg are linked, in-frame, to nucleic acid sequences encoding the chosen coagulant, to create an expression unit or vector. Recombinant expression results in translation of the new nucleic acid, to yield the desired protein product.

Where coagulation factors are used in connection with the present invention, any covalent linkage to the SAg should be made at a site distinct from the functional coagulating site. The compositions are thus "linked" in any operative manner that allows each region to perform its intended function without significant impairment. Thus, the SAg binds to and stimulates T cells, and the coagulation factor promotes blood clotting.

Preferred coagulation factors are Tissue Factor ("TF") compositions, such as truncated TF ("tTF"), dimeric, multimeric and mutant TF molecules. tTF is a truncated TF that is deficient in membrane binding due to removal of sufficient amino acids to result in this loss. "Sufficient" in this context refers to a number of transmembrane amino acids originally sufficient to insert the TF molecule into a cell membrane, or otherwise mediate functional membrane binding of the TF protein. The removal of a "sufficient amount of transmembrane spanning sequence" therefore creates a tTF protein or polypeptide deficient in phospholipid membrane binding capacity, such that the protein is substantially soluble and does not significantly bind to phospholipid membranes. tTF thus substantially fails to convert Factor VII to Factor VIIa in a standard TF assay yet retains so-called catalytic activity including the ability to activate Factor X in the presence of Factor VIIa.

U.S. Pat. No. 5,504,067, specifically incorporated herein by reference, describes tTF proteins. Preferably, the TFs for use herein will generally lack the transmembrane and cytosolic regions (amino acids 220-263) of the protein. However, the tTF molecules are not limited to those having exactly 219 amino acids.

Any of the truncated, mutated or other TF constructs may be prepared in dimeric form employing the standard techniques of molecular biology and recombinant expression, in which two coding regions are arranged in-frame and are expressed from an expression vector. Various chemical conjugation technologies may be employed to prepare TF dimers. Individual TF monomers may be derivatized prior to conjugation.

The tTF constructs may be multimeric or polymeric, which means that they include 3 or more TF monomeric units. A "multimeric or polymeric TF construct" is a construct that comprises a first monomeric TF molecule (or derivative) linked to at least a second and a third monomeric TF molecule (or derivative). The multimers preferably comprise between about 3 and about 20 such monomer units. The constructs may be readily made using either recombinant techniques or conventional synthetic chemistry.

TF mutants deficient in the ability to activate Factor VII are also useful. Such "Factor VII activation mutants" are generally defined herein as TF mutants that bind functional Factor VII/VIIa, proteolytically activate Factor X, but substantially lack the ability to proteolytically activate Factor VII.

The ability of such Factor VII activation mutants to function in promoting tumor-specific coagulation is requires their delivery to the tumor vasculature and the presence of Factor VIIa at low levels in plasma. Upon administration of a conjugate of a Factor VII activation mutant, the mutant will be localize within the vasculature of a vascularized tumor. Prior to localization, the TF mutant would be generally unable to promote coagulation in any other body sites, on the basis of its inability to convert Factor VII to Factor VIIa. However, upon localization and accumulation within the tumor region, the mutant will then encounter sufficient Factor VIIa from the plasma in order to initiate the extrinsic coagulation pathway, leading to tumor-specific thrombosis. Exogenous Factor VIIa could also be administered to the patient to interact with the TF mutant and tumor vasculature.

Any one or more of a variety of Factor VII activation mutants may be prepared and used in connection with the present invention. The Factor VII activation region generally lies between about amino acid 157 and about amino acid 167 of the TF molecule. Residues outside this region may also prove to be relevant to the Factor VII activating activity. Mutations are inserted into any one or more of the residues generally located between about amino acid 106 and about amino acid 209 of the TF sequence (WO 94/07515; WO 94/28017; each incorporated herein by reference).

A variety of other coagulation factors may be used in connection with the present invention, as exemplified by: the agents set forth below. Thrombin, Factor V/Va and derivatives, Factor VIII/VIIIa and derivatives, Factor IX/IXa and derivatives, Factor X/Xa and derivatives, Factor XI/XIa and derivatives, Factor XII/XIIa and derivatives, Factor XIII/XIIIa and derivatives, Factor X activator and Factor V activator may be used in the present invention.

These conjugates are administered intrathecally in dosages of 0.01 ng/kg to 100 µg/kg.

Cytokines as Fusion Partners

Cytokines are an effective partner for SAgs. Various cytokines, such as IL-2, IL-3, IL-7, IL-12, and IL-18, may be used.

A preferred fusion polypeptide comprises a SAg fused to anti-apoptotic cytokines. SAg stimulation of T cells can result in activation-driven cell death. Several cytokines and bacterial lipopolysaccharide (LPS) are known to interfere with this process (Vella et al., Proc. Natl. Acad. Sci. 95: 3810-3815 (1998)). IL-3, IL-7, IL-15 and IL-17 prevent SAg-stimulated T cells from undergoing apoptosis in vivo and in vitro. In addition, because of their ability to promote selective proliferation by Th$_1$ T cells, IL-12 and IL-18 are desirable. IL-18 is preferred for intratumoral injection because it induces tumor suppressive cytokines IFNγ and TNFα and IL-1β, and rescues cytotoxic T cells from apoptosis.

Accordingly, SAg-mAb conjugate as described above is fused recombinantly to the extracellular domains of at least one cytokine from a group consisting of IL-2. IL-7 or IL-3 or IL-12 or IL-15 or IL-17 or IL-18. Other anti-T cell apoptosis agents such as LPS preparations of low virulence or a lipid A component (modified to induce less toxicity) are also effective antiapoptotic agents when conjugated biochemically to the SAg-MoAb (or F(ab')$_2$, Fab, Fd or single chain Fv fragments) conjugate or if administered concomitantly with the SAg. Nucleic acids encoding the cytokine of choice is fused in frame with nucleic acids encoding the SAg. These conjugates are administered parenterally, intrathecally and/or intratumorally by infusion or injection in dosages of 0.01 ng/kg to 100 µg/kg.

Costimulatory Molecules as Fusion Partners

Superantigens Conjugated to OX40L or 4-1BBL

A preferred fusion polypeptide comprises a SAg fused recombinantly to a potent costimulatory molecule, preferably the ECD of a transmembrane costimulatory protein. Examples of such costimulatory molecules are the OX-40 ligand (Godfrey et al., J. Exp. Med. 180: 757-762 (11994); Gramaglia I et al., J. Immunol. 161: 6510-6517 (1998); Maxwell J R et al., J. Immunol. 164: 107-112 (2000) or 4-1BB ligand (Kown B S et al., Proc. Natl. Acad. Sci. USA 86:1963-67 (1989); Shuford W W et al., J. Exp. Med. 186: 47-55 (1997) and CD-38 (Jackson D G et al., J. Immunol. 144: 2811-2817 (1990); Zilber et al., Proc. Nat'l Acad. Sci. USA 97: 2840-2845 (2000). The preparation of such fusion proteins is achieved by recombinant methods in which nucleic acids encoding SAgs are fused in frame to nucleic acids encoding the ECD of the costimulatory molecule such as OX-40L (Godfrey et al., J. Exp. Med 180:757-762 (1994)) or 4-1BBL (Goodwin et al. Eur. J. Immunol. 23: 2631-2641 (1993); Melero I. et al., Eur. J. Immunol. 28: 1116-1121 (1998)).

It is preferred to delete from the conjugates or fusion polypeptides of the present invention any SAg epitope that binds to SAg-specific antibodies, including preexisting or natural antibodies). Such epitopes are deleted or substituted by Ala or by amino acid sequences not recognized by preexisting host antibodies. For example, a dominant epitope of SEB that is recognized by anti-SEB antibodies is the sequence at residues 225-234 (Nishi et al., J. Immunol. 158: 247-254 (1997). An epitope of SEA that is recognized by anti-SEA antibodies is the sequence at residues 121-149 (Hobieka et al., Biochem. Biophys. Res. Comm. 223: 565-571 (1996). Alternatively, to avoid issues with such preexisting immunity. SAgs such as YPM or C. perfringens toxin A to which humans do not have preexisting antibodies are selected. YPM, in addition, a natural RGD domain which gives it tumor localizing properties. The SE may be modified to reduce toxicity by altering its MHC class II binding affinity (e.g., SEA D277A-high affinity Zn++ dependent binding site).

Preferably, the tumor targeting structure in SAg conjugate (e.g., tumor specific antibody or fragment, or a tumor receptor ligand) has greater affinity for the tumor than the affinity of the SAg in the conjugate for the MHC class II molecule thus preventing the SAg from binding "promiscuously" to all MHC class II molecules receptors and favoring binding to the tumor. In the case of SEB, the dominant epitope for neutralizing antibodies, residues 225-234, is recombinantly or biochemically conjugated to the tumor targeting molecule (e.g., tumor specific antibody, etc.) so that it can sterically interfere with the recognition of the dominant epitope by preexisting antibodies in the host.

To further enhance the affinity of the tumor specific antibody in the fusion polypeptide for tumor cells in vivo, one preferably selects a tumor specific antibody that is specific for more than one antigenic structures of the tumor, the tumor stroma or the tumor vasculature (or any combination). The tumor specific antibody or antigen-binding fragment thereof can be made mono or divalent (like IgG), polyvalent like IgM to increase avidity or chimeric with multiple tumor specificities as described above. Thus, when the SAg-mAb conjugate is administered in vivo, it will preferentially bind to tumor cells rather than to endogenous anti-SAg antibodies or MHC class II receptors.

To reduce affinity of the SAg-mAb conjugate for endogenous MHC class II binding sites, the high affinity Zn$^{++}$ dependent MHC class II binding site present in a number of SAgs (SEA, SEC2, SEC3, SED, SPEA, SPEC, SPEG, SPEH, SMEZ, SMEZ2, M. arthritides SAg) is deleted or replaced by an "inert" sequence(s) or amino acid. Such structural alterations in SE or SPEA are known to reduce the affinity for MHC class II from a K$_d$ of $10^{-7}$ or $10^{-8}$ to a K$_d$ of $10^{-5}$. SEB, SEC and SSA and other SAgs do not have such a high affinity $Zn^{++}$-dependent MHC class II binding site but have multiple low affinity MHC class II binding sites ($K_d$ of $10^{-5}$-$10^{-7}$). In these cases, alteration of the MHC class II binding sites is not always necessary to further reduce affinity for MHC class II; mutation of one or two of the low affinity MHC class II binding sites will suffice in most instances.

Most importantly, tumor specific antibodies or their fragments in a SAg-mAb conjugate have higher affinities for tumor antigens ($K_d$ of $10^{-11}$-$10^{-14}$ or lower) than (a) the affinity of the SAg for MHC class II binding sites ($K_d$ $10^{-5}$ to $10^{-7}$) or (b) the affinity a dominant SAg epitope for a SAg-specific antibody ($K_d$ $10^{-7}$ to $10^{-11}$). Because of this, the conjugate will bind preferentially to the tumor target in vivo SAg-OX-40 ligand (OX-40L) or 4-1BB ligand (4-1BBL) are fused to a tumor specific targeting structure using recombinant SAgs. A most preferred construct combines the ECD of OX-40L or 4-1BBL with a high affinity tumor specific Fv antibody fragments. The nucleic acids encoding the ECD of OX-40L (Godfrey et al., supra or 4-1BBL (Goodwin et al., *Eur. J. Immunol.* 23: 2631-2641 (1993); Melero I. et al., *Eur. J. Immunol.* 28: 1116-1121 (1998)) are fused in frame with nucleic acids encoding a SAg of any type, although SEA, SEB, SEC and *Y. pseudotuberculosis* are preferred. The SAg may be modified to reduce antigenicity by modifying a dominant epitope and to reduce toxicity by altering its MHC class II binding affinity as described above. The tumor targeting structure may include but is not limited to a tumor receptor ligand or tumor-specific antibody or a fragment thereof. Preferably, the affinity of the tumor targeting structure is of higher affinity than is the affinity of the modified SAg for MHC class II. High affinity scFv constructs specific for the OX-40 receptor and 4-1BB receptor may be used in place of the OX40L and 4-1BBL in the SAg-tumor targeting construct.

The SE-OX-40L (or 4-1BB) conjugates described above are administered parenterally, intratumorally, intrathecally (e.g., intraperitoneally, intrapleurally) by infusion or injection in conventional or sustained release vehicles in dosages of 0.01 ng/kg to 100 μg/kg using standard protocols or those exemplified herein. Frequency of administration may be every 3-7 days.

Biochemical Cross-linkers

In the above fusion polypeptides or conjugates, the SAgs may be linked directly to a fusion partner or fused/conjugated via certain preferred biochemical linker or spacer groups. For chemical conjugates, cross-linking reagents are preferred and are used to form molecular bridges that bond together functional groups of two different molecules. Heterobifunctional crosslinkers can be used to link two different proteins in a step-wise manner while preventing unwanted homopolymer formation. Such cross-linkers are listed in Table 3, below.

Hetero-bifunctional cross-linkers contain two reactive groups one (e.g., N-hydroxy succinimide) generally reacting with primary amine group and the other (e.g., pyridyl disulfide, maleimides, halogens, etc.) reacting with a thiol group. Compositions to be crosslinked therefore generally have, or are derivatized to have, a functional group available. This requirement is not considered to be limiting in that a wide variety of groups can be used in this manner. For example, primary or secondary amine groups, hydrazide or hydrazine groups, carboxyl, hydroxyl, phosphate, or alkylating groups may be used for binding or cross-linking.

The spacer arm between the two reactive groups of a cross-linker may be of various length and chemical composition. A longer, aliphatic spacer arm allows a more flexible linkage while certain chemical groups (e.g., benzene group) lend extra stability or rigidity to the reactive groups or increased resistance of the chemical link to the action of various agents (e.g., disulfide bond resistant to reducing agents). Peptide spacers, such as Leu-Ala-Leu-Ala, are also contemplated.

It is preferred that a cross-linker have reasonable stability in blood. Numerous known disulfide bond-containing linkers can be used to conjugate two polypeptides. Linkers that contain a disulfide bond that is sterically hindered may give greater stability in vivo, preventing release of the agent prior to binding at the desired site of action.

A most preferred cross-linking reagents for use in with antibody chains is SMPT, a bifunctional cross-linker containing a disulfide bond that is "sterically hindered" by an adjacent benzene ring and methyl groups. Such steric hindrance of the disulfide bond may protect the bond from attack by thiolate anions (e.g., glutathione) which can be present in tissues and blood, and thereby help in preventing decoupling of the conjugate prior to the delivery to the target, preferably tumor, site. SMPT cross-links functional groups such as —SH or primary amines (e.g., the ε-amino group of Lys).

TABLE 3

Hetero-Bifunctional Cross-linkers

| Linker | Advantages and Applications | Spacer arm length after cross linking |
|---|---|---|
| Succinimidyloxycarbonyl-α-(2-pyridyldithio)toluene (SMPT)[1] | Greater stability | 11.2 A |
| N-succinimidyl 3-(2-pyridyldithio)propionate (SPDP)[2] | Thiolation | 6.8 A |
| Sulfosuccinimidyl-6-[α-methyl-α-(2-pyridyldithio)toluamido]hexanoate (Sulfo-LC-SPDP)[1] | Extended spacer arm; Water-soluble | 15.6 A |
| Succinimidyl-4-(N-maleimidomethyl)cyclohexane-1-carboxylate (SMCC)[1] | Stable maleimide reactive group; conjugation of enzyme or other polypeptide to antibody | 11.6 A |
| Succimimidyl-4-(N-maleimidomethyl)cyclohexane-carboxylate (Sulfo-SMCC)[1] | Stable maleimide reactive group; water-soluble | 11.6 A |
| m-Maleimidobenzoyl-N-hydroxysuccinimide (MBS)[1] | Enzyme-antibody conjugation; hapten-carrier protein conjugation | 9.9 A |
| m-Maleimidobenzoyl-N-hydroxysulfosuccinimide (Sulfo-MBS)[1] | Water-soluble | 9.9 A |
| N-Succinimidyl(4-iodacetyl)aminobenzoate (SIAB)[1] | Enzyme-antibody conjugation | 10.6 A |
| Sulfosuccinimidyl(4-iodoacetyl)aminobenzoate (Sulfo-SIAB)[1] | Water-soluble | 10.6 A |
| Succinimidyl-4-(p-maleimidophenyl)butyrate (SMPB)[1] | Enzyme-antibody conjugation; extended spacer arm | 14.5 A |
| Sulfosuccinimidyl-4-(p-maleimidophenyl)butyrate (Sulfo-SMPB)[1] | Extended spacer arm Water-soluble | 14.5 A |
| 1-ethyl-3-(3-dimethylaminopropyl)-carbodiimide hydrochloride (EDC) + N-hydroxysulfosuccinimide (sulfoNHS)[3] | Hapten-Carrier conjugation | 0 |
| p-Azidobenzoyl hydrazide (ABH)[4] | Reacts with sugar groups | 11.9 A |

[1]Reactive toward primary amines, sulfhydryls
[2]Reactive toward primary amines
[3]Reactive toward primary amines. carboxyl groups
[4]Reactive toward carbohydrates, nonselective Hetero-bifunctional photoreactive phenylazides containing a cleavable disulfide bond, for example, sulfosuccinimidyl-2-(p-azido salicylamido)-ethyl-1,3'-dithiopropionate. The N-hydroxy-succinimidyl group reacts with primary amino groups and the phenylazide (upon photolysis) reacts non-selectively with any amino acid residue.

Other useful cross-linkers, not considered to contain or generate a protected disulfide, include SATA, SPDP and 2-iminothiolane. The use of such cross-linkers is well known in the art.

Once conjugated, the conjugate is separated from unconjugated SAg and fusion partner polypeptides and from other contaminants. A large a number of purification techniques are available for use in providing conjugates of a sufficient degree of purity to render them clinically useful. Purification methods based upon size separation, such as gel filtration, gel permeation or high performance liquid chromatography, will generally be of most use. Other chromatographic techniques, such as Blue-Sepharose separation, may also be used.

Chemotherapeutic and Other Agents

Chemotherapeutic agents can be used together with intrathecal or intratumoral SAg. They can be administered intrathecally, intratumorally or parenterally by infusion or injection concomitantly with SAg. Preferably they are given together with SAg after 2-7 weeks of treatment with the SAg alone. Anti-cancer chemotherapeutic drugs useful in this invention include but are not limited to antimetabolites, anthracycline, vinca alkaloid, anti-tubulin drugs, antibiotics and alkylating agents. Representative specific drugs that can be used alone or in combination include cisplatin (CDDP), adriamycin, dactinomycin, mitomycin, carminomycin, daunomycin, doxorubicin, tamoxifen, taxol, taxotere, vincristine, vinblastine, vinorelbine, etoposide (VP-16), 5-fluorouracil (5FU), cytosine arabinoside, cyclophosphamide, thiotepa, methotrexate, camptothecin, actinomycin-D, mitomycin C, aminopterin, combretastatin(s) and derivatives and prodrugs thereof.

A variety of chemotherapeutic and pharmacological agents may be given separately or conjugated to a therapeutic protein of the invention. Exemplary antineoplastic agents that have been conjugated to proteins include doxorubicin, daunomycin, methotrexate and vinblastine. Moreover, the attachment of other agents such as neocarzinostatin, macromycin, trenimon and α-amanitin has been described. See U.S. Pat. Nos. 5,660,827; 5,855,866; and 5,965,132; each incorporated by reference herein. Those of ordinary skill in the art will know how to select appropriate agents and doses, although, as disclosed, the doses of chemotherapeutic drugs are preferably reduced when used in combination with SAgs according to the present invention.

Another newer class of drugs also termed "chemotherapeutic agents" comprises inducers of apoptosis. Any one or more of such drugs, including genes, vectors, antisense constructs, siRNA constructs, and ribozymes, as appropriate, may be used in conjunction with SAgs.

Other agents useful herein are anti-angiogenic agents, such as angiostatin, endostatin, vasculostatin, canstatin and maspin.

Chemotherapeutic agents are administered as single agents or multidrug combinations, in full or reduced dosage per treatment cycle. They can be administered with the intrathecal or intratumoral and optionally parenteral SAg composition although, under a preferred schedule, the chemotherapeutic agent is administered within 36 hours of the last of two to four treatments of SAg compositions administered intrathecally or intratumorally.

The combined use of the SAg compositions with low dose, single agent chemotherapeutic drugs is particularly preferred. The choice of chemotherapeutic drug in such combinations is determined by the nature of the underlying malignancy. For lung tumors, cisplatin is preferred. For breast cancer, a microtubule inhibitor such as taxotere is the preferred. For malignant ascites due to gastrointestinal tumors, 5-FU is preferred. "Low dose" as used with a chemotherapeutic drug refers to the dose of single agents that is 10-95% below that of the approved dosage for that agent (by the U.S. Food and Drug Administration, FDA). If the regimen consists of combination chemotherapy, then each drug dose is reduced by the same percentage. A reduction of >50% of the FDA approved dosage is preferred although therapeutic effects are seen with dosages above or below this level, with minimal side effects.

Tumors to treat with SAgs (±chemotherapeutics) using intratumoral injection are preferably at least 6 $cm^3$ and visible by x-ray, CT, ultrasound, bronchoscopy, laparoscopy, culdoscopy. Intratumoral localization of the agent being delivered is facilitated with fluoroscopic, CT or ultrasound guidance. Representative tumors that are treatable with this approach include but are not limited to hepatocellular carcinoma, lung tumors, brain tumors, head and neck tumors and unresectable breast tumors. Multiple tumors at different sites may be treated by intrathecal or intratumoral SAg.

The chemotherapeutic agent(s) selected for therapy of a particular tumor preferably is one with the highest response rates against that type of tumor. For example, for non-small cell lung cancer (NSCLC), cisplatin-based drugs have been proven effective. Cisplatin may be given parenterally or intratumorally. When given intratumorally, Cisplatin is preferentially in small volume around 1-4 ml although larger volumes can also work. The smaller volume is designed to increase the viscosity of the Cisplatin containing solution in order to minimize or delay the clearance of the drug from the tumor site. Other agents useful in NSCLC include the taxanes (paclitaxel and docetaxel), vinca alkaloids (vinorelbine), antimetabolites (gemcitabine), and camptothecin (irinotecan) both as single agents and in combination with a platinum agent.

The optimal chemotherapeutic agents and combined regimens for all the major human tumors are set forth in *Bethesda Handbook of Clinical Oncology*, Abraham J et al., Lippincott William & Wilkins, Philadelphia, Pa. (2001); *Manual of Clinical Oncology*, Fourth Edition, Casciato, D A et al., Lippincott William1 & Wilkins, Philadelphia, Pa. (2000) both of which are herein incorporated in entirety by reference.

In one embodiment, these recommended chemotherapeutic agents are used alone or combined with other chemotherapeutics in full doses. Alternatively they may be administered parenterally by infusion or injection in doses 10-95% below the FDA recommended therapeutic dose. For intratumoral administration, the dose of a chemotherapeutic drug or biologic agent is preferably reduced 10- to 50-fold below the FDA-recommended dose for parenteral administration.

Cisplatin has been widely used to treat cancer, with effective doses of 20 $mg/m^2$ for 5 days every three weeks for a total of three courses. Preferred dose per treatment for intratumoral use of Cisplatin is 5-10 mg whereas for intrathecal use 20-80 mg may be administered. Intratumoral cisplatin may be given every 7-14 days for 10-20 treatments whereas intrathecal cisplatin may be given every 2-6 weeks for 10-20 treatments. Cisplatin delivered in small volumes, e.g., 5-10 mg/1-5 ml saline, is extremely viscous and may be retained in a tumor for a sustained period, thereby acting like a controlled release drug being released from an inert surface. This is indeed the preferred mode of administration of Cisplatin when administered intratumorally with or without the SAg. Preferably cisplatin is administered together with the SAg in the same syringe.

Other chemotherapeutic compounds include doxorubicin, etoposide, verapamil, podophyllotoxin, and the like which are administered through intravenous bolus injections at doses ranging from 25-75 mg/m$^2$ at 21 day intervals for adriamycin, to 35-50 mg/m$^2$ for etoposide intravenously.

Other agents and therapies that are operable together with or after intratumoral SAg include, radiotherapeutic agents, antitumor antibodies with attached anti-tumor drugs such as plant-, fungus-, or bacteria-derived toxin or coagulant, ricin A chain, deglycosylated ricin A chain, ribosome inactivating proteins, sarcins, gelonin, aspergillin, restricticin, a ribonuclease, a epipodophyllotoxin, diphtheria toxin, or *Pseudomonas* exotoxin. Additional cytotoxic, cytostatic or anti-cellular agents capable of killing or suppressing the growth or division of tumor cells include anti-angiogenic agents, apoptosis-inducing agents, coagulants, prodrugs or tumor targeted forms, tyrosine kinase inhibitors (Siemeister et al., 1998), antisense strategies, RNA aptamers, siRNA and ribozymes against VEGF or VEGF receptors (Saleh et al., 1996; Cheng et al., 1996; Ke et al., 1998; Parry et al., 1999; each incorporated herein by reference).

Any of a number of tyrosine kinase inhibitors are useful when administered together with, or after, intratumoral SAg. These include, for example, the 4-aminopyrrolo[2,3-d]pyrimidines (U.S. Pat. No. 5,639,757). Further examples of small organic molecules capable of modulating tyrosine kinase signal transduction via the VEGF-R2 receptor are the quinazoline compounds and compositions (U.S. Pat. No. 5,792,771).

Other agents which may be employed in combination with SAgs are steroids such as the angiostatic 4,9(11)-steroids and $C^{21}$-oxygenated steroids (U.S. Pat. No. 5,972,922).

Thalidomide and related compounds, precursors, analogs, metabolites and hydrolysis products (U.S. Pat. Nos. 5,712,291 and 5,593,990) may also be used in combination with SAgs and other chemotherapeutic drugs agents to inhibit angiogenesis. These thalidomide and related compounds can be administered orally.

Certain anti-angiogenic agents that cause tumor regression may be administered together with, or after, intratumoral SAg. These include the bacterial polysaccharide CM101 (currently in clinical trials as an anti-cancer drug) and the antibody LM609. CM101 has been well characterized for its ability to induce neovascular inflammation in tumors. CM101 binds to and cross-links receptors expressed on dedifferentiated endothelium that stimulate the activation of the complement system. It also initiates a cytokine-driven inflammatory response that selectively targets the tumor. CM101 is a uniquely antiangiogenic agent that downregulates the expression VEGF and its receptors. Thrombospondin (TSP-1) and platelet factor 4 (PF4) may also be used together with or after intratumoral SAg. These are both angiogenesis inhibitors that associate with heparin and are found in platelet α granules.

Interferons and metalloproteinase inhibitors are two other classes of naturally occurring angiogenic inhibitors that can be used together with or after intratumoral SAg. Vascular tumors in particular are sensitive to interferon; for example, proliferating hemangiomas are successfully treated with IFNα. Tissue inhibitors of metalloproteinases (TIMPs), a family of naturally occurring inhibitors of matrix metalloproteases (MMPs), can also inhibit angiogenesis and can be used in combination with SAgs.

Pharmaceutical Compositions and Administration

One or more of SAg, SAg homologues, fragments, mutants, fusion proteins and conjugates (SAg agents) are administered by injection, infusion or instillation or implanted intratumorally or subcutaneously in a controlled release formulation. SAg agents are most commonly administered intrathecally in patients with malignant intrathecal fluid accumulation due to primary or metastatic tumors. For example, malignant pleural effusions in patients with lung cancer or metastatic breast, gastric or ovarian cancer. SAg agents may also be administered intrathecally to patients with intrathecal and parenchymal tumor (e.g., involvement of pleura and lung parenchyma) but little or no fluid accumulation in the cavitary space. SAg agents may also be administered intrathecally to patients without malignant involvement or fluid accumulation in the cavitary space or its membranes but with primary or metastatic tumor of the organ (e.g., lung, stomach) and/or lymph nodes. For example, SAg may be administered intrapleurally to patients with primary lung cancer or lung metastases from other primary tumors (e.g., breast, ovary, gastric) without malignant involvement of the pleura or pleural space. In each of the above examples, intrathecal administration of the SAg agents may be administered simultaneously or sequentially with one or more of the SAg agents administered intratumorally, intralymphatically or intravenously.

SAg agents are administered every 3-10 days for up to three months. Dosages of SAg agents used for intrathecal, intratumoral, intralymphatic and intravenous administration range from 0.1 pg-1 ng/kg.

SAg agents are also administered intratumorally to stimulate a T cell-based inflammatory response, including release of tumoricidal cytokines and induction of cytotoxic T cells. The amount of SAg agent administered to a single tumor site ranges from about 0.05-1 ng/kg body weight. The intratumoral dose of a cytotoxic drug administered to the tumor site will generally range from about 0.1 to 500, more usually about 0.5 to 300 mg/kg body weight, depending upon the nature of the drug, size of tumor, and other considerations.

When used to boost the titer of SAg specific antibodies, SAg agents may be incorporated in an adjuvant vehicle such as alum or Freund's incomplete adjuvant. These compositions are administered prior to, during or after intrathecal and/or intratumoral administration of the SAg agent.

They are administered subcutaneously, intramuscularly and intradermally by injection or infusion in doses ranging from 0.1 pg/kg to 1 ng/kg. To induce a maximum immune response, boosters with the SAg agent and vehicle at 1-6 month intervals are given.

The pharmaceutical compositions of the present invention will generally comprise an effective amount of at least a SAg composition dissolved or dispersed in a pharmaceutically acceptable carrier or aqueous medium. Combined therapeutics are also contemplated, and the same type of underlying pharmaceutical compositions may be employed for both single and combined medicaments. The intratumoral composition can be administered to the tumor by needle or catheter via percutaneous entry or via endoscopy, bronchoscopy, culdoscopy or other modes of direct vision including directly at the time of surgery. The composition can be localized into the tumor with CT and/or ultrasound guidance.

With each drug in each tumor, experience will provide an optimum level. One or more administrations may be employed, depending upon the lifetime of the drug at the tumor site and the response of the tumor to the drug. Administration may be by syringe, catheter or other convenient means allowing for introduction of a flowable composition into the tumor. Administration may be every three days, weekly, or less frequent, such as biweekly or at monthly intervals.

The phrases "pharmaceutically or pharmacologically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, general safety and purity standards as required by U.S. Food and Drug Administration. Supplementary active ingredients can also be incorporated into the compositions.

"Unit dosage" formulations are those containing a dose or sub-dose of the administered ingredient adapted for a particular timed delivery. For example, exemplary "unit dosage" formulations are those containing a daily dose or unit or daily sub-dose or a weekly dose or unit or weekly sub-dose and the like.

Injectable Formulations

The SAg composition of the present invention are preferably formulated for parenteral administration, e.g., introduction by injection, infusion or instillation directly into an affected organ cavity (intrathecal administration) or tumor (intratumorally). Means for preparing aqueous compositions that contain the SAg compositions are known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

The SAg compositions can be formulated into a sterile aqueous composition in a neutral or salt form. Solutions as free base or pharmacologically acceptable salts can be prepared in water. Pharmaceutically acceptable salts, include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Suitable carriers include solvents and dispersion media containing, for example, water. In many cases, it will be preferable to include isotonic agents, for example, sugars or sodium chloride.

Sterile injectable solutions are prepared by incorporating the active agents in the required amount in the appropriate solvent with various of the other ingredients enumerated above, as desired, followed by filtered sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active ingredient, plus any additional desired ingredient from a previously sterile-filtered solution thereof.

Suitable pharmaceutical compositions in accordance with the invention will generally include an amount of the SAg composition admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, or most recent edition, incorporated herein by reference. Endotoxin contamination should be kept minimally at a safe level, for example, less that 0.5 ng/mg protein. Moreover, for human administration, preparations should meet sterility, pyrogenicity, general safety and purity standards as required by the U.S. Food and Drug Administration. Upon formulation, the therapeutic compositions are administered in a manner compatible with the dosage formulation and in such amount as is therapeutically effective.

Once in an acceptable pharmaceutical form, SAg are administered intrathecally including but not limited to intrapleurally, intraperitoneally, intra-pericardially, and/or intratumorally and optionally intra-lymph node and/or parenterally (e.g., intravenously, intramuscularly, subcutaneously) by injection or infusion. SAg are also delivered simultaneously or sequentially via one or more routes, e.g., intrapleurally and intravenously or intrapleurally, intratumorally and intravenously. SAg are also administered simultaneously or sequentially in the same or different vehicles, adjuvants and sustained release formulations.

Sustained Release Formulations

SAg formulations are easily administered in a variety of dosage forms, including "slow release" capsules or "sustained release" preparations or devices. Slow release formulations, generally designed to result in a constant drug level over an extended period, are used to deliver a SAg composition as described herein. Such slow release formulations are implanted intrathecally or intratumorally. Controlled release formulations are prepared using polymers to complex or absorb the therapeutic compositions—SAgs, SAg homologues, chemotherapeutic agents or combined formulations of a SAg/homologue and a chemotherapeutic agent(s). The rate of release is regulated by (1) selection of appropriate macromolecules, for example polyesters, polyamino acids, polyvinyl, pyrrolidone, ethylenevinylacetate, methylcellulose, carboxymethylcellulose, and protamine sulfate, (2) the concentration of the macromolecules and (3) the method of incorporation of the active agents into the formulation.

Another method to control the duration of action of the present controlled release preparations is to incorporate the SAgs, SAg homologues and/or chemotherapeutic drugs into particles of a polymeric material such as polyesters, polyamino acids, hydrogels, for example, poly(2-hydroxyethyl-methacrylate) or poly(vinylalcohol); polylactides (e.g., U.S. Pat. No. 3,773,919); copolymers of L-glutamic acid and γ-ethyl-L-glutamate; non-degradable ethylene-vinyl acetate; degradable lactic acid-glycolic acid copolymers, such as the Lupron Depot™ (injectable microspheres of lactic acid-glycolic acid copolymer and leuprolide acetate); and poly-D-(−)-3-hydroxybutyric acid.

Alternatively, instead of incorporating the bioactive/pharmaceutically active agents into polymeric particles, the active agents may rather be entrapped in microcapsules prepared by interfacial polymerization. Examples include hydroxymethylcellulose or gelatin-microcapsules and poly(methylmethacrylate)-microcapsules, respectively, or in colloidal drug delivery systems, for example, liposomes, albumin microspheres, micro emulsions, nanoparticles, and nanocapsules or in macroemulsions. Such techniques are disclosed in Remington's Pharmaceutical Sciences (1980 or most recent edition). Nanoparticles consisting of SAg, SAg homologue and/or chemotherapeutic agents are delivered intrathecally or intratumorally via insufflation using a gas or air propellant.

While polymers such as ethylene-vinyl acetate and lactic acid-glycolic acid enable release of molecules for over 100 days, certain hydrogels release proteins for shorter time periods. For example, it is known that when encapsulated antibodies remain in the body for a prolonged period, they may denature or aggregate as a result of exposure to moisture at 37° C., thus reducing biological activity. Rational strategies are available for stabilization, and they depend on the mechanism involved. For example, if the aggregation mechanism involves intermolecular S—S bond formation through thiodisulfide interchange, stabilization is achieved by modifying sulfhydryl residues, lyophilizing from acidic solutions, controlling moisture content, using appropriate additives, developing specific polymer matrix compositions, and the like.

A particularly attractive sustained release preparation for use herein comprises collagen and an effective amount of SAg (or homologue) and a cytotoxic drug, as described by Luck et al., RE35,748 and Roskos et al., U.S. Pat. No. 6,077,545. More detail on preparation is given in Example 2.

The collagen composition can be used in the treatment of a wide variety of tumors including carcinomas, sarcomas and melanomas. Specific types of tumors include such basal cell carcinoma, squamous cell carcinoma, melanoma, soft tissue sarcoma, solar keratoses, Kaposi's sarcoma, cutaneous malignant lymphoma, Bowen's disease, Wilm's tumor, hepatomas, colorectal cancer, brain tumors; mycosis fungoides, Hodgkin's lymphoma, polycythemia vera, chronic granulocytic leukemia, lymphomas, oat cell sarcoma, etc. The collagen and other composition will be administered to a tumor to provide a cytotoxic amount of drug at the tumor site. The amount of cytotoxic drug administered to the tumor site will generally range from about 0.1 to 500 mg/kg body weight, more usually about 0.5 to 300 mg/kg, depending upon the nature of the drug, size of tumor, and other considerations. Vasoconstrictive agents will generally be present in from 1 to 50% (w/w) of the therapeutic agent. In view of the wide diversity of tumors, nature of tumors, effective concentrations of drug, relative mobility and the like, a definitive range cannot be specified. With each drug in each tumor, experience will provide an optimum level. One or more rounds of administration may be employed, depending upon the lifetime of the drug at the tumor site and the response of the tumor to the drug. Administration may be by syringe, catheter or other convenient means allowing for introduction of a flowable composition into the tumor. Administration may be every three days, weekly, or less frequent, such as biweekly or at monthly intervals.

Illustrative of the manner of sustained administration would be administration of cis-diaminodichloroplatinum (CDDP). Drug concentrations in the sustained release preparation may vary from 0.01 to 50 mg/ml. Injection may be at one or more sites depending on the size of the lesion. Needles of about 1-2 mm diameter are convenient. For multiple injection, templates with predrilled holes may be employed. The drug dose will normally be less than 100 mg/m$^2$ body surface area.

The present invention is particularly advantageous against those tumors or lesions that are clinically relevant because of high frequency. The compositions provide therapeutic gain with tumors greater than 100 mm$^3$, more particularly, greater than 150 mm$^3$, in volume.

Administration by controlled release of SAg and/or a chemotherapeutic drug may be used advantageously in conjunction with other forms of therapy. The tumors or lesions may be irradiated prior and/or subsequent to SAg administration by controlled release. Dose rates may vary from about 20 to 250 rad/min, usually 50 to 150 rad/min, depending on the lesion, period of exposure, and the like. Hyperthermia (heat) may be used as an adjunctive treatment. Treatment will usually involve heating the tumor and its surrounding tissue to a temperature of about 43° for between about 5 and 100 min.

Intratumoral Administration

A SAgs and SETs or a biologically active homologue, fragment or fusion polypeptide or conjugate as described herein is used for direct intratumoral treatment of a tumor mass. SAgs include Staphylococcal enterotoxins A, B, C, D, E, F, G, H, I, J, K, L, M, SpE's, YPM, *M. arthritides, C. perfringens* exotoxin for direct intratumoral treatment of tumor masses. Tumor mass may be those appearing in any organ, palpated or visualized on x-ray, CT scan, MRI or ultrasound. Intratumoral administration may be performed with fluoroscopic, CT or ultrasound guidance.

For intratumoral administration, the dose of a chemotherapeutic drug or biologic agent is preferably reduced 10- to 50-fold below the FDA-recommended dose for parenteral administration. As noted above, a preferred dose of intratumoral Cisplatin is 5-10 mg in 1-5 ml every 7-14 days for 10-40 treatments. This regimen for intratumoral Cisplatin (with or without SAg) is preferred. Preferably Cisplatin is administered together with the SAg in one syringe.

The SAg is dissolved in a conventional vehicle such as saline or it may be incorporated into a controlled release formulation (mixture or suspension) preferably biodegradable. All of the biocompatible and biodegradable and controlled release formulations described herein are useful. These formulations also include but are not limited to, ethylene-vinyl acetate (EVAc: Elvax 40W, Dupont), bioerodible polyanhydrides, polyimino carbonate, sodium alginate microspheres and hydrogels. Dosages used range from 1 ng to 10 mg. The poly-(D-, L- or DL-lactic acid/polyglycolide) copolymers are preferred.

For intratumoral administration, the SAg composition is preferably administered once weekly, and this schedule is continued until the tumor has shrunk significantly. Generally 3-10 treatments are sufficient. In some cases the tumor may appear to expand in size during such intratumoral SAg therapy. This is a result of SAg-stimulated accumulation of inflammatory cells and edema. Despite this enlargement, histological examination of such tumors performed during this phase shows evident tumoricidal effects with inflammatory cell infiltrates.

In the case of an enlarging tumor or a slowly regressing tumor when SAg therapy is given alone, conventional chemotherapy may be administered to promote tumor killing. A chemotherapeutic agent is preferably administered intratumorally alone or together with SAg. Importantly, the chemotherapeutic agent should be given in doses well below those prescribed for systemic use of the same agent. Preferably, intratumoral chemotherapy will comprise use of a selected single agent which is known in the art to be effective against a particular tumor. Moreover, intratumoral combination chemotherapy wherein each agent is given in a reduced dose can also be used. Full-dose or reduced-dose systemic chemotherapy can also be used together with, or shortly after, intratumoral SAg therapy. As with intrathecal administration described herein, intratumoral delivery may be carried out in an outpatient setting as it requires no hospitalization.

The intratumoral therapy with a SAg and or a SAg homologue can be used to treat of a wide variety of neoplastic lesions. Indeed, an improvement in 5-year survival from 16% to 26% of small cell lung cancer was produced by increase in local control accomplished by altering the fractionation of radiation therapy (Turisi et al., N. Eng. J. Med. 340: 265-270 (1999)). Illustrative tumors amenable to intratumoral therapy with SAgs include carcinomas, sarcomas and melanomas, including such as basal cell carcinoma, squamous cell carcinoma, soft tissue sarcoma, solar keratosis, Kaposi's sarcoma, cutaneous malignant lymphoma, Bowen's disease, Wilm's tumor, neuroblastoma, gliomas astrocytomas, hepatoma, colorectal cancer, brain tumors, mycosis fungoides, Hodgkin's lymphoma, polycythemia vera, chronic granulocytic leukemia, lymphomas, oat cell sarcoma, breast carcinoma etc. The intratumoral SAg has particular advantage for tumors or lesions which are among the most important clinically because of their frequency. The compositions and methods disclosed herein provide therapeutic gain with tumors exceeding 100 mm$^3$ in volume, even tumors exceeding 150 mm$^3$.

Superantigens with Radiation Therapy

Local radiation to tumor sites or the mediastinum using the traditional standard dose of 60-65 gy may be given concomitant with intrathecal or intratumoral SAg. The radiotherapy may be also be given before or after the SAg therapy but in either case there should be a hiatus of no more than 30 days between the start of SAg therapy and the start or conclusion of radiotherapy. The median survival of patients given this type of radiotherapy alone is 5% at one year whereas the combined modality improves the median survival to more than two years.

Tumor Models and Procedures for Evaluating Anti-Tumor Effects Studies

The various SAg compositions described herein are tested for therapeutic efficacy in several well established rodent models which are considered to be highly representative of a broad spectrum of human tumors. These approaches are described in detail in Geran, R. I. et al., "Protocols for Screening Chemical Agents and Natural Products Against Animal Tumors and Other Biological Systems (Third Edition)", Canc. Chemother. Reports, Pt 3, 3:1-112, which is hereby incorporated by reference in its entirety.

A. Calculation of Mean Survival Time (MST)

MST (days) is calculated according to the formula:

$$\frac{S + AS_{(A-1)} - (B+1)NT}{S_{(A-1)} - NT}$$

Day: Day on which deaths are no longer considered due to drug toxicity. For example, with treatment starting on Day 1 for survival systems (such as L1210, P388, B16, 3LL, and W256): Day A=Day 6; Day B=Day beyond which control group survivors are considered "no-takes."

S: If there are "no-takes" in the treated group, S is the sum from Day A through Day B. If there are no "no-takes" in the treated group, S is the sum of daily survivors from Day A onward.

S(A-1): Number of survivors at the end of Day (A-1).

Example: for 3LE21, S(A-1)=number of survivors on Day 5.

NT: Number of "no-takes" according to the criteria given in Protocols 7.300 and 11.103.

B. T/C Computed for all Treated Groups $$T/C = \frac{MST \text{ of treated group}}{MST \text{ of control group}} \times 100$$

Treated group animals surviving beyond Day B are eliminated from calculations (as follows):

| No. of survivors in treated group beyond Day B | Percent of "no-takes" in control group | Conclusion |
|---|---|---|
| 1 | Any percent | "no-take" |
| 2 | <10 | drug inhibition |
|   | $^3$10 | "no-takes" |
| $^3$3 | <15 | drug inhibitions |
|   | $^3$15 | "no-takes" |

Positive control compounds are not considered to have "no-takes" regardless of the number of "no-takes" in the control group. Thus, all survivors on Day B are used in the calculation of T/C for the positive control. Surviving animals are evaluated and recorded on the day of evaluation as "cures" or "no-takes."

Calculation of Median Survival Time (MedST)

MedST is the median day of death for a test or control group. If deaths are arranged in chronological order of occurrence (assigning to survivors, on the final day of observation, a "day of death" equal to that day), the median day of death is a day selected so that one half of the animals died earlier and the other half died later or survived. If the total number of animals is odd, the median day of death is the day that the middle animal in the chronological arrangement died. If the total number of animals is even, the median is the arithmetical mean of the two middle values. Median survival time is computed on the basis of the entire population and there are no deletion of early deaths or survivors, with the following exception:

C. Computation of MedST from Survivors

If the total number of animals including survivors (N) is even, the MedST in days is (X+Y)/2, where X is the earliest day when the number of survivors is N/2, and Y is the earliest day when the number of survivors (N/2)−1. If N is odd, the MedST is X.

D. Computation of MedST from Mortality Distribution

If the total number of animals including survivors (N) is even, the MedST in days is (X+Y)/2, where X is the earliest day when the cumulative number of deaths is N/2, and Y is the earliest day when the cumulative number of deaths is (N/2)+1. If N is odd, the MedST is X. "Cures" and "no-takes" in systems evaluated by MedST are based upon the day of evaluation. On the day of evaluation any survivor not considered a "no-take" is recorded as a "cure." Survivors on day of evaluation are recorded as "cures" or "no-takes," but not eliminated from the calculation.

E. Calculation of Approximate Tumor Weight from Measurement of Tumor Diameters with Vernier Calipers The use of diameter measurements (with Vernier calipers) for estimating treatment effectiveness on local tumor size permits retention of the animals for lifespan observations. When the tumor is implanted sc, tumor weight is estimated from tumor diameter measurements as follows. The resultant local tumor is considered a prolate ellipsoid with one long axis and two short axes. The two short axes are assumed to be equal. The longest diameter (length) and the shortest diameter (width) are measured with Vernier calipers. Assuming specific gravity is approximately 1.0, and rounding $\pi$ to 3, the tumor mass (in mg) is calculated by multiplying the length of the tumor (in mm) by the width squared and dividing the product by two:

$$\text{Tumor weight (mg)} = \frac{(\text{length}) \times (\text{width})^2}{2} \text{ or } \frac{L \times (W)^2}{2}$$

The reporting of tumor weights calculated in this way is acceptable inasmuch as the assumptions result in as much accuracy as the experimental method warrants.

F. Calculation of Tumor Diameters

The effects of a drug on the local tumor diameter may be reported directly as tumor diameters without conversion to tumor weight. To assess tumor inhibition by comparing the tumor diameters of treated animals with the tumor diameters of control animals, the three diameters of a tumor are averaged (the long axis and the two short axes). A tumor diameter T/C of 75% or less indicates activity and a T/C of 75% is approximately equivalent to a tumor weight T/C of 42%.

G. Calculation of Mean Tumor Weight from Individual Excised Tumors

The mean tumor weight is defined as the sum of the weights of individual excised tumors divided by the number of tumors. This calculation is modified according to the rules listed below regarding "no-takes." Small tumors weighing 39 mg or less in control mice or 99 mg or less in control rats, are regarded as "no-takes" and eliminated from the computations. In treated groups, such tumors are defined as "no-takes" or as true drug inhibitions according to the following rules:

| Percent of small tumors in treated group | Percent of "no-takes" in control group | Action |
| --- | --- | --- |
| ≦17 | Any percent | no-take; not used in calculations |
| 18-39 | <10 | drug inhibition; use in calculations |
|  | ≧10 | no-takes; not used in calculations |

-continued

| Percent of small tumors in treated group | Percent of "no-takes" in control group | Action |
| --- | --- | --- |
| ≧40 | <15 | drug inhibition; use in calculations |
|  | ≧15 | Code all nontoxic tests "33" |

Positive control compounds are not considered to have "no-takes" regardless of the number of "no-takes" in the control group. Thus, the tumor weights of all surviving animals are used in the calculation of T/C for the positive control (T/C defined above) SDs of the mean control tumor weight are computed the factors in a table designed to estimate SD using the estimating factor for SD given the range (difference between highest and lowest observation). *Biometrik Tables for Statisticians* (Pearson E S, and Hartley H G, eds.) Cambridge Press, Vol. 1, Table 22, p. 165.

II. Specific Tumor Models

A. Lymphoid Leukemia L1210

Summary: Ascitic fluid from donor mouse is transferred into recipient BDF1 or CDF1 mice.

Treatment begins 24 hours after implant. Results are expressed as a percentage of control survival time. Under normal conditions, the inoculum site for primary screening is i.p., the composition being tested is administered i.p., and the parameter is mean survival time. Origin of tumor line: induced in 1948 in spleen and lymph nodes of mice by painting skin with MCA. *J. Natl Cancer Inst.* 13:1328, 1953.

| | |
| --- | --- |
| Animals | One sex used for all test and control animals in one experiment. |
| Tumor Transfer | Inject ip, 0.1 ml of diluted ascitic fluid containing $10^5$ cells |
| Propagation | DBA/2 mice (or BDF1 or CDF1 for one generation). |
| Time of Transfer | Day 6 or 7 |
| Testing | BDF$_1$ (C57BL/6 × DBA/2) or CDF$_1$ (BALB/c × DBA/2) |
| Time of Transfer | Day 6 or 7 |
| Weight | Within a 3-g range, minimum weight of 18 g for males and 17 g for females. |
| Exp Size (n) | 6/group; No. of control groups varies according to number of test groups. |

Testing Schedule

| DAY | PROCEDURE |
| --- | --- |
| 0 | Implant tumor. Prepare materials. Run positive control in every odd-numbered experiment. Record survivors daily. |
| 1 | Weigh and randomize animals. Begin treatment with therapeutic composition. Typically, mice receive 1 μg of the test composition in 0.5 ml saline. Controls receive saline alone. Treatment is one dose/week. Any surviving mice are sacrificed after 4 wks of therapy. |
| 5 | Weigh animals and record. |
| 20 | If there are no survivors except those treated with positive control compound, evaluate |
| 30 | Kill all survivors and evaluate experiment. |

Quality Control ("QC"): Acceptable control survival time is 8-10 days. Positive control compound is 5-fluorouracil; single dose is 200 mg/kg/injection, intermittent dose is 60 mg/kg/injection, and chronic dose is 20 mg/kg/injection.

Ratio of tumor to control (T/C) lower limit for positive control compound is 135%.

Evaluation: Compute mean animal weight on Days 1 and 5, and at the completion of testing compute T/C for all test groups with >65% survivors on Day 5. A T/C value 85% indicates a toxic test. An initial T/C 125% is considered necessary to demonstrate activity. A reproduced T/C 125% is considered worthy of further study. For confirmed activity a composition should have two multi-dose assays that produce a T/C 125%.

B. Lymphocytic Leukemia P388

Summary: Ascitic fluid from donor mouse is implanted in recipient BDF1 or CDF1 mice. Treatment begins 24 hours after implant. Results are expressed as a percentage of control survival time. Under normal conditions, the inoculum site for primary screening is ip, the composition being tested is administered ip daily for 9 days, and the parameter is MedST. Origin of tumor line: induced in 1955 in a DBA/2 mouse by painting with MCA. *Scientific Proceedings, Pathologists and Bacteriologists* 33:603, 1957.

| | |
|---|---|
| Animals | One sex used for all test and control animals in one experiment. |
| Tumor Transfer | Inject ip, 0.1 ml of diluted ascitic fluid containing $10^6$ cells |
| Propagation Time of Transfer | DBA/2 mice (or BDF1 or CDF1 for one generation). Day 7 |
| Testing Time of Transfer | $BDF_1$ (C57BL/6 × DBA/2) or $CDF_1$ (BALB/c × DBA/2) Day 6 or 7 |
| Weight | Within a 3-g range, minimum weight of 18 g for males and 17 g for females. |
| Exp Size (n) | 6/group; No. of control groups varies according to number of test groups. |

Testing Schedule

| DAY | PROCEDURE |
|---|---|
| 0 | Implant tumor. Prepare materials. Run positive control in every odd-numbered experiment. Record survivors daily. |
| 1 | Weigh and randomize animals. Begin treatment with therapeutic composition. Typically, mice receive 1 µg of the test composition in 0.5 ml saline. Controls receive saline alone. Treatment is one dose/week. Any surviving mice are sacrificed after 4 wks of therapy. |
| 5 | Weigh animals and record. |
| 20 | If there are no survivors except those treated with positive control compound, evaluate |
| 30 | Kill all survivors and evaluate experiment. |

Acceptable MedST is 9-14 days. Positive control compound is 5-fluorouracil: single dose is 200 mg/kg/injection, intermittent dose is 60 mg/kg/injection, and chronic dose is 20 mg/kg/injection. T/C lower limit for positive control compound is 135% Check control deaths, no takes, etc.

QC1: Acceptable MedST is 9-14 days. Positive control compound is 5-fluorouracil: single dose is 200 mg/kg/injection, intermittent dose is 60 mg/kg/injection, and chronic dose is 20 mg/kg/injection. T/C lower limit for positive control compound is 135%. Check control deaths, no takes, etc.

Evaluation: Compute mean animal weight on Days 1 and 5, and at the completion of testing compute T/C for all test groups with >65% survivors on Day 5. A T/C value of 85% indicates a toxic test. An initial T/C of 125% is considered necessary to demonstrate activity. A reproduced T/C 125% is considered worthy of further study. For confirmed activity a composition should have two multi-dose assays that produce a T/C 125%.

C. Melanotic Melanoma B16

Summary: Tumor homogenate is implanted ip or sc in BDF1 mice. Treatment begins 24 hours after either ip or sc implant or is delayed until an sc tumor of specified size (usually approximately 400 mg) can be palpated. Results expressed as a percentage of control survival time. The composition being tested is administered ip, and the parameter is mean survival time. Origin of tumor line: arose spontaneously in 1954 on the skin at the base of the ear in a C57BL/6 mouse. *Handbook on Genetically Standardized Jax Mice*. Jackson Memorial Laboratory, Bar Harbor, Me., 1962. See also *Ann NY Acad Sci* 100, Parts 1 and 2, 1963.

| | |
|---|---|
| Animals | One sex used for all test and control animals in one experiment. |
| Propagation Strain | C57BL/6 mice |
| Tumor Transfer | Implant fragment sc by trochar or 12-g needle or tumor homogenate* every 10-14 days into axillary region with puncture in inguinal region. |
| Testing Strain | $BDF_1$ (C57BL/6 × DBA/2) |
| Time of Transfer | Excise sc tumor on Day 10-14 from donor mice and implant as above |
| Weight | Within a 3-g range, minimum weight of 18 g for males and 17 g for females. |
| Exp Size (n) | 10/group; No. of control groups varies according to number of test groups. |

*Tumor homogenate: Mix 1 g or tumor with 10 ml of cold balanced salt solution, homogenize, and implant 0.5 ml of tumor homogenate ip or sc. Fragment: A 25-mg fragment may be implanted sc.

Testing Schedule

| DAY | PROCEDURE |
|---|---|
| 0 | Implant tumor. Prepare materials. Run positive control in every odd-numbered experiment. Record survivors daily. |
| 1 | Weigh and randomize animals. Begin treatment with therapeutic composition. Typically, mice receive 1 µg of the test composition in 0.5 ml saline. Controls receive saline alone. Treatment is one dose/week. Any surviving mice are sacrificed after 8 wks of therapy. |
| 5 | Weigh animals and record. |
| 60 | Kill all survivors and evaluate experiment. |

QC: Acceptable control survival time is 14-22 days. Positive control compound is 5-fluorouracil: single dose is 200 mg/kg/injection, intermittent dose is 60 mg/kg/injection, and chronic dose is 20 mg/kg/injection. T/C lower limit for positive control compound is 135% Check control deaths, no takes, etc.

Evaluation: Compute mean animal weight on Days 1 and 5, and at the completion of testing compute T/C for all test groups with >65% survivors on Day 5. A T/C value of 85% indicates a toxic test. An initial T/C of 125% is considered necessary to demonstrate activity. A reproduced T/C 125% is considered worthy of further study. For confirmed activity a composition should have two multi-dose assays that produce a T/C 125%.

Metastasis after IV Injection of Tumor Cells $10^5$ B16 melanoma cells in 0.3 ml saline are injected intravenously in C57BL/6 mice. The mice are treated intravenously with 1 g of the composition being tested in 0.5 ml saline. Controls receive saline alone. The treatment is given as one dose per week. Mice sacrificed after 4 weeks of therapy, the lungs are removed and metastases are enumerated.

C. 3LL Lewis Lung Carcinoma

Summary: Tumor may be implanted sc as a 2-4 mm fragment, or im as a $2\times10^6$-cell inoculum. Treatment begins 24 hours after implant or is delayed until a tumor of specified size (usually approximately 400 mg) can be palpated. The composition being tested is administered ip daily for 11 days and the results are expressed as a percentage of the control. Origin of tumor line: arose spontaneously in 1951 as carcinoma of the lung in a C57BL/6 mouse. *Cancer Res* 15:39, 1955. See, also Malave, I. et al., *J. Nat'l. Canc. Inst.* 62:83-88 (1979).

| Animals | One sex used for all test and control animals in one experiment. |
|---|---|
| Propagation Strain | C57BL/6 mice |
| Tumor Transfer | Inject cells im in hind leg or implant fragment sc in axillary region with puncture in inguinal region. Transfer on day 12-14 |
| Testing Strain | BDF$_1$ (C57BL/6 × DBA/2) or C3H mice |
| Time of Transfer | Same as above |
| Weight | Within a 3-g range, minimum weight of 18 g for males and 17 g for females. |
| Exp Size (n) | 6/group for sc implant, or 10/group for im implant.; No. of control groups varies according to number of test groups. |

Testing Schedule

| DAY | PROCEDURE |
|---|---|
| 0 | Implant tumor. Prepare materials. Run positive control in every odd-numbered experiment. Record survivors daily. |
| 1 | Weigh and randomize animals. Begin treatment with therapeutic composition. Typically, mice receive 1 µg of the test composition in 0.5 ml saline. Controls receive saline alone. Treatment is one dose/week. Any surviving mice are sacrificed after 4 wks of therapy. |
| 5 | Weigh animals and record. |
| Final day | Kill all survivors and evaluate experiment. |

QC: Acceptable im tumor weight on Day 12 is 500-2500 mg. Acceptable im tumor MedST is 18-28 days. Positive control compound is cyclophosphamide: 20 mg/kg/injection, qd, Days 1-11. Check control deaths, no takes, etc.

Evaluation: Compute mean animal weight when appropriate, and at the completion of testing compute T/C for all test groups. When the parameter is tumor weight, a reproducible T/C of 42% is considered necessary to demonstrate activity. When the parameter is survival time, a reproducible T/C of 125% is considered necessary to demonstrate activity. For confirmed activity a composition must have two multi-dose assays D. 3LL Lewis Lung Carcinoma Metastasis Model This model has been utilized by a number of investigators. See, for example, Gorelik, E. et al., *J. Nat'l. Canc. Inst.* 65:1257-1264 (1980); Gorelik, E. et al., Rec. Results *Canc. Res.* 75:20-28 (1980); Isakov, N. et al., *Invasion Metas.* 2:12-32 (1982) Talmadge J. E. et al., *J. Nat'l Canc. Inst.* 69:975-980 (1982); Hilgard, P. et al., *Br. J. Cancer* 35:78-86 (1977)). Mice: male C57BL/6 mice, 2-3 months old. Tumor: The 3LL Lewis Lung Carcinoma was maintained by sc transfers in C57BL/6 mice. Following sc, im or intra-footpad transplantation, this tumor produces metastases, preferentially in the lungs. Single-cell suspensions are prepared from solid tumors by treating minced tumor tissue with a solution of 0.3% trypsin. Cells are washed 3 times with PBS (pH 7.4) and suspended in PBS. Viability of the 3LL cells prepared in this way is generally about 95-99% (by trypan blue dye exclusion). Viable tumor cells ($3\times10^4$-$5\times10^6$) suspended in 0.05 ml PBS are injected into the right hind foot pads of C57BL/6 mice. The day of tumor appearance and the diameters of established tumors are measured by caliper every two days. Typically, mice receive 1 µg of the composition being tested in 0.5 ml saline. Controls receive saline alone. The treatment is given as one or two doses per week.

In experiments involving tumor excision, mice with tumors 8-10 mm in diameter are divided into two groups. In one group, legs with tumors are amputated after ligation above the knee joints. Mice in the second group are left intact as non-amputated tumor-bearing controls. Amputation of a tumor-free leg in a tumor-bearing mouse has no known effect on subsequent metastasis, ruling out possible effects of anesthesia, stress or surgery. Surgery is performed under Nembutal anesthesia (60 mg veterinary Nembutal per kg body weight).

Determination of Metastasis Spread and Growth

Mice are killed 10-14 days after amputation. Lungs are removed and weighed. Lungs are fixed in Bouin's solution and the number of visible metastases is recorded. The diameters of the metastases are also measured using a binocular stereoscope equipped with a micrometer-containing ocular under 8× magnification. On the basis of the recorded diameters, it is possible to calculate the volume of each metastasis. To determine the total volume of metastases per lung, the mean number of visible metastases is multiplied by the mean volume of metastases. To further determine metastatic growth, it is possible to measure incorporation of $^{125}$IdUrd into lung cells (Thakur, M. L. et al., *J. Lab. Clin. Med.* 89:217-228 (1977). Ten days following tumor amputation, 25 mg of FdUrd is inoculated into the peritoneums of tumor-bearing (and, if used, tumor-resected mice. After 30 min, mice are given 1 mCi of $^{125}$IdUrd. One day later, lungs and spleens are removed and weighed, and a degree of $^{125}$IdUrd incorporation is measured using a gamma counter.

Statistics: Values representing the incidence of metastases and their growth in the lungs of tumor-bearing mice are not normally distributed. Therefore, non-parametric statistics such as the Mann-Whitney U-Test may be used for analysis.

Study of this model by Gorelik et al. (1980, supra) showed that the size of the tumor cell inoculum determined the extent of metastatic growth. The rate of metastasis in the lungs of operated mice was different from primary tumor-bearing mice. Thus in the lungs of mice in which the primary tumor had been induced by inoculation of large doses of 3LL cells ($1$-$5\times10^6$) followed by surgical removal, the number of metastases was lower than that in nonoperated tumor-bearing mice, though the volume of metastases was higher than in the nonoperated controls. Using $^{125}$IdUrd incorporation as a measure of lung metastasis, no significant differences were found between the lungs of tumor-excised mice and tumor-bearing mice originally inoculated with $10^6$ 3LL cells. Amputation of tumors produced following inoculation of $10^5$ tumor cells dramatically accelerated metastatic growth. These results were in accord with the survival of mice after excision of local tumors. The phenomenon of acceleration of metastatic growth following excision of local tumors had been observed by other investigators. The growth rate and incidence of pulmonary metastasis were highest in mice inoculated with the lowest doses ($3 \times 10^4$-$10^5$ of tumor cells) and characterized also by the longest latency periods before local tumor appearance. Immunosuppression accelerated metastatic growth, though nonimmunologic mechanisms participate in the control exerted by the local tumor on lung metastasis development. These observations have implications for the prognosis of patients who undergo cancer surgery.

E. Walker Carcinosarcoma 256

Summary: Tumor may be implanted sc in the axillary region as a 2-6 mm fragment, im in the thigh as a 0.2-ml inoculum of tumor homogenate containing $10^6$ viable cells, or ip as a 0.1-ml suspension containing $10^6$ viable cells. Treatment of the composition being tested is usually ip. Origin of tumor line: arose spontaneously in 1928 in the region of the mammary gland of a pregnant albino rat. *J. Natl Cancer Inst* 13:1356, 1953.

| Animals | One sex used for all test and control animals in one experiment. |
|---|---|
| Propagation Strain | Random-bred albino Sprague-Dawley rats |
| Tumor Transfer | S.C. fragment implant is by trochar or 12-g needle into axillary region with puncture in inguinal area. I.m. implant is with 0.2 ml of tumor homogenate (containing $10^6$ viable cells) into the thigh. I.p. implant is with 0.1 ml suspension (containing $10^6$ viable cells) Day 7 for im or ip implant; Days 11-13 for sc implant |
| Testing Strain | Fischer 344 rats or random-bred albino rats |
| Time of Transfer | Same as above |
| Weight | 50-70 g (maximum of 10-g weight range within each experiment) |
| Exp Size (n) | 6/roup; No. of control groups varies according to number of test groups. |

| Test system | Prepare drug on day: | Administer drug on days: | Weigh animals on days | Evaluate on days |
|---|---|---|---|---|
| 5WA16 | 2 | 3-6 | 3 and 7 | 7 |
| 5WA12 | 0 | 1-5 | 1 and 5 | 10-14 |
| 5WA31 | 0 | 1-9 | 1 and 5 | 30 |

In addition the following general schedule is followed

| DAY | PROCEDURE |
|---|---|
| 0 | Implant tumor. Prepare materials. Run positive control in every odd-numbered experiment. Record survivors daily. |
| 1 | Weigh and randomize animals. Begin treatment with therapeutic composition. Typically, mice receive 1 µg of the test composition in 0.5 ml saline. Controls receive saline alone. Treatment is one dose/week. Any surviving mice are sacrificed after 4 wks of therapy. |
| Final day | Kill all survivors and evaluate experiment. |

QC: Acceptable i.m. tumor weight or survival time for the above three test systems are: 5WA16: 3-12 g.; 5WA12: 3-12 g.; 5WA31 or 5WA21: 5-9 days.

Evaluation: Compute mean animal weight when appropriate, and at the completion of testing compute T/C for all test groups. When the parameter is tumor weight, a reproducible T/C 42% is considered necessary to demonstrate activity. When the parameter is survival time, a reproducible T/C 125% is considered necessary to demonstrate activity. For confirmed activity F. A20 Lymphoma $10^6$ murine A20 lymphoma cells in 0.3 ml saline are injected subcutaneously in Balb/c mice. The mice are treated intravenously with 1 g of the composition being tested in 0.5 ml saline. Controls receive saline alone. The treatment is given as one dose per week. Tumor growth is monitored daily by physical measurement of tumor size and calculation of total tumor volume. After 4 weeks of therapy the mice are sacrificed.

Having now generally described the invention, the same will be more readily understood through reference to the following examples which are provided by way of illustration, and are not intended to be limiting of the present invention, unless specified.

INTRODUCTION TO EXAMPLES

Prior to the present invention, those skilled in the art were not inclined to consider administering SAgs intrathecally into the pleural space in patients with MPE (or intratumorally into patients with malignant lung or brain nodules.) This is because published studies (Terman et al., et al., *N. Engl. J. Med.* 305:1195-2000 (1981); Young et al., *Am. J. Med.* 75:278-88 (1983)) had shown that SEB (together with protein A) administration to patients with metastatic breast cancer resulted in severe pulmonary toxicity which manifested as objectively confirmed acute respiratory distress syndrome (ARDS) with hypoxemia (due to non-cardiogenic pulmonary edema). The hypoxemia was worse in a patient with preexisting metastatic lung tumor who also developed severe bronchospasm and a large pleural effusion requiring repeated thoracenteses. This strong reaction prompted the above authors to warn that SEB treatment should not be carried out in patients with pulmonary metastases (Terman, D S *CRC Crit. Rev. Oncol. Hematol.* 4:103-24 (1985)). Moreover, pathology studies of primates infused with SEB showed a tendency for the protein to localize in the pulmonary vasculature injuring endothelial cells and causing pulmonary edema (Finegold M J, *Lab. Invest.* 16:912-924 (1967)). Based on the foregoing, a person of ordinary skill in the art would have concluded that administration of a SAg directly into the pleural space to treat an MPE was contraindicated because it was liable to exacerbate the effusion and induce life threatening hypoxemia and bronchospasm.

Surprisingly, as presented below, the present inventor discovered that, notwithstanding the earlier results cited above that taught away from intrapleural and intratumoral administration of SAgs, intrathecal administration and intratumoral administration of SEs directly into the pleural space resulted in successful treatment of patients with MPE (intrathecal=intrapleural) and disappearance of a large lung carcinoma (intratumoral). Indeed, all twelve of the first patients with MPE treated in this manner showed complete regressions of their pleural effusions with minimal toxicity. A patient treated with a large lung adenocarcinoma treated with intratumoral SAg and low dose cisplatin showed a complete regression of his tumor. Importantly, Examples 1 and 2 prove that a native SAg, not combined with a tumor specific antibody as is taught in the prior art, is an effective antitumor therapeutic agent.

Example 1

Intrathecal (Intrapleural) Injection of SEC in Patients with Malignant Pleural Effusions Methods Patients: From February 1999 to October 2002, 14 consecutive patients with NSCLC and MPE were evaluated. Twelve were considered to be evaluable for response and ten for survival. Patins were required to have NSCLC with at least a 350 ml effusion. Chemotherapy, radiation and all other biological response modifying agents with antitumor activities were discontinued at least a month before starting treatment. Patients that had been treated with prior intrapleural chemotherapy, pleurodesis, lobectomy or pneumonectomy on the affected side were excluded. Pleural effusions were diagnosed by chest radiographs, chest CT and ultrasonography. The diagnosis of MPE was established by positive pleural fluid cytology. In two patients, cytology of pleural fluid examined 24 hours after treatment showed evidence of tumor killing.

Before each course of treatment, the patients received a complete physical examination, ECG, respiratory function tests, CBC, serum biochemistry tests, and urinalysis. Each patient had a chest radiogram and sonogram of the pleural fluid before starting treatment to document the presence of pleural fluid. Blood and pleural effusion samples were obtained by venipuncture and thoracentesis, respectively, before and 6 hours after selected procedures. Chest radiograms and sonograms were obtained for every case monthly until the completion of the study. Patients were also screened continuously for side effects which were graded according to the World Health Organization toxicity scale. Palliative radiotherapy was permitted as long as it was not directed at the involved pleura. Karnofsky performance status (KPS) was recorded for all patients but was not a criterion for eligibility in the trial.

Treatment: Staphylococcal enterotoxin C (SEC) 2 ng/ml was used. SEC induced mitogenesis in peripheral blood mononuclear cell in doses below 10 pg/ml. Thoracentesis was performed after sonographic localization of the pleural effusion. Once MPE was demonstrated, thoracentesis was carried out with complete removal of the pleural effusion. With the patient in the sitting position, the entry site was cleaned with aseptic solution and the skin infiltrated with 2% lidocaine. The needle was directed into the intercostal space just above the rib. A small skin incision was made, and an 18-gauge needle was introduced into the pleural space. Fluid was withdrawn through a three-way stopcock. Following thoracentesis and complete evacuation of the pleural effusion, SEC at 20 to 40 nanograms in 10-20 ml of diluent were gently injected into the pleural cavity through the same thoracentesis needle. Patients were instructed to rest for 24 hours and were monitored for the appearance of new symptoms and changes in vital signs.

Patients were followed daily for recurrence of pleural fluid by physical examination and ultrasound and chest radiography. Thoracentesis and SEC injection were repeated every 3-7 days until there was no further re-accumulation of pleural fluid. In general, patients required an average of 3-4 treatments to achieve remission, Evaluation of Responses: Complete response (CR) was defined as the absence of pleural fluid re-accumulation confirmed by chest radiographs and sonography without the need for thoracentesis for >4 weeks. A partial response (PR) was defined as a decrease of ~50% of pretreatment pleural effusion volume and no appearance of new effusions over a period of >4 weeks. Short term responses were recorded at 30 days and long term responses at 90 days after completing SEC treatment. No response (NR) was defined as less than a 50% decrease in pleural effusion volume. Progressive disease was defined as was at least a 25% increase in the effusion volume above pretreatment levels.

SEC treatments were continued every 3-7 days until there was no significant pleural fluid reaccumulation. The patients were then observed monthly for pleural fluid reaccumulation using ultrasound and/or chest radiography. The following were not considered treatment failures: blunting of the costo-diaphragmatic angles, pleural reaction and small amounts of loculated pleural fluid detected on ultrasound that was inaccessible to thoracentesis.

Statistical Evaluation of Survival: The S-Plus statistical software package (Professional Edition 6 for Windows, Insightful Corporation, Seattle, Wash.) was used to evaluate survival based on measurements from first day of enterotoxin treatment. Kaplan Meir survival curves were derived with the survival analysis program developed at the Mayo Clinic and incorporated in the S-Plus package. Estimates of survival probabilities, MedST and the variance of MedST were obtained from the SEC treated group and from comparative groups. A log rank test was performed comparing the SEC treatment group with a control group and to compare two different drug administration protocols. The Wilcoxon rank sum statistic was used to test the comparison of Karnofsky scores between two groups. The relation of the level of pleural effusion to survival was analyzed using the Cox proportional hazards model.

Hematologic Studies: Complete blood counts in the peripheral blood and pleural fluid were obtained before and 6-24 hours after SEC treatment in all patients.

Results

Patient Characteristics: Fourteen consecutive patients with NSCLC were considered for the study, 12 of which were evaluable for response and 10 for survival. Two patients were excluded from data for response and survival. The first had received intrapleural chemotherapy before this treatment and the second had a prior pneumonectomy on the affected side. Two additional patients were evaluable for response but were lost to long-term followup (therefore unevaluable for survival). Patient demographics are shown in Table 4. Of the 12 evaluable patients all were males, median age was 68 years (46-82). The NSCLC consisted of 9 adenocarcinomas and 3 squamous cell carcinomas. Pleural effusions were unilateral in 11 patients, bilateral in one and associated with ascites and pericardial effusion in two and one patient respectively. The median initial volume of the pleural effusions was 575 ml (350-1100 ml). The median pretreatment Karnofsky performance status (KPS) was 45 (30-60) (Table 4).

Dose, Schedule and Route of Administration

In all patients, SEC was delivered intrapleurally immediately after thoracentesis in doses ranging from 20-40 ng. In general, the procedure was repeated every 3-7 days. A total of 45 intrapleural treatments with SSEC were administered. The mean number of IP treatments required before significant fluid reaccumulation ceased was 3.8±1.3. Along with intrapleural SEC, five patients also received SEC IV daily for 30, 21 14, 6 and 3 days respectively commencing at the same time as the first intrapleural administration of SEC. Tables 5 shows the SEC dosage and duration of remission in each of the 12 evaluable patients.

TABLE 4

Patient Demographics

| Characteristics | Numbers/values |
|---|---|
| No. of evaluable patients | 12 |
| Response | 12 |
| Survival | 10 |
| Gender | all 12 male |
| Mean Age in years (range) | 64.8 (46-82) |
| KPS - mean (range) | 45 (20-60) |
| Primary Lung Tumors | 12 |
| Non Small Cell Lung Carcinomas (NSCLC) | 11 |
| Adenocarcinoma | 9 |
| Squam. cell carcinoma | 3 |
| Mean Initial Size of Effusion in ml (range) | 595 (350-1100) |

TABLE 5

Recurrence of Malignant Pleural Effusions in Patients After Intrapleural SSEC

| NSCLC Pt # age/gender | Prior Therapy | SEC Regimen dose, freq., duration | Response & Duration After Therapy |
|---|---|---|---|
| 1. 82/M | Radio-therapy | 25 ng IP Q1 wk × 3 wk. 50 ng IP Q1 wk × 3 wk. 10 ng IV QED × 30 days | No recurrent effusion 26 mo. |
| 2. 67/M | Radio-therapy | 25 ng IP Q1 wk × 4 wk. 5 ng IV QED × 21 days | No recurrent effusion 11 mo. |
| 3. 66/M | | 25 ng IP Q1 wk × 4 wk. | Minimal effusion 15 Mo |
| 4. 61/M | Intra-pleural cytoxan | 25 ng IP Q1 wk × 4 wks 5 ng IV QD × 14 days | No recurrent effusion 7 mo. |
| 5. 47/M | | 20 ng IP I wk × 3 | No recurrent effusion 5 mo (suicide) |
| 6. 73/M | Radio-therapy | 25 ng IP Q 3-4 days × 5 | No recurrent effusion 8 mo. |
| 7. 68/M | | 25 ng IP Q 3-4 days × 4 | No recurrent effusion 6 mo |
| 8. 69/M | | 25 ng IP Q 1 wk × 3 | No recurrent effusion 7 mo. |
| 9. 56/M | | 25 ng IP Q 3-4 days × 5 10 ng IV QD × 21 days | No recurrent effusion 7 mo |
| 10. 65/M | | 25 ng IP Q 3-4 days × 3 10 ng IV QD × 14 days | No recurrent effusion 5 mos |
| 11. 46/M | | 25 ng IP × 1 10 ng IV QD × 3 days | Minimal pleural fluid 3 mo. Lost to followup |
| 12. 78 M | | 25 ng IP Q3-4 days × 3 | No recurrent effusion 5 mo. Lost to followup |

Responses: Twelve patients were evaluable for response, i.e., recurrence of pleural effusion following the last SEC treatment. Eleven had a complete response and 1 had a partial response. All 12 patients, showed no recurrent effusion more than 90 days after their last SEC treatment. One month after treatment, the median pretreatment KPS of 45 (30-60) improved to a median KPS of 70 (60-90) (p<0.05) in association with resolution of the effusions. In patient #1, a left pleural effusion recurred 6 month after his first SEC treatment. He was retreated with SEC IP Q 3-4 days×4 after which the effusion resolved and has not recurred. He has been in a disease free status for 20 months after his last treatment and is alive 25 months from the first SEC treatment (Table 5). Sixteen months after starting therapy, patient #4 had a recurrent symptomatic pleural and pericardial effusion of moderate size on ultrasound. Within two weeks of treatment with two SEC instillations symptoms remitted as did the pleural and pericardial effusions. However, the patient refused additional treatment and hence the effect of this limited retreatment could not be evaluated. Effusions did not reappear in patients #2 and #5 until death 11.5 and 8 months respectively after starting SEC treatment.

Figure 2:
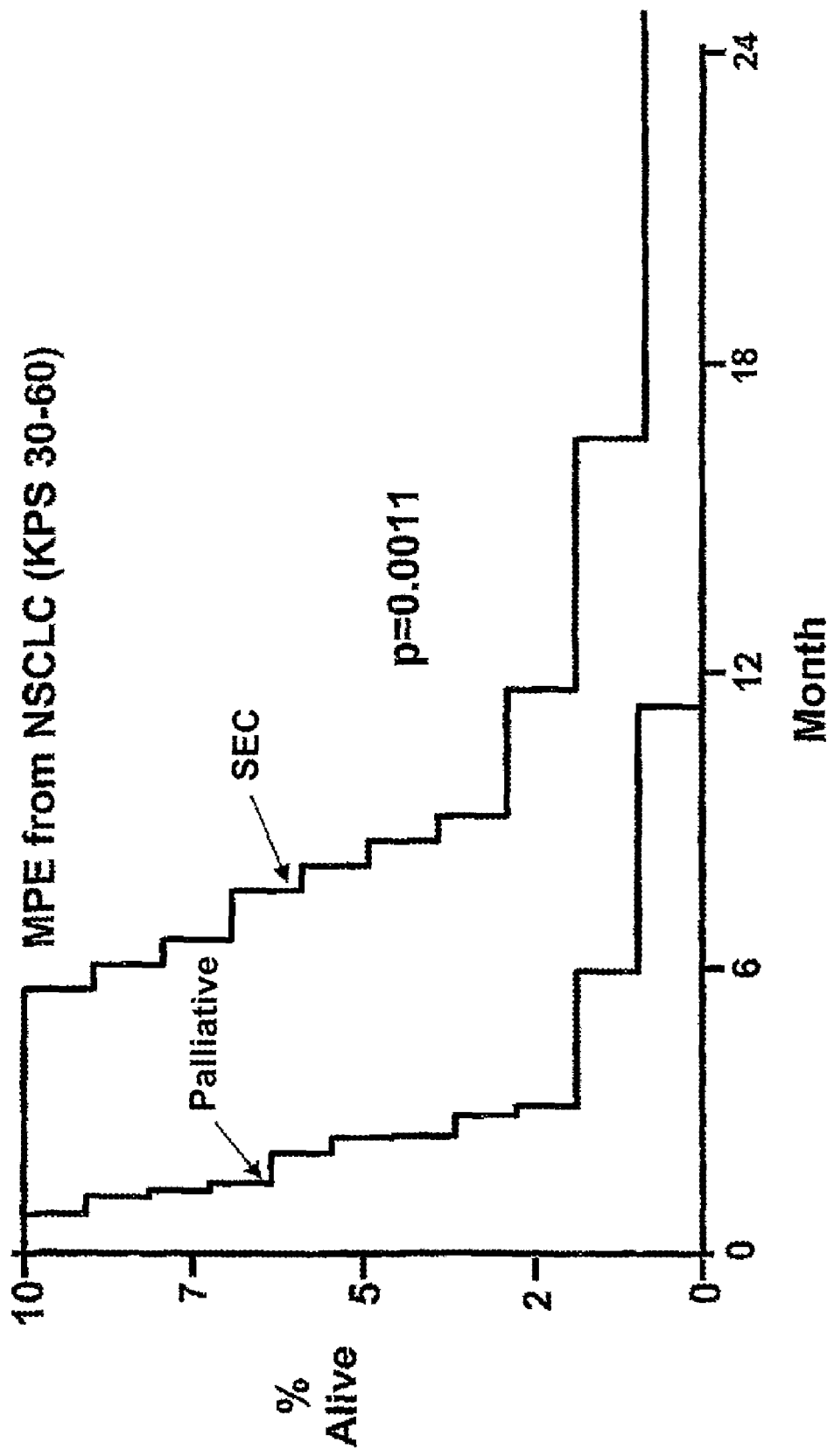
FIG. 2 shows Kaplan-Meir survival curve of all patients in SEC-treated group with KPS range of 30-60 compared to a subset of patients from the control group in FIG. 1A with the same KPS range 30-60. Median KPS for the SEC and control groups were 45 and 43 respectively (p=0.8) yet the SEC-treated group showed a significantly prolonged survival (p=0.014).

Survival: Survival data is displayed in Table 6. Ten patients were evaluable for survival. Median pretreatment KPS was 45 (30-60). The median survival for the 10 evaluable patients in the SSEC-treated group was 8.25 months. This was compared to the median survival of 2.4 months for control group comprising 21 consecutive current control patients with MPE from NSCC treated with talc pleurodesis at University of California San Diego from 1993-1998 (p=0.0096) (FIG. 1). Eleven patients from the latter group with pretreatment KPS and distribution comparable to the SSEC-treated group (p=0.8) had a median survival of 2.4 months (p=0.0014) (FIG. 2). Patients in the SEC-treated group survived on the order of 3.6 fold longer than talc pleurodesis-treated controls (FIGS. 1 & 2). Three patients in the SEC-treated group survived for 350 days or more with one patient still alive 26 months after starting therapy while no patients survived longer than 342 days among the 11 patients the talc-treated control group (FIG. 2). Survival in the SEC group could not be predicted from pretreatment pleural volume (p=0.15).

Application to Other Tumors: SEC was given to intrapleurally to three patients with MPEs from small cell carcinoma of the lung, uterine sarcoma and melanoma respectively according to the same protocol for NSCLC patients. Two patients (small cell carcinoma and uterine sarcoma) had prior chemotherapy. All three showed complete resolution of their malignant effusions lasting 3, 1.5 and 4 months respectively. Toxicity was minimal.

Hence, in view of the broad range of tumors shown to be responsive to intrathecal SEC, it would be fully expected that the SEC therapy would produce objective anti-tumor effects against substantially all malignancies irrespective of origin exhibiting a malignant pleural effusion.

TABLE 6

Survival of Patients Treated with Intrapleural Superantigen Staphylococcal Enterotoxin C (SEC)

| NSCLC Pt. # Age/Gender (unique Pt ID) | Initial Pleural Fluid Volume (ml) | KPS* Pre/post | Survival (months)** |
|---|---|---|---|
| 1. 82/M (#175414) | 1100 | 30/90 | 26 (Alive) |
| 2. 67/M (#167251) | 350 | 40/70 | 11.5 (Dead) |
| 3. 66/M (#181383) | 550 | 50/90 | 16.5 (Dead) |
| 4. 61/M (#179918) | 700 | 40/60 | 8.5 (Dead) |
| 5. 47/M (#171024) | 350 | 60/70 | 6 (Dead) |
| *6. 73/M (#185507) | 400 | 40/80 | 9 (Dead) |
| 7. 68/M (#185938) | 600 | 60/90 | 6.5 (Dead) |
| 8. 69/M (#189953) | 600 | 50/60 | 8 (Dead) |
| 9. 56/M/NSCC | 600 | 40/70 | 7.5 (Dead) |
| 10. 65/M/ | 380 | 50/60 | 5.5 (Dead) |
| Median: 68.0 yrs | 575 | 45/70 | 8.25 |

*Karnofsky Performance Status
**Survival measured from date of first treatment

TABLE 7

Complications of SEC Treatment

| Complication | (no. of patients) |
|---|---|
| Fever >38° C. | 6 |
| Chills | 2 |
| Pain | 3 |
| Dyspnea | 0 |
| Leukopenia | 0 |
| No toxicity | 6 |

Toxicity

Adverse effects associated with SSEC treatment are shown in Table 7. In general the SEC was well tolerated. The most common adverse effect was fever ranging from 37.4°-39.8° C. that was unrelated to dosage. Fever reached 38° C. in 5 patients and 39.8° C. in 6 and lasted for 24-36 hours. However in 2 patients, it lasted more than 36 hours and was relieved by indomethacin suppository. Minimal pleuritic chest pain ipsilateral to the effusion occurred in 3 patients and abated spontaneously. There was no evidence of respiratory distress, congestive heart failure and no significant changes in hepatic or renal function during or after treatment. No stage 3 or 4 ltoxicity was observed in any case.

Hematologic Changes in the Blood and Pleural Fluid

Peripheral blood white blood cell, neutrophil and lymphocyte counts increased slightly but consistently six hours after treatment in all patients studied (see Table 8. Likewise, total leukocyte, neutrophil and lymphocyte counts in pleural effusions increased significantly 6 hours after treatment.

TABLE 8

Hematologic Changes in Blood and Effusions of Patients Treated with Intrapleural SEC

| | WBC ($10^9$/L) | Neutrophil ($10^9$/L) | Lymphocytes ($10^9$/L) |
|---|---|---|---|
| Peripheral Blood | | | |
| Pre-treatment | 5.200 ± 0.398 | 3.285 ± 2.50 | 1.850 ± 0.144 |
| Post-treatment | 8.533 ± 1.534* | 6.455 ± 1.535* | 1.916 ± 0.587 |
| Pleural Effusion | | | |
| Pre-treatment | 0.761 ± 0.150 | 0.553 ± 0.150 | 0.201 ± 0.134 |
| Post-treatment | 1.178 ± 0.381* | 0.661 ± 0.185* | 0.541 ± 0.167* |

*significant at $p < 0.05$

Peripheral blood and pleural effusion leukocyte counts before and 6-24 hour after the initial SSEC treatment. Significant increases in leukocyte and neutrophil counts were noted in blood and pleural fluid. Lymphocyte counts were significantly elevated post-treatment only in the pleural fluid.

Discussion

In general, these results for survival and responses (control of pleural effusion) suggest that SEC was not only palliating the symptoms of MPE but also exerted a therapeutic effect on the patient's tumor. This occurred in the absence of significant clinical or serologic toxicity. These results show that intrapleural administration of SEC in patients with MPE can eliminate pleural fluid reaccumulation for more than 90 days and, in several cases, for as long as 6, 8, 12 and 15 months. The response rate (100%) for clearance of MPE exceeded that for agents now in common use for palliation of MPEs, namely talc, bleomycin and doxycycline.

A substantial number of the patients receiving SEC treatment survived longer than would be expected than if the SEC were only palliative. The MST of 8.25 months in the 10 NSCLC patients included 3 patients who survived more than 350 days. At the time these results were last analyzed, one patient was still alive 26 months after starting treatment. In contrast, 21 patients with MPE from NSCLC who were treated with talc pleurodesis at the Univ. of California, San Diego (UCSD) from 1993-1998 showed a MST of 2.5 months (Burroughs et al., Chest 117:73-78 (2000)). Eleven patients from the latter group with comparable pretreatment KPS to the SEC-treated group had a median survival of 2.4 months. Both groups had a statistically similar distribution of KPS yet the SEC-treated group had a median survival on the order of 3 fold longer than controls and a 1 year survival of 20% compared to 0% for controls.

An additional group of 61 patients with MPE from NSCLC treated with catheter drainage and chemical pleurodesis at M.D. Anderson Cancer Center from 1994-1996 had a median survival of 2.0 months (Putnam et al., Ann. Thorac. Surg. 69: 369-375 (2000). The improved survival in the SEC group could not be attributed to higher pretreatment KPS scores since the median pretreatment KPS for the SEC-treated 10 patients was 45 compared to >70 in the palliative-treatment control group. Despite the lower pretreatment KPS, the SEC-treated group had an extension of their MST on the order of 4 fold compared to controls. Hence, compared to current historical controls treated with the best available palliative regimens (talc, doxycycline, catheter drainage), the SEC-treated patients of the present study survived significantly longer.

Moreover, as noted by others, initial pleural fluid volume was not predictive of improved survival. Indeed, the longest survivor had only the fifth largest initial pleural effusion.

The observed SEC-induced MST of 8.25 months (a) exceeded the 7.6 month MST observed in a study of 262 stage 1V lung cancer patients receiving the best single agent chemotherapy (cisplatin) and (b) was comparable to the 8.6 month MST in patients receiving the best combination chemotherapy (cisplatin+gemcitabine).

In contrast to talc, bleomycin, doxycycline and catheter drainage, SEC treatment does not require thoracotomy, chest tube insertion or in-hospital tube drainage. The SEC treatment was performed in the office by thoracentesis followed by instillation of SEC into the pleural space. In general, SEC treatment induced minimal side effects and toxicity. In particular, there was no dyspnea, pulmonary edema or acute respiratory distress syndrome as has been observed rarely following talc insufflation or instillation. As a safe outpatient procedure, SEC therapy appears to offer considerable cost reduction compared to the presently available agents which while also providing symptomatic relief and a significant survival benefit. Table 9 shows the comparative cost effectiveness with palliative treatments.

TABLE 9

| TREATMENT | AGENT COST OF TREATMENT | TOTAL COST | COST DRIVERS |
|---|---|---|---|
| Talc insufflation | $ 0.15-0.50 (2.5-10 g) | $30,996 | OR Facilities, Thoracic Surgeon, Respiratory Therapy, |

TABLE 9-continued

| TREATMENT | AGENT COST OF TREATMENT | TOTAL COST | COST DRIVERS |
|---|---|---|---|
| Talc slurry | $ 0.15-0.50 (2.5-10 g) | $25,000 | Hospitalization, Indwelling Chest Tube, Complications (ARDS) Hospital days, Respiratory Therapy, Indwelling Chest Tube, Complications |
| Bleomycin | $1104 | $20,000 | High Agent cost, Hospitalization, Indwelling Chest Tube, Toxicity Potential with Chemotherapy Low Response Rate, High Recurrence Rate |
| SEC Superantigen | $300 | $2000-$10,000 | NONE of the following: OR facility Thoracic Surgeon, Hospitalization, Respiratory Therapy, Indwelling Chest Tube & Drainage, |

Patients with MPEs from small cell carcinoma of the lung, uterine sarcoma and melanoma were treated with intrapleural SEC and showed resolution of their MPEs for 1.5-4 months. Thus, it would be expected that SEC therapy is applicable to a substantial number of malignant pleural effusions from tumors other than NSCLC.

While SEC therapy is effective against symptomatic MPEs as given above, it is also applicable to patients with small asymptomatic malignant pleural effusions irrespective of origin or initial pleural fluid volume. In lung cancer in particular, the presence of a malignant pleural effusion portends a prognosis of two months survival (irrespective of initial effusion volume). Thus, small symptomatic or asymptomatic MPEs originating from lung, breast, stomach, esophagus, colon, kidneys, ovary, uterus (or any other origin) as well as melanoma, lymphomas and mesotheliomas would be expected to benefit from this treatment which will prolong survival in these groups.

Example 2

Treatment of Lung Adenocarcinoma by Intratumoral Injection of SEA Followed by Intratumoral Chemotherapy Patient and Treatment Plan The patient is a 75 year old man with a large adenocarcinoma in the left midlung field.

He received intratumoral administration of SEC (5 ng) once weekly for 7 weeks. During weeks 8-11, the patient received weekly intratumoral injections of SEA (5 ng) together with cisplatin (10 mg). Chest x-rays were done before treatment and 1 week after the conclusion of the last dose of intratumoral SEC/cisplatin.

Criteria for response are as set forth by the International Union Against Cancer and are given in more detail below. Briefly, a complete response is defined as no measurable disease. A partial response is defined as a 50% reduction of the bidirectional diameter of measurable tumor.

Results: One week after concluding the course of intratumoral SEAC followed by intratumoral SEA+cisplatin, the patient's chest x-ray and CT scan showed complete disappearance of the pulmonary nodule which measured 20 cm$^3$ before commencing treatment. The lesion showed progressive reduction in size on ultrasound during the SEA treatment phase. Morbidity consisted of a low grade temperature for 3-4 weeks after commencing SEC therapy, fatigue and anorexia not requiring treatment. These symptoms abated with continued treatment. CBC, renal and liver functions tests did not change significantly after treatments.

Discussion

A SAg administered alone intratumorally for 7 weeks followed by a 3 week course of a combination of the SAg and low dose cisplatin, given intratumorally, induced complete remission. The dose of cisplatin used is more than 10-fold lower than the mean recommended dose administered systemically per cycle. Side effects of the SEA treatment were minimal, and cisplatin caused no toxicity. This patient subsequently received two cycles of systemic cisplatin and mitomycin C and remains in complete remission 7 months later.

Example 3

Clinical Trial of Intratumoral SAg and Low Dose Chemotherapy in Humans Patients

All patients treated have histologically confirmed malignant masses confirmed by biopsy or cytology are entered. Malignant diseases including carcinomas, sarcomas, melanomas, gliomas neuroblastomas, lymphomas and leukemia. The malignant disease has failed to respond or is advancing despite conventional therapy. Patients in all stages of malignant disease involving any organ system are included. Staging describes both tumor and host, including organ of origin of the tumor, histologic type, histologic grade, extent of tumor size, site of metastases and functional status of the patient. For a general classification includes the known ranges of Stage 1 (localized disease) to Stage 4 (widespread metastases), see Abraham J et al., *Bethesda Handbook of Clinical Oncology*, Lippincott, Williams & Wilkins, Philadelphia, Pa., 2001. Patient history is obtained and physical examination performed along with conventional tests of cardiovascular and pulmonary function and appropriate radiologic procedures. The malignant masses are visible on x-ray or CT scan and are measurable with calipers. They have not been undergoing any other anticancer treatment for at least one month and have a clinical KPS of at least 50.

SEA is used as the prototypical SAg (but other SAgs and homologues as described herein are used in other patients in comparable doses, yielding similar results). SEA is administered intratumorally in doses of 0.05-1 ng/kg intratumorally once every 2-7 days. The tumors are injected under direct vision at surgery, bronchoscopy, endoscopy, peritoneoscopy, culdocopy. They are accessible to percutaneous injection with CT, ultrasound or stereotaxis used to localize and guide the injected composition into the tumor.

Intratumoral chemotherapy preferably comprises the use of a selected single agent which is known in the art to be effective against a particular tumor. Intratumoral combination chemotherapy wherein each agent is given in a reduced dose can also be used. Total intratumoral dose of a chemotherapeutic agent per cycle is 3-7 fold below that of the mean recommended dose of a systemic chemotherapeutic agent per cycle. Recommended mean dosages for single and individual chemotherapeutic agents for human tumors are well known in the art and given in Abraham et al., supra. The intratumoral dose of a cytotoxic drug administered to the tumor site generally ranges from about 0.1 to 500, more usually about 0.5 to 300 mg/kg body weight, depending upon the nature of the drug, size of tumor, and other considerations. The intratumoral chemotherapy is given after at least 2-7 weekly of intratumoral SAg injections and within 36 hours after the previous SAg treatment. The SAg and chemotherapy are given at the same time and continued every 7 days for at least 3 treatments and up to 6 weekly treatments if the tumor is shrinking and the there is no dose limiting toxicity.

Systemic chemotherapy is also used in doses 10-95% below the mean recommended therapeutic dose for a single agent alone or in combination with other chemotherapeutic agents. While a range of 10-95% reduction is useful, chemotherapeutic doses 50% below the recommended mean dose per cycle are used most often. Systemic or intratumoral chemotherapy is also started after the first SAg treatment but is usually given within 36 hours after 2-7 intratumoral SEA treatments. The SEA and chemotherapy is also given at the same time beginning with the first treatment but generally after 2-7 SEA treatments. The intratumoral chemotherapy is continued alone or together with intratumoral SEA for at least 3 weekly injections after at least 2-7 intratumoral treatments with SEA alone It is continued for an additional 3-6 weeks if the tumor is shrinking and there is no dose limiting toxicity.

In the case of a lung tumor, a typical treatment consists of percutaneous or transbronchial injection of a lung tumor nodule intratumorally with SEA 5 ng every 7 days for 7 weeks followed by SEA 5 ng with cisplatin 10 mg intratumorally every 7 days for three weeks. The chemotherapy is used alone (i.e. without the SEA) or together with SEA for the last three treatments. For large tumors exceeding 40 cm$^2$ (two dimensions), injections are given at more than one site in the tumor mass using doses that cumulatively do not exceed that of a single dose per cycle. Likewise, additional malignant nodules or masses are treated in the same fashion as large single nodules. Alternatively, additional nodules are treated sequentially following the completion of one cycle in a single mass. Representative doses of single agent chemotherapeutic agents used in an average sized adult for intratumoral injection against the more common tumors are, (1) Breast carcinomas: Doxorubicin (14-30 mg/treatment×3), Taxol (30 mg/treatment×3); (2) Colo-rectal cancer: 5-Fluorouricil (180 200 mg/treatment×3); Lung cancer: cisplatin (4-10 mg/treatment×3). The drugs are administered intratumorally in 1 ml normal saline over a 1 minute period.

Patient Evaluation: Assessment of response of the tumor to the therapy is made once per week during therapy and 30 days thereafter using CT or x-ray visualization. Depending on the response to treatment, side effects, and the health status of the patient, treatment is terminated or prolonged from the standard protocol given above. Tumor response criteria are those established by the WHO and RECIST (Response Evaluation Criteria in Solid Tumors) summarized below (also Abraham et al., supra)

| RESPONSE | DEFINITION |
| --- | --- |
| Complete remission (CR) | Disappearance of all evidence of disease |
| Partial remission (PR) | 50% decrease in the product of the two greatest perpendicular tumor diameters; no new lesions |
| Less than partial remission (<PR) | 25%-50% decrease in tumor size, stable for at least 1 month |
| Stable disease | <25% reduction in tumor size; no progression or new lesions |
| Progression | ≧25% increase in size of any one measured lesion or appearance of new lesions despite stabilization or remission of disease in other measured sites |

The efficacy of the therapy in a patient population is evaluated using conventional statistical methods, including, for example, the Chi Square test or Fisher's exact test. Long-term changes in and short term changes in measurements are evaluated separately.

Results

A total of 810 patients are patients treated. The number of patients for each tumor type and the results of treatment are summarized in Table 10. Positive tumor responses are observed in as high as 80-90%% of the patients with breast, gastrointestinal, lung, prostate, renal and bladder tumors as well as melanoma and neuroblastoma as follows:

Six hundred and sixty five patients with all tumors exhibit objective clinical responses for an overall response rate of 82%. Tumors generally start to diminish and objective remissions are evident after four weeks of combined SEA-chemotherapy. Responses endure for an average of 24 months.

Toxicity consists of mild short-lived fever, fatigue and anorexia not requiring treatment.

The incidence of side effects (as % of total treatments) are as follows: chills—10; fever—10; pain—5; nausea—5; respiratory—3; headache—3; tachycardia—2; vomiting—2; hypertension—2; hypotension—2; joint pain—2; rash—2; flushing—1; diarrhea—1; itching/hives—1; bloody nose—1; dizziness—<1; cramps—<1; fatigue—<1; feeling faint—<1; twitching—<1; blurred vision—<1; gastritis<1; redness on hand—<1. Fever and chills are the most common side effects observed. Side effects are somewhat less frequent in patients treated with intratumoral SAg plus low dose single agent chemotherapy compared with SAg and full dose systemic chemotherapy. Side effects are less prevalent with the intratumoral SAg-chemotherapy regimen compared with SAg and full dose systemic chemotherapy regimen but this is not statistically different. CBC, renal and liver functions tests do not change significantly after treatments.

TABLE 10

| All Patients | No. | Response | % of Patients Responding |
| --- | --- | --- | --- |
|  | 567 | CR | 70 |
|  | 70 | PR | 8.6 |
|  | 28 | <PR | 3.4 |
| By Tumor Type: | | | |
| Breast adenocarcinoma | 100 | CR + PR + <PR | 80% |
| Gastrointestinal carcinoma | 100 | CR + PR + <PR | 85% |
| Lung Carcinoma | 150 | CR + PR + <PR | 90% |
| Brain glioma/astrocytoma | 50 | CR + PR + <PR | 80% |
| Prostate Carcinoma | 100 | CR + PR + <PR | 80% |
| Lymphoma/Leukemia | 80 | CR + PR + <PR | 75% |
| Head and Neck Cancer | 80 | CR + PR + <PR | 75% |
| Renal and Bladder Cancer | 50 | CR + PR + <PR | 90% |
| Melanoma | 50 | CR + PR + <PR | 80% |
| Neuroblastoma | 50 | CR + PR + <PR | 80% |

Example 4

Treatment Plan and Outcome Prediction using Intrapleural Superantigens

Patients have with malignant pleural effusions confirmed by biopsy or pleural fluid cytology and have not been undergoing any other anticancer treatment for at least one month and have a clinical Kamofsky status of at least 60-70%. SEA in doses of 10-30 nanograms is administered intrapleurally once or twice weekly immediately after drainage of the effusion via conventional thoracentesis. This procedure is performed once or twice weekly in an outpatient or office setting. Treatment is continued once weekly until effusion does not recur. An objective response is recognized as no reaccumulation of pleural fluid 30 days after treatment (DeCamp M M et al., *Chest* 112: 291S-295S (1997); Fenton K N et al., *Am J. Surg.* 170: 69-74 (1995)).

There are 90 evaluable patients with malignant pleural effusions treated with intrapleural SEA. All patients have stage IIIb or stage IV lung cancer. There are 50 evaluable patients with malignant ascites. Eighty five patients with pleural effusions exhibit objective clinical responses for a response rate of 94.5%. Effusion reaccumulation (at weekly intervals) progressively diminished after each SEA treatment. An example of progressive reduction of effusion reaccumulation after each treatment is shown below. Patients required an average of three treatments before there was no significant reaccumulation. However, several patients required only one treatment to eliminate fluid reaccumulation. Forty five patients with malignant ascites show objective responses for a response rate of 90%.

Toxicity in both malignant pleural effusion and ascites consists of mild short-lived fever, fatigue and anorexia not requiring treatment. CBC, renal and liver functions tests did not change significantly after treatments.

The SAg has better therapeutic efficacy for malignant pleural effusions and ascites than existing agents (talc, bleomycin, doxycycline) without the discomfort and complications associated with an indwelling draining chest tube. In the case of pleural effusion, It is also 90% more cost-effective compared to existing therapy since it is carried out in an outpatient facility and does not involve the major costs associated with hospitalization, i.e., chest tube insertion, operating and recovery room, indwelling chest tube drainage and respiratory therapy.

Example 5

Anti-Tumor Effects of Intratumoral SAgs and Chemotherapeutic Agents Administered in Viscous Form of Controlled Release Formulation The SAgs and chemotherapeutic agents are prepared in controlled release formulations. The preparation of the preferred biodegradable controlled release formulation for intratumoral administration of SAg and cisplatin as a preferred single agent for use in patients with NSCLC is described. Cisplatin is a representative chemotherapeutic agent; other chemotherapeutic agents preferred for a given type of tumor be prepared an used similarly with slight variations that are within the skill of the art.

Cisplatin for Injection, USP (10 mg vial) manufactured by Bristol Laboratories or lyophilized CDDP manufactured by Faulding (David Bull Laboratories, Australia) is used. Aqueous collagen gel, 6.5% is obtained from Collagen Corporation (Palo Alto, Calif.), 0.3 ml nominal fill in 1 ml plastic syringes. The gel comprises a highly purified, telopeptide-free bovine Type I collagen, 6.5% (w/w); sodium phosphates, 0.1 M; sodium chloride, 0.045 M; and has a nominal pH of 7.2. Optionally epinephrine is used as a solution (1 mg/ml). Polysorbate 80 is obtained from PPG Industries. Carboxymethylcellulose sodium (NaCMC) is obtained from Aqualon. 0.9% Sodium Chloride for injection, USP (10 ml vial) ("saline") and sterile water for injection ('WFI'), USP (10 ml vial) may be obtained from common sources (e.g., Abbott Laboratories).

Diluent contain polysorbate 80, 1.0 mg; EDTA disodium dihydrate, 0.1 mg; USP carboxymethylcellulose 0.5 mg; sodium metabisulfite, 0.2 mg; glacial acetic acid USP, 0.49 mg; sodium acetate, anhydrous, 0.15 mg; WFI up to 1 ml. HCl and/or NaOH may be added if necessary, to adjust pH to 4.0. USP epinephrine, 0.160 mg is also optional. A second diluent contains all of the above ingredients except for carboxymethylcellulose.

The viscous form of Cisplatin is prepared by diluting 5-10 mg in 1-4 cc of diluent. The resulting solution is very viscous and can serve as a controlled release formulation upon injection into tumor. This is the preferred method of administration of this drug. SAg can be present in the same solution as cisplatin as a viscous mixture. In this way Both cisplatin and SAg can be injected into the tumor at the same time.

The gel is prepared by combining the various components in a sterile environment. Upon admixture of the bovine collagen matrix and other agents, a uniform dispersion is obtained. For collagen and collagen derivatives, the material is provided as a uniform dispersion of collagen fibrils in an aqueous medium, where the collagenous material ranges in concentration from about 5 mg/ml to not more than about 100 mg/ml. The drug and or SAg may then be added to the collagenous dispersion using agitation to ensure uniform dispersion of the active agents. Other materials, as appropriate, may be added concomitantly or sequentially. After ensuring the uniform dispersion of the various components in the mixture, the mixture is sterilized and sealed in appropriate containers.

Vials containing either 10 mg or 25 mg of lyophilized CDDP are reconstituted by adding either 1.6 ml or 4.0 ml of diluent, respectively, to yield a suspension of CDDP. SEA is similarly reconstituted in sterile saline and added in desired concentration to the CDDP solution. Gels containing CDDP/SEA are prepared in final volumes of 2.0 ml or 5.0 ml. Final gels contained 4.0 mg/ml CDDP/5 ng SEA and 0.1 mg/ml of epinephrine, in a 2% collagen matrix, ready for use.

Intratumoral Therapy: Therapy preferably comprises the use of a selected single agent ((chemo- or biotherapeutic) which is known in the art to be effective against a particular tumor, e.g., cisplatin/carboplatin for NSCLC, doxorubicin/taxotere for breast carcinoma, 5-Fluoruricil for colorectal carcinoma, etc. Intratumoral combination chemotherapy wherein each agent is given in a reduced dose are also used. The intratumoral injection of SEA, 0.05-0.5 ng/kg, is given once weekly for 2-7 weeks. The chemotherapy is started within 36 hours of the last dose of SEA and then every 7 days for 3 treatments. SEA can also be given together with the chemotherapy or beginning with the first injection or second injection of chemotherapy.

The dose of a chemotherapeutic drug or biologic agent used for intratumoral administration, is reduced 10- to 50-fold below the mean FDA-recommended dose for parenteral administration in a single cycle. Chemotherapeutic concentrations in the sustained release preparation range from 0.01 to 50 mg/ml. Chemotherapy is given within 36 hours after the $7^{th}$ intratumoral SEA injection and continued once weekly for at least three weeks. It is extended to six or more weeks if the tumor is diminishing in size and there is no dose limiting toxicity. Injection of the dose is given at more than one site in tumors exceeding 40 cm$^2$. In this case the dose is divided into two or more portions with the cumulative dose per treatment not to exceed that for a single site full dose.

Illustrative of the manner of sustained administration is intratumoral administration of cis-diaminodichloroplatinum (CDDP) in controlled release formulation for which the recommended intratumoral dose per weekly injection is 0.05-0.1 mg/kg with a total dose range dose of 12-30 mg per cycle. SEA is administered intratumorally in doses of 0.05-1 ng/kg intratumorally once weekly for 2-7 weeks followed by CDDP (4-10 mg) weekly for 3 weeks. The tumors are accessed via percutaneous injection using CT, ultrasound or stereotaxis to localize and guide the injected composition into the tumor. In certain instances, the tumors are injected under direct vision at surgery, or via bronchoscopy, thoracoscopy, endoscopy, peritoneoscopy, or culdocopy.

TABLE 11

| All Patients | No. | Response | % of Patients Responding |
|---|---|---|---|
|  | 657 | CR | 80 |
|  | 23 | PR | 3 |
|  | 8 | <PR | 1 |
| By Tumor Type: |  |  |  |
| Breast adenocarcinoma | 150 | CR + PR + <PR | 90% |
| Gastrointestinal carcinoma | 150 | CR + PR + <PR | 90% |
| Lung Carcinoma | 150 | CR + PR + <PR | 95% |
| Brain glioma/astrocytoma | 50 | CR + PR + <PR | 85% |
| Prostate Carcinoma | 100 | CR + PR + <PR | 85% |
| Lymphoma/Leukemia | 80 | CR + PR + <PR | 80% |
| Head and Neck Cancer | 80 | CR + PR + <PR | 80% |
| Renal and Bladder Cancer | 50 | CR + PR + <PR | 95% |
| Melanoma | 50 | CR + PR + <PR | 85% |
| Neuroblastoma | 50 | CR + PR + <PR | 85% |

Results: A total of 910 patients are patients treated. The number of patients for each tumor type and the results of treatment are summarized in Table 11. Positive tumor responses are observed in as high as 85-95% of the patients with breast, gastrointestinal, lung, prostate, renal and bladder tumors as well as melanoma and neuroblastoma as follows.

Seven hundred and seventy three patients of 910 entered with all tumors exhibit objective clinical responses for an overall response rate of 84%. Tumors generally start to diminish and objective remissions are evident after four weeks of combined SEA-chemotherapy. Responses endure for an mean of 36 months.

Toxicity consists of mild short-lived fever, fatigue and anorexia not requiring treatment. The incidence of side effects (as % of total treatments) are as follows: chills—12; fever—15; pain—6; nausea—3; respiratory—2; headache—2; tachycardia—4; vomiting—4; hypertension—1; hypotension—2; joint pain—3; rash—1; flushing—4; diarrhea—2; itching/hives—1; bloody nose—1; dizziness—<1; cramps—<1; fatigue—<1; feeling faint—<1; twitching—<1; blurred vision—<1; gastritis<1; redness on hand—<1. Fever and chills are the most common side effects observed. Toxic effects usually associated with systemically administered chemotherapeutic agents were not observed. For example, neurotoxicity, hematologic toxicity, and ototoxicity associated with systemically administered cisplatin were not observed. The bone marrow depression commonly observed with parenterally administered chemotherapy such as antimetabolites, e.g., 5-Fluorouricil, Methotrexate; alkylating agents, e.g., cyclophosphamide, Ifosamide; tumor antimicrobials, e.g., doxorubicin, mitomycin C; plant alkaloids, e.g., Taxol, Taxotere; other agents, e.g., Cisplatin, Carboplatin, Irinotecan 5-Fluorouricil, Taxol, Taxotere is not seen with intratumoral administration of the these agents in controlled release formulation. Unique toxicities of single agents such as cardiomyopathy with the anthracycline antibiotics Doxorubicin, Daunorubicin, hemorrhagic cystitis with Cyclophosphamide and Ifosamide, neurotoxicity with 5-Fluorouricil, neuropathy and arrythmias with Taxol, severe diarrhea with Irinotecan, interstitial pneumonia and hemolytic-uremic syndrome with Mitomycin C are not observed when administered intratumorally as controlled release formulations. Of note, with all intratumoral chemotherapy in this form, there is minimal hematologic toxicity of the intratumorally administered chemotherapeutic agents and no significant renal and liver toxicity.

All the references cited above are all incorporated by reference herein, whether specifically incorporated or not.

In addition, the following co-pending patent applications are incorporated by reference in their entirety:

| Inventor | Serial No. | Filing Date | Title |
|---|---|---|---|
| Terman, D. S. | 60/438,686 | Jan. 9, 2003 | Intrathecal and Intrapleural Superantigens to Treat Malignant Disease |
| Terman, D. S. | 60/415,310 | Oct. 1, 2002 | Intrathecal and Intratumoral Superantigens to Treat Malignant Disease. |
| Terman, D. S. | 60/406,750 | Aug. 29, 2002 | Intrathecal Superantigens to Treat Malignant Fluid Accumulation |
| Terman, D. S. | 60/415,400 | Oct. 2, 2002 | Composition and Methods for Treatment of Neoplastic Diseases |
| Terman, D. S. | 60/406,697 | Aug. 28, 2002 | Compositions and Methods for Treatment of Neoplastic Diseases |
| Terman, D. S. | 60/389,366 | Jun. 15, 2002 | Compositions and Methods for Treatment of Neoplastic Diseases |
| Terman, D. S. | 60/378,988 | May 8, 2002 | Compositions and Methods for Treatment of Neoplastic Diseases |
| Terman, D. S. | 09/870,759 | May 30, 2001 | Compositions and Methods for Treatment of Neoplastic Diseases |
| Terman, D. S. | 09/751,708 | Dec. 28, 2000 | Compositions and Methods for Treatment of Neoplastic Diseases |

Having now fully described this invention, it will be appreciated by those skilled in the art that the same can be performed within a wide range of equivalent parameters, concentrations, and conditions without departing from the spirit and scope of the invention and without undue experimentation.

What is claimed is:

1. A method of treating a subject with a carcinoma comprising administering to said subject parenterally by infusion or injection a tumoricidally effective amount of a composition consisting of:

(i) a native staphylococcal enterotoxin or streptococcal pyrogenic exotoxin protein which native protein:

(a) has the biological activity of stimulating T cell mitogensis via a T cell receptor vβ region or (ii) a biologically active homologue or fragment of a native staphylococcal enterotoxin or streptococcal pyrogenic exotoxin, which homologue or fragment:

(a) has the biological activity of stimulating T cell mitogenesis via a T cell receptor vβ region and (b) has sequence homology characterized as a z value exceeding 13 when the sequence of the homologue or said fragment is compared to the sequence of a native staphylococcal enterotoxin or a native streptococcal progenic exotoxin, determined by FASTA analysis using gap penalties of -12 and -2, Blosum 50 matrix and Swiss-PROT or PIR database; or (iii) a biologically active fusion protein having said biological activity and said sequence homology, comprising (A) said homologue, (B) a native staphylococcal enterotoxin, (C) a native streptococcal pyrogenic exotoxin, or (D) a biologically active fragment of said homologue, said native enterotoxin or said native exotoxin, fused to a peptide or polypeptide fusion partner, wherein a chemotherapeutic drug or drugs is/are administered parenterally by infusion or injection before, together with or after administration of said enterotoxin or exotoxin composition.

2. A method of treating a subject with a carcinoma comprising administering to said subject parenterally by infusion or injection a tumoricidally effective amount of a composition consisting of:

(i) a native staphylococcal enterotoxin or streptococcal pyrogenic exotoxin protein which native protein:

(a) has the biological activity of stimulating T cell mitogensis via a T cell receptor vβ region or (ii) a biologically active homologue or fragment of a native staphylococcal enterotoxin or streptococcal pyrogenic exotoxin, which homologue or fragment:

(a) has the biological activity of stimulating T cell mitogenesis via a T cell receptor vβ region and (b) has sequence homology characterized as a z value exceeding 13 when the sequence of the homologue or said fragment is compared to the sequence of a native staphylococcal enterotoxin or a native streptococcal pyrogenic exotoxin, determined by FASTA analysis using gap penalties of −12 and −2, Blosum 50 matrix and Swiss-PROT or PIR database; or (iii) a biologically active fusion protein having said biological activity and said sequence homology, comprising (A) said homologue, (B) a native staphylococcal enterotoxin, (C) a native streptococcal pyrogenic exotoxin, or (D) a biologically active fragment of said homologue, said native enterotoxin or said native exotoxin, fused to a peptide or polypeptide fusion partner, wherein a therapeutic dose of x-irradiation is administered before, together with or after administration of said enterotoxin or exotoxin composition.

3. The method of claim 1 wherein the chemotherapy is selected from a group consisting of heavy metals, antimetabolites, anthracyclines, vinca alkaloids, anti-tubulin drugs, antibiotics and alkylating agents.

4. The method of claim 2 wherein x-irradiation to the carcinoma in doses of 60-65Gy beginning up to 30 days before, at the same time or 30 days after the start of said administration of said staphylococcal enterotoxin or streptococcal pyrogenic exotoxin composition.

* * * * *